US012692546B2

(12) United States Patent (10) Patent No.: US 12,692,546 B2
Alexander et al. (45) Date of Patent: Jul. 28, 2026

(54) PERSONALIZED CTDNA DISEASE MONITORING VIA REPRESENTATIVE DNA SEQUENCING

(71) Applicants: VENTANA MEDICAL SYSTEMS, INC., Tucson, AZ (US); THE FRANCIS CRICK INSTITUTE LIMITED, London (GB); THE ROYAL MARSDEN NHS FOUNDATION TRUST, London (GB)

(72) Inventors: Nelson R. Alexander, Marana, AZ (US); Kevin Richard Litchfield, London (GB); Stacey Stanislaw, Tucson, AZ (US); Samra Turajlic, London (GB)

(73) Assignees: Ventana Medical Systems, Inc., Tucson, AZ (US); The Francis Crick Institute Limited, London (GB); The Royal Marsden NHS Foundation Trust, London (GB)

( * ) Notice: Subject to any disclaimer, the term of this patent is extended or adjusted under 35 U.S.C. 154(b) by 1078 days.

(21) Appl. No.: 17/314,958

(22) Filed: May 7, 2021

(65) Prior Publication Data

US 2022/0064733 A1 Mar. 3, 2022

Related U.S. Application Data

(63) Continuation of application No. PCT/US2019/062857, filed on Nov. 22, 2019.

(60) Provisional application No. 62/772,650, filed on Nov. 29, 2018.

(51) Int. Cl.
*C12Q 1/6886* (2018.01)
*C12Q 1/6869* (2018.01)
*C12Q 1/6883* (2018.01)

(52) U.S. Cl.
CPC ......... *C12Q 1/6886* (2013.01); *C12Q 1/6869* (2013.01); *C12Q 1/6883* (2013.01); *C12Q 2600/106* (2013.01); *C12Q 2600/156* (2013.01); *C12Q 2600/158* (2013.01)

(58) Field of Classification Search
None
See application file for complete search history.

(56) References Cited

U.S. PATENT DOCUMENTS

| | | | | |
|---|---|---|---|---|
| 11,959,838 B2 * | 4/2024 | Alexander | ......... | G01N 33/5091 |
| 2009/0246788 A1 | 10/2009 | Albert et al. | | |
| 2015/0178445 A1 | 6/2015 | Cibulskis et al. | | |
| 2017/0275689 A1 * | 9/2017 | Maguire | ............. | C12Q 1/6818 |
| 2018/0320229 A1 | 11/2018 | Alexander et al. | | |

FOREIGN PATENT DOCUMENTS

| | | | |
|---|---|---|---|
| WO | 2013068528 A1 | 5/2013 | |
| WO | 2014106076 A2 | 7/2014 | |
| WO | 2014144478 A2 | 9/2014 | |
| WO | 2015058093 A1 | 4/2015 | |
| WO | 2017007976 A1 | 1/2017 | |
| WO | 2017085307 A1 | 5/2017 | |
| WO | WO-2017079763 A1 * | 5/2017 | |
| WO | WO-2017123316 A1 * | 7/2017 | |
| WO | 2018189040 A1 | 10/2018 | |

OTHER PUBLICATIONS

Liang et al PLoS ONE. Oct. 2012. 7(1): e43192, p. 1-20 (Year: 2012).*
Yates et al. Nature Medicine. Jun. 22, 2015. 21(7): 751-759 and "Online Methods", 13 pages (Year: 2015).*
Bai et al Nature Genetics. Published online Nov. 2015. 48(1): 59, p. 1-11 (Year: 2015).*
Patel et al J. vis. Exp. 114, e54299, 10 pages (Year: 2016).*
Computational methods for discovering structural variation with next-generation sequencing, Nature Methods Supplement, vol. 6, No. 11, Nov. 2009 pp. 13-20.
Gerlinger, et al., Intratumor Heterogeneity, and Branched Evolution Revealed by Multiregion Sequencing, Sep. 6, 2012, vol. 366, pp. 883-892, The New England Journal of Medicine.
Hyman, Edward David, A New Method of Sequencing DNA, Analytical Biochemistry, vol. 174, pp. 423-436, 1988.
Rhonaghi et al., A Sequencing Method Based on Real-Time Pyrophosphate, Jul. 17, 1998, vol. 281, No. 375, pp. 363-365, Science, USA.
TissueLyser Handbook_For High-throughput disruption of biological samples_Second Edition_October 2010.
Xie, et. al., CNV-seq, a new method to detect copy number variation using high-throughput sequencing, Mar. 6, 2009, 10:80, BMC Bioinformatics, USA, pp. 1-9.
Yachida et al., Distant metastasis occurs late during the genetic evolution of pancreatic cancer, Oct. 28, 2010, vol. 467(7319), pp. 1114-1117, Nature , USA.
Yoon, et al., Sensitive and accurate detection of copy number variants using read depth of coverage, Aug. 5, 2009, 19(9), pp. 1586-1592, Genome Research, USA.
International Search Report and Written Opinion for PCT/US2019/062857 dated Apr. 6, 2020.
Steffen Dietz et al., "Low Input Whole-Exome Sequencing to Determine the Representation of the Tumor Exome in Circulating DNA of Non-Small Cell Lung Cancer Patients", PLOS ONE, vol. 11, No. 8, Aug. 16, 2016 (Aug. 16, 2016), p. e0161012.

(Continued)

*Primary Examiner* — Carla J Myers
(74) *Attorney, Agent, or Firm* — Charney IP Law LLC; Thomas M. Finetti

(57) ABSTRACT

Disclosed herein is a method of deriving a plurality of genetic variants from a homogenized input sample. Also disclosed herein are methods of identifying a plurality of genetic variants in a sample comprising: homogenizing one or more input samples to provide a homogenized sample; preparing genomic material isolated from the homogenized input sample for sequencing; and identifying the plurality of genetic variants within sequencing data derived after sequencing the prepared genomic material.

22 Claims, 26 Drawing Sheets

(56)                    References Cited

OTHER PUBLICATIONS

Angel E. Dago et al., "Rapid Phenotypic and Genomic Change in Response to Therapeutic Pressure in Prostate Cancer Inferred by High Content Analysis of Single Circulating Tumor Cells", Plos One, vol. 9, No. 8, Aug. 1, 2014 (Aug. 1, 2014), p. e101777.

Christopher Abbosh et al., "Phylogenetic ctDNA analysis depicts early-stage lung cancer evolution", Nature, vol. 545, No. 7655, Apr. 26, 2017 (Apr. 26, 2017), p. 446-451.

Mariam Jamal-Hanjani et al., "Tracking the Evolution of Non-Small-Cell Lung Cancer", The New England Journal of Medicine,—NEJM—, vol. 376, No. 22, Jun. 1, 2017.

Sahin et. al., "Personalized RNA mutanome vaccines mobilize poly-specific therapeutic immunity against cancer," Nature, vol. 000, 00 Month 2017, doi:10.1038/nature23003.

Ott et. al. "An immunogenic personal neoantigen vaccine for patients with melanoma," Nature, vol. 000, 00 Month 2017, doi:10.1038/nature22991.

Roth, A. et al. PyClone: statistical inference of clonal population structure in cancer. Nat Methods 11, 396-398 (2014).

Wong, S.Q et al. Sequence artefacts in a prospective series of formalin-fixed tumors tested for mutations in hotspot regions by massively parallel sequencing. BMC medical genomics 7, 23 (2014).

Rosenthal, R., McGranahan, N., Herrero, J., Taylor, B.S. & Swanton, C. DeconstructSigs: delineating mutational processes in single tumors distinguishes DNA repair deficiencies and patterns of carcinoma evolution. Genome biology 17, 31 (2016).

Andreatta, M. & Nielsen, M. Gapped sequence alignment using artificial neural networks: application to the MHC class I system. Bioinformatics 32, 511-517 (2016).

Shukla, S.A. et al. Comprehensive analysis of cancer-associated somatic mutations in class I HLA genes. Nature biotechnology 33, 1152-1158 (2015).

Carter, S.L. et al. Absolute quantification of somatic DNA alterations in human cancer. Nat Biotechnol 30, 413-421 (2012).

Nilsen, G. et al. Copynumber: Efficient algorithms for single- and multi-track copy number segmentation. Bmc Genomics 13 (2012).

Talevich, E., Shain, A.H., Botton, T. & Bastian, B.C. CNVkit: Genome-Wide Copy Number Detection and Visualization from Targeted DNA Sequencing. Plos Comput Biol 12 (2016).

Wang, K., Li, M.Y. & Hakonarson, H. Annovar: functional annotation of genetic variants from high-throughput sequencing data. Nucleic Acids Res 38 (2010).

Gerstung, M. et al. Reliable detection of subclonal single-nucleotide variants in tumor cell populations. Nature communications 3, 811 (2012).

Smith, T., Heger, A. & Sudbery, I. UMI-tools: modeling sequencing errors in Unique Molecular Identifiers to improve quantification accuracy. Genome research 27, 491-499 (2017).

Koboldt, D.C. et al. VarScan: variant detection in massively parallel sequencing of individual and pooled samples. Bioinformatics 25, 2283-2285 (2009).

Fang, H. et al. Indel variant analysis of short-read sequencing data with Scalpel. Nat Protoc 11, 2529-2548 (2016).

Cibulskis, K. et al. Sensitive detection of somatic point mutations in impure and heterogeneous cancer samples. Nat Biotechnol 31, 213-219 (2013).

Li, H. & Durbin, R. Fast and accurate short read alignment with Burrows-Wheeler transform. Bioinformatics 25, 1754-1760 (2009).

Faustino-Rocha, A. et al. Estimation of rat mammary tumor vol. using caliper and ultrasonography measurements. Lab animal 42, 217-224 (2013).

Hedley, D.W., Friedlander, M.L., Taylor, I.W., Rugg, C.A. & Musgrove, E.A. Method for analysis of cellular DNA content of paraffin-embedded pathological material using flow cytometry. The journal of histochemistry and cytochemistry : official journal of the Histochemistry Society 31, 1333-1335 (1983).

Abbosh, C. et al. Phylogenetic ctDNA analysis depicts early-stage lung cancer evolution. Nature 545, 446-451 (2017).

Mcgranahan, N. et al. Clonal neoantigens elicit T cell immunoreactivity and sensitivity to immune checkpoint blockade. Science 351, 1463-1469 (2016).

Miao, D. et al. Genomic correlates of response to immune checkpoint blockade in microsatellite-stable solid tumors. Nature genetics 50, 1271-1281 (2018).

Consortium, A.P.G. AACR Project GENIE: Powering Precision Medicine Through an International Consortium. Cancer discovery (2017).

Warrick, J.I. et al. Intratumoral Heterogeneity of Bladder Cancer by Molecular Subtypes and Histologic Variants. European urology (2018).

Jamal-Hanjani, M. et al. Tracking the Evolution of Non-Small-Cell Lung Cancer. The New England journal of medicine 376, 2109-2121 (2017).

Turajlic, S. et al. Deterministic Evolutionary Trajectories Influence Primary Tumor Growth: TRACERx Renal. Cell 173, 595-610 e511 (2018).

David, M. Handbook of Applied Advanced Geostatistical Ore Reserve Estimation. Elsevier: Amsterdam (1988).

Crespi, I. Pre-Election Polling: Sources of Accuracy and Error. (1988).

Rohde, A. Sampling and Homogenization Strategies Significantly Influence the Detection of Foodborne Pathogens in Meat. BioMed Research International (2015).

Gy, P. Heterogeneite, Echantillonnage, Homogeneisation (Heterogeneity, Sampling, Homogenizing). xiv+607 p (Masson: Paris) (1988).

Medvedev, et al., Computational methods for discovering structural variation with next-generation sequencing, nature methods Supplement, vol. 6 No. 11s, Nov. 2009, S13.

* cited by examiner

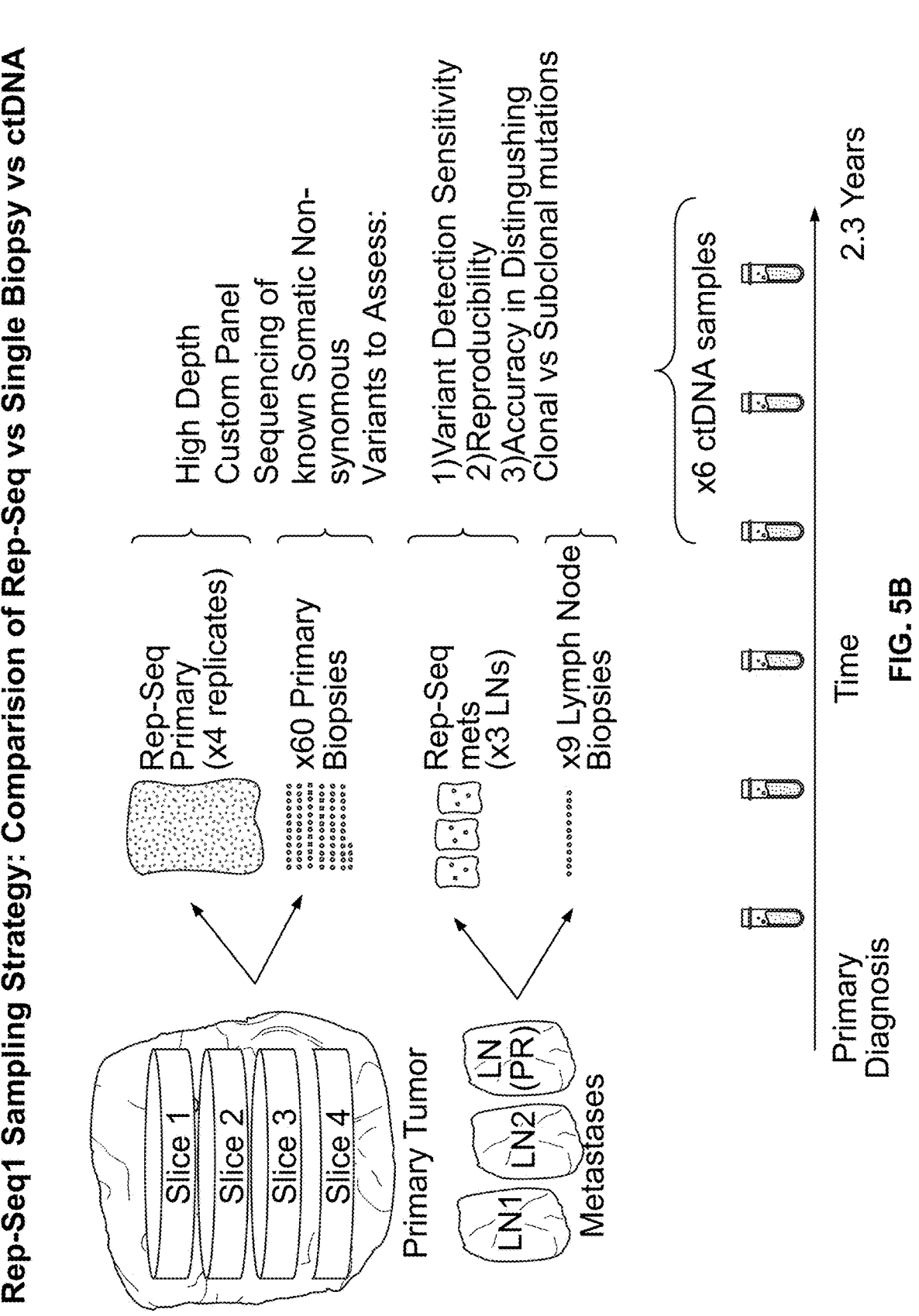

Rep-Seq1 Sampling Strategy: Comparision of Rep-Seq vs Single Biopsy vs ctDNA

High Depth Custom Panel Sequencing of known Somatic Non-synomous Variants to Assess:

1) Variant Detection Sensitivity
2) Reproducibility
3) Accuracy in Distinguishing Clonal vs Subclonal mutations Rep-Seq Primary (x4 replicates)

x60 Primary Biopsies

Rep-Seq mets (x3 LNs)

x9 Lymph Node Biopsies x6 ctDNA samples

Slice 1
Slice 2
Slice 3
Slice 4

Primary Tumor

LN1  LN2  LN (PR)

Metastases

Primary Diagnosis

Time 2.3 Years

FIG. 5B

Number of Predicted Neoantigens Detected in Case Rep-Seq1, by Different Sequencing Method Variant Allele Frequncy (Above or Below 5%) by Variant Base Change, for Cases Rep-Seq3-10

Figure 9:
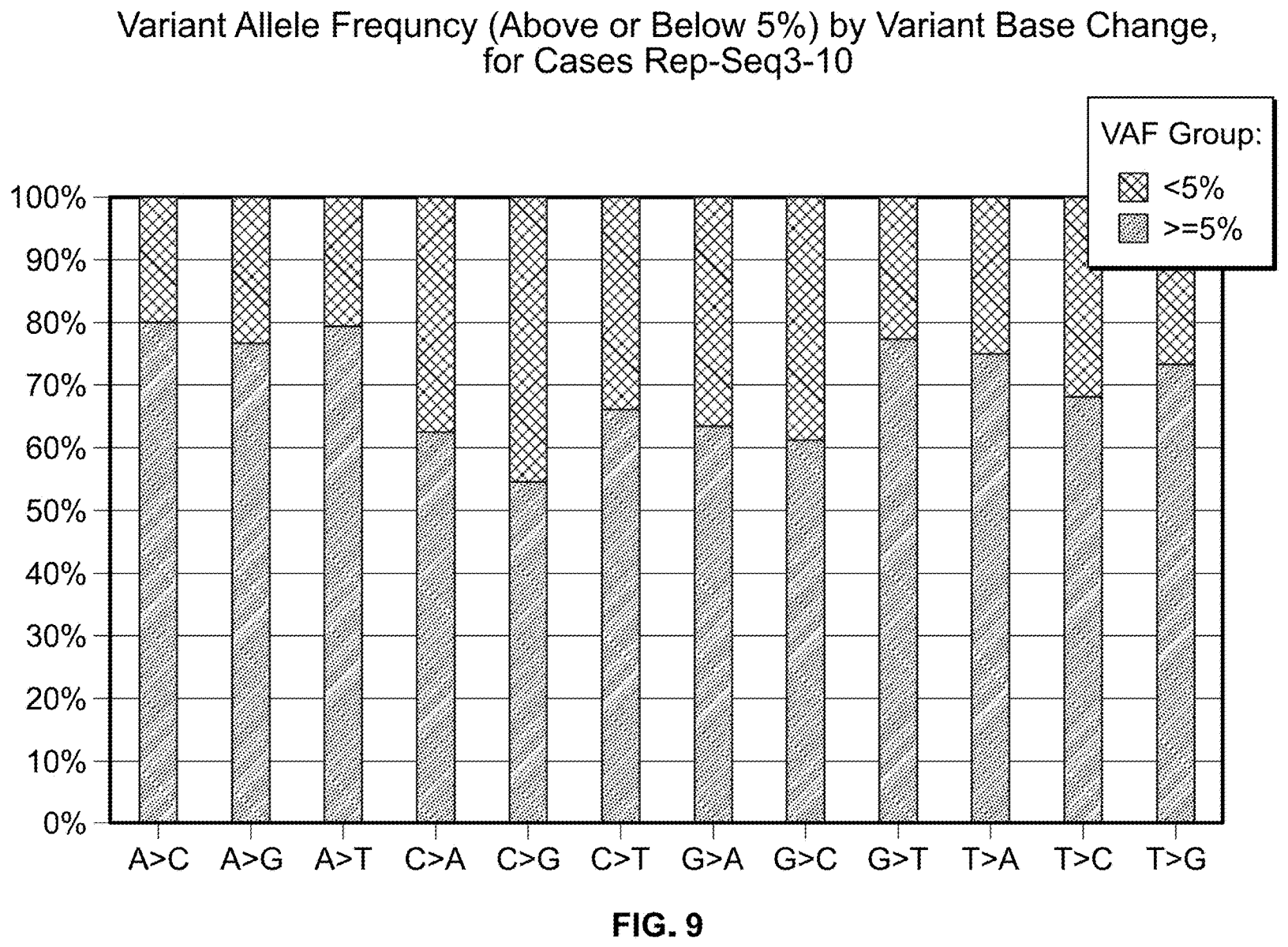

VAF Group:
<5%
>=5%

PERSONALIZED CTDNA DISEASE MONITORING VIA REPRESENTATIVE DNA SEQUENCING

CROSS-REFERENCE TO RELATED APPLICATIONS

The present application is a continuation of International Application No. PCT/US19/62857 filed on Nov. 22, 2019, which application claims the benefit of the filing date of U.S. Provisional Application No. 62/772,650 filed on Nov. 29, 2018, the disclosure of which is hereby incorporated by reference herein in its entirety.

BACKGROUND OF THE DISCLOSURE

Studies of human genetic variation using DNA sequencing have undergone an extraordinary development from their introduction over 40 years ago up to current technologies, which allow for a human genome to be sequenced and analyzed within a matter of days. The release of the first "next-generation sequencing" (NGS) instruments in the mid-2000s led to a revolution in disease study, offering vastly improved speed at significantly lower cost—enabling the generation of a whole human genome sequence in a matter of weeks. In addition to price and performance, the new sequencing technology also proved to compensate for some of the technical weaknesses of the older sequencing and genotyping technologies, allowing for the genome-wide detection of variants, including novel ones, at a low cost. A further breakthrough for NGS in human genomics arrived with the introduction of targeted enrichment methods, allowing for selective sequencing of regions of interest, thereby dramatically reducing the amount of sequences that needed to be generated. The approach is based on a collecting DNA or RNA probes representing the target sequences in the genome, which can bind and extract the DNA fragments originating from targeted regions.

Whole exome sequencing (WES), which enables sequencing of all protein-coding regions in the human genome (the exome) quickly became the most widely used targeted enrichment method, especially for monogenic ("Mendelian") diseases. This approach enabled the detection of both exonic (coding) as well as splice-site variants, while requiring only approximately 2% of sequencing "load" compared to whole genome sequencing. The unbiased analysis of all genes eliminated the need for a time-consuming selection of candidate genes prior to sequencing. It has been estimated that the exome harbors about 85% of mutations with large effects on disease-related traits. In addition, exonic mutations were shown to cause the majority of monogenic diseases, with missense and nonsense mutations alone accounting for approximately 60% of disease mutations.

Recent advances in genome sequencing technologies provide unprecedented opportunities to characterize individual genomic landscapes and identify mutations relevant for diagnosis and therapy. Indeed, in recent years, NGS has also been increasingly applied for addressing pharmacogenomic research questions. It is not only possible to detect genetic causes that explain why some patients do not respond to a certain drug, but also try to predict a drug's success based on genetic information. Certain genetic variants can affect the activity of a particular protein and these can be used to estimate the probable efficacy and toxicity of a drug targeting such a protein. NGS therefore has applications far beyond finding disease-causing variants.

About 99.5% of all DNA is shared across all humans; it is the 0.5% that makes all the difference. Genetic variations, or variants, are the differences that make each person's genome unique. DNA sequencing identifies an individual's variants by comparing the DNA sequence of an individual to the DNA sequence of a reference genome maintained by the Genome Reference Consortium (GRC). It is believed that the average human's genome has millions of variants. Some variants occur in genes but most occur in DNA sequences outside of genes. A small number of variants have been linked with diseases, such as cancer.

Cancer is a disease marked by the uncontrolled proliferation of abnormal cells. In normal tissue, cells divide and organize within the tissue in response to signals from surrounding cells, resulting in normal cellular behavior that is carefully orchestrated by the tissue context. Cancer cells do not respond to growth-limiting contextual cues from the surrounding tissue, and they often harbor genetic alterations that drive them to proliferate and, in many organs, form a tumor. As the growth of a tumor progresses, genetic and phenotypic alterations continue to accumulate, allowing populations of cancer cells to overcome additional "checkpoints," such as an anti-tumor immune response, and manifesting as a more aggressive growth phenotype of the cancer cells. If left untreated, metastasis, the spread of cancer cells to distant areas of the body by way of the lymphatic system or bloodstream, may ensue. Metastasis results in the formation of secondary tumors at multiple sites, damaging healthy tissue. Most cancer death is caused by such secondary tumors.

Current diagnostic oncology utilizes information taken from a fraction of a tumor and is predicated on the assumption that tumors are composed of cells that are uniform in their composition. Rather than being uniform in composition, many tumors are heterogeneous. Indeed, it has been reported that some solid tumors, rather than being homogeneous, are composed of multiple genetically distinct, spatially segregated populations of cancer cells. See Gerlinger et al., NEJM (2012) 366:883-92; and Yachida et al. Nature (2010) 467(7319):1114-1117, the disclosures of which are hereby incorporated by reference herein in their entireties. Conventional histological methodologies address this heterogeneity with the selection of multiple biopsy samples for analysis, e.g., based on morphology and other characteristics. For example, biopsy samples are taken from multiple regions of the tumor, wherein each sample taken comprises about 0.1 cubic centimeter of tissue. These methods survey more of the tumor tissue and different spatial areas of the tumor; however, the vast majority of the tumor assayed using such methods remains un-sampled. Similarly, conventional methods sample only a small portion of the lymph nodes from cancer patients and do not sample the vast majority of the tissue. The small size of these samples can also be limiting on the further diagnostic steps that are utilized, such as sequencing.

BRIEF SUMMARY OF THE DISCLOSURE

In one aspect of the present disclosure is a method of identifying a plurality of genetic variants in a sample (e.g. a sample derived from a human patient) comprising: homogenizing one or more tumor samples to provide a homogenized sample; preparing genomic material isolated from the homogenized sample for sequencing; and identifying the plurality of genetic variants within sequencing data derived after sequencing the prepared genomic material. In some embodiments, the method further comprises determining whether the identified plurality of genetic variants are clonal or subclonal. In some embodiments, one or more neoantigens are derived from the identified subclonal mutations. In some embodiments, the plurality of genetic variants are identified using whole genome sequencing (WGS), whole exome sequencing (WES), single nucleotide polymorphism (SNP) analysis, deep sequencing, sequencing-by-synthesis, targeted gene sequencing, or any combination thereof.

In some embodiments, the method further comprises generating a ctDNA monitoring panel based on the identified plurality of genetic variants. In some embodiments, the generated ctDNA monitoring panel is used to determine a response to therapy. In some embodiments, the generated ctDNA monitoring panel is used to determine an evolutionary trajectory of the cancer. In some embodiments, the generated ctDNA monitoring panel is used to predict a response to a future therapeutic strategy. In some embodiments, the generated ctDNA monitoring panel is used to ascertain a presence of cancer in a patient either during therapy or following therapy. In some embodiments, the generated ctDNA monitoring panel is used to ascertain the presence of cancer in a patient following disease remission, following a complete response to therapy, or following a diagnosis of undetectable disease. In some embodiments, the generated ctDNA monitoring panel is used to detect a minimal residual disease following surgical removal of a primary tumor. In some embodiments, the generated ctDNA monitoring panel is used to detect a minimal residual disease following surgical removal of a metastatic tumor.

In some embodiments, the method further comprises computing a clonal structure based on the identified plurality of genetic variants. In some embodiments, the computing of the clonal structure comprises (i) calculating cancer cell fraction estimates for each of the plurality of identified genetic variants; and (ii) grouping the calculated cancer cell fraction estimates into mutational clusters. In some embodiments, the method further comprises assessing the separation of individual identified genetic variants.

In some embodiments, the method further comprises sorting cellular particles within the homogenized sample prior to the preparing of the genomic material. In some embodiments, the sorting of the cellular particles is based on size. In some embodiments, the sorting of the cellular particles is based on a presence of one or more biomarkers.

In some embodiments, the method further comprises evaluating whether a human subject is at elevated risk of rapid disease progression if one or more particular subclonal variants are identified within the plurality of identified genetic variants. In some embodiments, the method further comprises determining whether an alternative therapy is needed based on the identification of one or more particular subclonal variants within the plurality of identified genetic variants.

In another aspect of the present disclosure is a method of identifying a plurality of genetic variants in a sample (e.g. a sample derived from a human patient) comprising: homogenizing one or more input samples to provide a homogenized sample; preparing genomic material isolated from the homogenized input sample for sequencing; and identifying the plurality of genetic variants within sequencing data derived after sequencing the prepared genomic material. In some embodiments, the method further comprises determining whether the identified plurality of genetic variants are clonal or subclonal. In some embodiments, one or more neoantigens are derived from the identified subclonal mutations. In some embodiments, the plurality of genetic variants are identified using whole genome sequencing (WGS), whole exome sequencing (WES), single nucleotide polymorphism (SNP) analysis, deep sequencing, targeted gene sequencing, or any combination thereof.

In some embodiments, the one or more input samples are derived from one or more of a tumor sample, lymph node sample, blood sample, and/or other tissue sample. In some embodiments, the one or more input samples are derived from one or more of a tumor sample and/or a blood sample. In some embodiments, the one or more input samples are derived from a tumor sample. In some embodiments, the input sample is derived from a human patient or mammalian subject (i) diagnosed with cancer, (ii) suspected of having cancer, (iii) at risk of developing cancer; (iv) at risk of relapse or recurrence of cancer; and/or (v) suspected of having cancer recurrence. In some embodiments, the input sample is derived from a healthy human patient or mammalian subject.

In some embodiments, the input sample comprises a representative sample of cells derived from a tumor sample, lymph node sample, blood sample, or any combination thereof. In some embodiments, the representative sample may be generated from an intact tumor biopsy sample from a solid tumor. In some embodiments, the biopsy sample comprises at least about 100 to about 200 cells. In some embodiments, the biopsy sample comprises at least about 200 to about 1,000 cells. In some embodiments, the biopsy sample comprises at least about 1,000 to about 5,000 cells. In some embodiments, the biopsy sample comprises at least about 10,000 to about 100,000 cells. In some embodiments, the biopsy sample comprises at least about 100,000 to about 1,000,000 or more cells.

In some embodiments, the method further comprises generating a ctDNA monitoring panel based on the identified plurality of genetic variants. In some embodiments, the generated ctDNA monitoring panel is used to determine a response to therapy. In some embodiments, the generated ctDNA monitoring panel is used to determine an evolutionary trajectory of the cancer. In some embodiments, the generated ctDNA monitoring panel is used to predict a response to a future therapeutic strategy. In some embodiments, the generated ctDNA monitoring panel is used to ascertain a presence of cancer in a patient either during therapy or following therapy. In some embodiments, the generated ctDNA monitoring panel is used to ascertain the presence of cancer in a patient following disease remission, following a complete response to therapy, or following a diagnosis of undetectable disease. In some embodiments, the generated ctDNA monitoring panel is used to detect a minimal residual disease following surgical removal of a primary tumor. In some embodiments, the generated ctDNA monitoring panel is used to detect a minimal residual disease following surgical removal of a metastatic tumor.

In some embodiments, the method further comprises computing a clonal structure based on the identified plurality of genetic variants. In some embodiments, the computing of the clonal structure comprises (i) calculating cancer cell fraction estimates for each of the plurality of identified genetic variants; and (ii) grouping the calculated cancer cell fraction estimates into mutational clusters. In some embodiments, the method further comprises assessing the separation of individual identified genetic variants.

In some embodiments, the method further comprises sorting cellular particles within the homogenized sample prior to the preparing of the genomic material. In some embodiments, the sorting of the cellular particles is based on size. In some embodiments, the sorting of the cellular particles is based on a presence of one or more biomarkers.

In some embodiments, the method further comprises evaluating whether a human subject is at elevated risk of rapid disease progression if one or more particular subclonal variants are identified within the plurality of identified genetic variants. In some embodiments, the method further comprises determining whether an alternative therapy is needed based on the identification of one or more particular subclonal variants within the plurality of identified genetic variants.

In another aspect of the present disclosure is a method of identifying a plurality of genetic variants in a sample (e.g. a sample derived from a human patient) comprising: obtaining a representative sample; and identifying the plurality of genetic variants within sequencing data derived after sequencing the representative sample. In some embodiments, the representative sample may be generated from an intact tumor biopsy sample from a solid tumor. In some embodiments, the biopsy sample comprises at least about 100 to about 200 cells. In some embodiments, the biopsy sample comprises at least about 200 to about 1,000 cells. In some embodiments, the biopsy sample comprises at least about 1,000 to about 5,000 cells. In some embodiments, the biopsy sample comprises at least about 10,000 to about 100,000 cells. In some embodiments, the biopsy sample comprises at least about 100,000 to about 1,000,000 or more cells.

In some embodiments, the representative sample may be obtained by homogenizing one or more input samples. In some embodiments, the one or more input samples are derived from one or more of a tumor sample, lymph node sample, blood sample, and/or other tissue sample. In some embodiments, the one or more input samples are derived from one or more of a tumor sample and/or a blood sample. In some embodiments, the one or more input samples are derived from a tumor sample. In some embodiments, the input sample is derived from a human patient or mammalian subject (i) diagnosed with cancer, (ii) suspected of having cancer, (iii) at risk of developing cancer; (iv) at risk of relapse or recurrence of cancer; and/or (v) suspected of having cancer recurrence. In some embodiments, the input sample is derived from a healthy human patient or mammalian subject.

In some embodiments, the method further comprises determining whether the identified plurality of genetic variants are clonal or subclonal. In some embodiments, one or more neoantigens are derived from the identified subclonal mutations. In some embodiments, the plurality of genetic variants are identified using whole genome sequencing (WGS), whole exome sequencing (WES), single nucleotide polymorphism (SNP) analysis, deep sequencing, sequencing-by-synthesis, targeted gene sequencing, or any combination thereof.

In some embodiments, the method further comprises generating a ctDNA monitoring panel based on the identified plurality of genetic variants. In some embodiments, the generated ctDNA monitoring panel is used to determine a response to therapy. In some embodiments, the generated ctDNA monitoring panel is used to determine an evolutionary trajectory of the cancer. In some embodiments, the generated ctDNA monitoring panel is used to predict a response to a future therapeutic strategy. In some embodiments, the generated ctDNA monitoring panel is used to ascertain a presence of cancer in a patient either during therapy or following therapy. In some embodiments, the generated ctDNA monitoring panel is used to ascertain the presence of cancer in a patient following disease remission, following a complete response to therapy, or following a diagnosis of undetectable disease. In some embodiments, the generated ctDNA monitoring panel is used to detect a minimal residual disease following surgical removal of a primary tumor. In some embodiments, the generated ctDNA monitoring panel is used to detect a minimal residual disease following surgical removal of a metastatic tumor.

In some embodiments, the method further comprises computing a clonal structure based on the identified plurality of genetic variants. In some embodiments, the computing of the clonal structure comprises (i) calculating cancer cell fraction estimates for each of the plurality of identified genetic variants; and (ii) grouping the calculated cancer cell fraction estimates into mutational clusters. In some embodiments, the method further comprises assessing the separation of individual identified genetic variants.

In some embodiments, the method further comprises sorting cellular particles within the homogenized sample prior to the preparing of the genomic material. In some embodiments, the sorting of the cellular particles is based on size. In some embodiments, the sorting of the cellular particles is based on a presence of one or more biomarkers.

In some embodiments, the method further comprises evaluating whether a human subject is at elevated risk of rapid disease progression if one or more particular subclonal variants are identified within the plurality of identified genetic variants. In some embodiments, the method further comprises determining whether an alternative therapy is needed based on the identification of one or more particular subclonal variants within the plurality of identified genetic variants.

While hundreds of thousands of solid tumors have been sequenced to date, a fundamental under-sampling bias is inherent in current methodologies. This is caused by a biopsy input sample of fixed dimensions, which becomes grossly under-powered as tumor volume scales. Indeed, our analysis of current clinical and research practice shows that existing protocols sample from only 0.0005% to 2.0% of the total tumor mass, raising the prospect of considerable sampling frame bias. Here we demonstrate Representative Sequencing (herein after "Rep-Seq"), as a novel method to achieve unbiased sampling of solid tumor tissue. The Rep-Seq protocol comprises homogenization of all residual tumor material not taken for pathology into a well-mixed solution, coupled with next generation sequencing. Rep-Seq was implemented on a proof of concept basis in 11 tumors, and benchmarked against single and multi-region sequencing approaches, at matched sequencing depths. Rep-Seq was able to detect more variants, achieve a greater accuracy in determining clonal from subclonal mutations, and deliver superior levels of reproducibility across replicates. In conclusion, Rep-Seq effectively implements an unbiased tumor sampling approach, drawing DNA molecules from a well-mixed solution of the entire tumor mass, hence removing spatial bias inherent in current approaches.

BRIEF DESCRIPTION OF THE FIGURES

For a general understanding of the features of the disclosure, reference is made to the drawings. In the drawings, like reference numerals have been used throughout to identify identical elements.

FIG. 4A (top) shows a density plot of the distribution of tumor volumes from the cancer genome atlas (TCGA), with tumor volume (cm3) plotted on the x-axis with log-scale. FIG. 4A (middle) shows a density plot of the volume of biopsy tissue used as input material for sequencing, in the same cohort of TCGA samples. FIG. 4A (bottom) shows the proportion of tissue sampled (i.e. values from middle panel divided by top panel for each case), split by tumor stage.

FIG. 4B (left) shows the estimated tumor volume $(cm^3)$ from the local clinical audit, split by tissue site. FIG. 4B (right) shows the proportion of tissue sampled, split by tissue site, in the clinical audit.

FIG. 4C shows the experimental design used for pilot experiment of pooled "cocktail" samples.

FIG. 4D (left) shows the variant allele frequency (VAF) correlation between cocktail sequencing (x-axis) compared to true VAFs estimated from multi-biopsy sequencing (y-axis). FIG. 4D (right) shows the variant allele frequency (VAF) correlation between single-region sequencing (x-axis) compared to true VAFs estimated from multi-biopsy sequencing (y-axis).

FIG. 4E (left) shows the number of variants discovered in each sequencing method in the pilot dataset for non-small cell lung cancer. FIG. 4E (right) shows the proportion of known true variants discovered using "cocktail" sequencing, compared to single-region biopsy sequencing for non-small cell lung cancer.

FIG. 4F (left) shows the number of variants discovered in each sequencing method in the pilot dataset for urothelial carcinoma. FIG. 4F (right) shows the proportion of known true variants discovered using "cocktail" sequencing, compared to single-region biopsy sequencing for urothelial carcinoma.

FIGS. 5A-5E illustrate a representative sampling sequencing method as described herein.

FIG. 5A illustrates a methodological workflow, for a new Representative Sequencing (Rep-Seq) methodology in accordance with some embodiments described herein.

FIG. 5B illustrates the sampling strategy, for validation of the Rep-Seq method against extensive biopsy sampling.

FIG. 5C illustrates the map of non-synonymous variants discovered, across all biopsies, ctDNA samples and Rep-Seq biological replicates, sequenced in case Rep-Seq1.

FIG. 5D illustrates Jaccard similarity index results, as a measure of reproducibility, for single biopsy sequencing versus Rep-Seq (left), and ctDNA sequencing versus Rep-Seq (right).

FIG. 5E provides a graph of variant allele frequency (VAF) versus variants detected for a Rep-Seq (VAF) sample and a whole tumor (VAF) sample.

FIG. 6A illustrates the phylogenetic tree for case Rep-Seq1, as derived using extensive multiple biopsy sequencing (left) and a single Rep-Seq sample.

FIG. 6B illustrates the Clonal distribution across the 4 slices of the primary Rep-Seg1 tumor, and lymph node metastases.

FIG. 6C illustrates the cancer cell fraction (CCF) estimates for mutations in tumor clones A, B and C in each biopsy sample (left), and in the Rep-Seq sample (right).

FIG. 6D illustrates the illusion of clonality simulation data, with the number of simulated biopsy samples plotted on the x-axis, and the percentage of variants which incorrectly appear to be Clonal (illusion of clonality) on the y axis (from 100 simulated sample combinations).

FIG. 6E illustrates ctDNA data for Rep-Seq1, with the VAFs plotted (y-axis) for mutations in clones A, B and C.

FIG. 6F illustrates phylogenetic trees for cases Rep-Seq2 and Rep-Seq3, constructed using the Rep-Seq method.

FIG. 6H illustrates the number of non-synonymous variants detected in normal and purity enriched Rep-Seq samples (right). Variant counts are color coded based on either being "shared" (i.e. present in both samples) or "private" (i.e. variant is present in only that sample, and absent from the other).

FIG. 9 provides variant allele frequencies from whole exome sequencing in cases Rep-Seq4 to Rep-Seq10, split by the Ref>Alt base change, and also by frequency (above or below 5% VAF). Base changes associated with FFPE artefact (e.g. C>T, G>A) do not have an elevation in low frequency mutations. These data demonstrate that Rep-Seq generates sequencing data that is equivalent to standard sequencing methods, and that extended periods of formalin fixation do not negatively impact the sequencing of DNA from homogenized residual tumor tissue.

DETAILED DESCRIPTION

Figure 1:
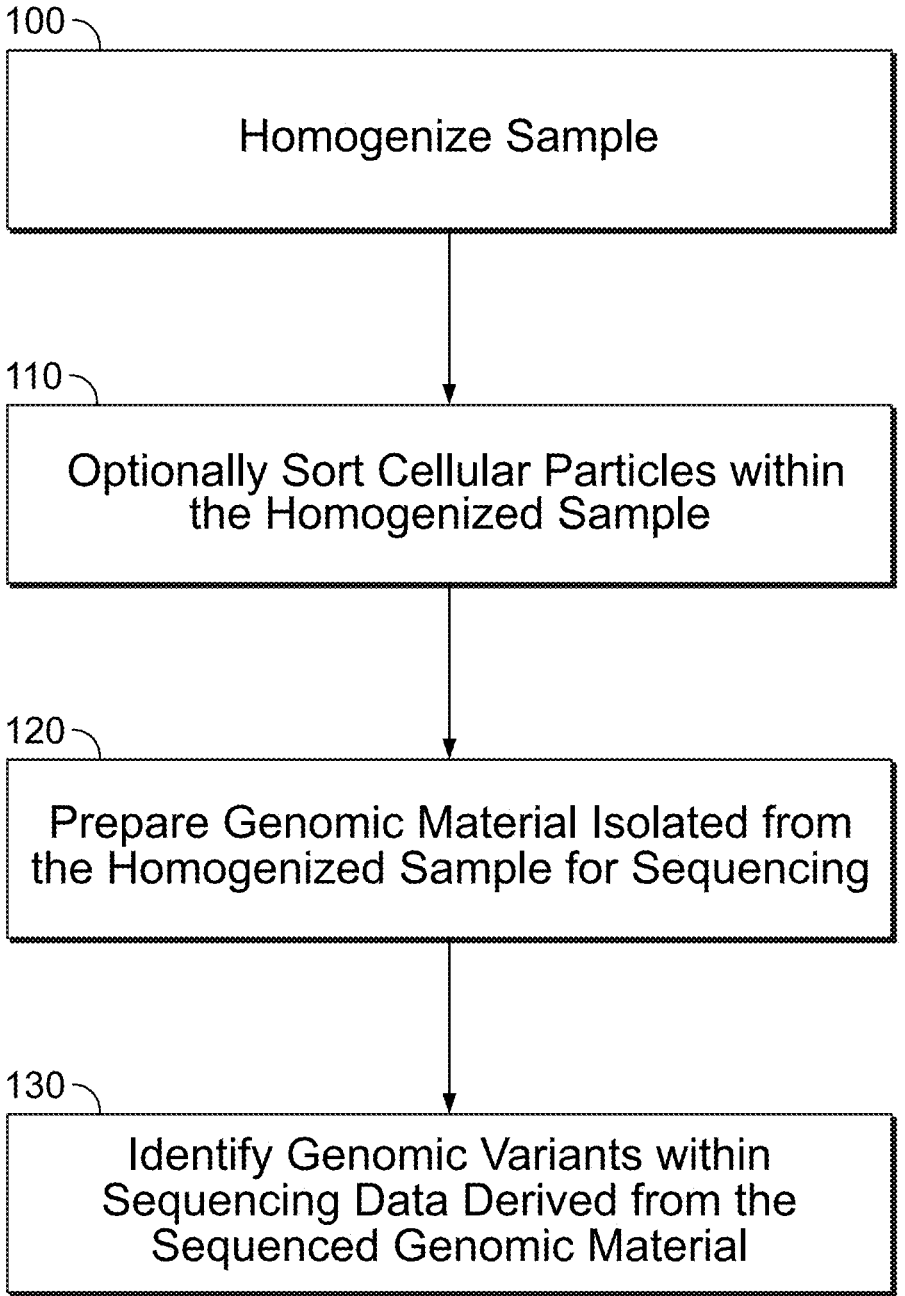
FIG. 1 provides a flowchart setting forth the steps of identifying genetic variants within a homogenized tumor sample.

It should also be understood that, unless clearly indicated to the contrary, in any methods claimed herein that include more than one step or act, the order of the steps or acts of the method is not necessarily limited to the order in which the steps or acts of the method are recited.

As used herein, the singular terms "a," "an," and "the" include plural referents unless context clearly indicates otherwise. Similarly, the word "or" is intended to include "and" unless the context clearly indicates otherwise. The term "includes" is defined inclusively, such that "includes A or B" means including A, B, or A and B.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of" or "exactly one of." "Consisting essentially of," when used in the claims, shall have its ordinary meaning as used in the field of patent law.

The terms "comprising," "including," "having," and the like are used interchangeably and have the same meaning. Similarly, "comprises," "includes," "has," and the like are used interchangeably and have the same meaning. Specifically, each of the terms is defined consistent with the common United States patent law definition of "comprising" and is therefore interpreted to be an open term meaning "at least the following," and is also interpreted not to exclude additional features, limitations, aspects, etc. Thus, for example, "a device having components a, b, and c" means that the device includes at least components a, b and c. Similarly, the phrase: "a method involving steps a, b, and c" means that the method includes at least steps a, b, and c. Moreover, while the steps and processes may be outlined herein in a particular order, the skilled artisan will recognize that the ordering steps and processes may vary.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

As used herein, the term "biological sample," "tissue sample," "specimen" or the like refers to any sample including a biomolecule (such as a protein, a peptide, a nucleic acid, a lipid, a carbohydrate, or a combination thereof) that is obtained from any organism including viruses. Other examples of organisms include mammals (such as humans; veterinary animals like cats, dogs, horses, cattle, and swine; and laboratory animals like mice, rats and primates), insects, annelids, arachnids, marsupials, reptiles, amphibians, bacteria, and fungi. Biological samples include tissue samples (such as tissue sections and needle biopsies of tissue), cell samples (such as cytological smears such as Pap smears or blood smears or samples of cells obtained by microdissection), or cell fractions, fragments or organelles (such as obtained by lysing cells and separating their components by centrifugation or otherwise). Other examples of biological samples include blood, serum, urine, semen, fecal matter, cerebrospinal fluid, interstitial fluid, mucous, tears, sweat, pus, biopsied tissue (for example, obtained by a surgical biopsy or a needle biopsy), nipple aspirates, cerumen, milk, vaginal fluid, saliva, swabs (such as buccal swabs), or any material containing biomolecules that is derived from a first biological sample. In certain embodiments, the term "biological sample" as used herein refers to a sample (such as a homogenized or liquefied sample) prepared from a tumor or a portion thereof obtained from a subject.

As used herein, the term "biomarker" refers to a biological molecule found in blood, other body fluids, or tissues that is a sign of a normal or abnormal process, or of a condition or disease (such as cancer). A biomarker may be used to determine how well the body responds to a treatment for a disease or condition or if the subject is predisposed to a disease or condition. In the context of cancer, a biomarker refers to a biological substance that is indicative of the presence of cancer in the body. A biomarker may be a molecule secreted by a tumor or a specific response of the body to the presence of cancer. Genetic, epigenetic, proteomic, glycomic, and imaging biomarkers can be used for cancer diagnosis, prognosis, and epidemiology. Such biomarkers can be assayed in non-invasively collected biofluids like blood or serum. Several gene and protein based biomarkers have already been used in patient care including but, not limited to, AFP (Liver Cancer), BCR-ABL (Chronic Myeloid Leukemia), BRCA1/BRCA2 (Breast/Ovarian Cancer), BRAF V600E (Melanoma/Colorectal Cancer), CA-125 (Ovarian Cancer), CA19.9 (Pancreatic Cancer), CEA (Colorectal Cancer), EGFR (Non-small-cell lung carcinoma), HER-2 (Breast Cancer), KIT(Gastrointestinal stromal tumor), PSA (Prostate Specific Antigen), S100 (Melanoma), and many others. Biomarkers may be useful as diagnostics (to identify early stage cancers) and/or prognostics (to forecast how aggressive a cancer is and/or predict how a subject will respond to a particular treatment and/or how likely a cancer is to recur).

As used herein, the term "cellular particle" refers to an individual cell or an organelle released from the cell. In some embodiments, the organelle released from the cell is a cell nucleus. In other embodiments, the organelle released from the cell is a cell nucleus containing remnants of cytoplasmic material that may be used to identify the cell of origin of the nucleus. For example, cytokeratin may remain attached to the nucleus and be used as a protein marker for nuclei originating from a tumor cell.

As used herein, the term "clonal mutation" refers to a mutation present in the majority of cells.

As used herein, the term ctDNA" refers to free DNA released from primary tumor cells, circulating tumor cells in the blood circulation system and necrotic or apoptotic tumor cells to the peripheral blood, or any combination thereof.

As used herein, the term "elevated risk" relates to an increased probability than an event will occur compared to another population. In the context of the present disclosure, "a subject at elevated risk of rapid disease progression" refers to a subject (e.g. a human patient) having an increased probability of rapid disease progression due to the presence of one or more mutations, including subclonal mutations as compared to a subject not having such mutation(s).

As used herein, the terms "homogenizing" or "homogenization" refer to a process (such as a mechanical process and/or a biochemical process) whereby a biological sample is brought to a state such that all fractions of the sample are equal in composition. Representative samples (as defined above) may be prepared by removal of a portion of a sample that has been homogenized. A homogenized sample (a "homogenate") is mixed well such that removing a portion of the sample (an aliquot) does not substantially alter the overall make-up of the sample remaining and the components of the aliquot removed is substantially identical to the components of the sample remaining. In the present disclosure the "homogenization" will in general preserve the integrity of the majority of the cells within the sample, e.g., at least 50% of the cells in the sample will not be ruptured or lysed as a result of the homogenization process. In other embodiments, homogenization will preserve the integrity of at least 80% of the cells in the sample. In other embodiments, homogenization will preserve the integrity of at least 85% of the cells in the sample. In other embodiments, homogenization will preserve the integrity of at least 90% of the cells in the sample. In other embodiments, homogenization will preserve the integrity of at least 95% of the cells in the sample. In other embodiments, homogenization will preserve the integrity of at least 96 of the cells in the sample. In other embodiments, homogenization will preserve the integrity of at least 97% of the cells in the sample. In other embodiments, homogenization will preserve the integrity of at least 98% of the cells in the sample. In other embodiments, homogenization will preserve the integrity of at least 99% of the cells in the sample. In other embodiments, homogenization will preserve the integrity of at least 99.9% of cells in the same. The homogenates may be substantially dissociated into individual cells (or clusters of cells) and the resultant homogenate or homogenates are substantially homogeneous (consisting of or composed of similar elements or uniform throughout).

As used herein, the term "lymph node" refers to an oval- or kidney-shaped organ of the lymphatic system, present widely throughout the body including the armpit and stomach and linked by lymphatic vessels. Lymph nodes contain a diverse number of immune cells, including but not limited to B cells and T cells. In some embodiments, lymph nodes may contain hidden tumor cells.

As used herein, the term "neoantigen" is an antigen that is formed by peptides that are normally absent from the proteome of a cell. The term "antigen" is used herein as it is in art and means a molecule or portion thereof that induces the production of antibodies in an organism capable of antibody production. In some embodiments, the term "neoantigen" refers to a class of tumor antigens which arise from tumor-specific mutations in an expressed protein. In some embodiments, the neoantigen can be derived from any cancer, tumor or cell thereof. In some embodiments, the term encompasses both a neoantigenic peptide and a polynucleotide encoding a neoantigenic peptide. Not all antigens can elicit an immune response, thus the term "antigenic" is not synonymous with "immunogenic." Likewise, the term "antigen" is not synonymous with "immunogen." As used herein, the neoantigens that are discovered using the methods of the present disclosure may or may not be immunogenic. In some embodiments, the neoantigens discovered using the methods of the present disclosure are immunogenic. In some embodiments, the neoantigens discovered using the methods of the present disclosure are not immunogenic to one host, e.g., a human host, but can be used to generate antibodies in other hosts to target them therapeutically. In some embodiments, the neoantigens of the present disclosure can be specific for each individual population of cells. For example, a population of cells obtained from one subject may contain neoantigens that are different from neoantigens contained in a population of cells obtained from a different subject. Thus, while the cells' DNA may be identical or nearly identical between two cell populations taken from different subjects, the neoantigens contained in the cell populations could be different. Accordingly, the present disclosure can be applied to methods of personalized medicine.

As used herein, the term "nucleic acid" as used herein, refers to a high-molecular-weight biochemical macromolecule composed of nucleotide chains that convey genetic information. The most common nucleic acids are deoxyribonucleic acid (DNA) and ribonucleic acid (RNA). The monomers from which nucleic acids are constructed are called nucleotides. Each nucleotide consists of three components: a nitrogenous heterocyclic base, either a purine or a pyrimidine (also known as a nucleobase); and a pentose sugar. Different nucleic acid types differ in the structure of the sugar in their nucleotides; DNA contains 2-deoxyribose while RNA contains ribose.

As used herein, the terms "read depth" or "sequencing depth" refer to the number of times a sequence has been sequenced (the depth of sequencing). As an example, read depth can be determined by aligning multiple sequencing run results and counting the start position of reads in non-overlapping windows of a certain size (for example, 100 bp). Copy number variation can be determined based on read depth using methods known in the art. For example, using a method described in Yoon et al., Genome Research 2009 September; 19(9): 1586-1592; Xie et al., BMC Bioinformatics 2009 Mar. 6; 10:80; or Medvedev et al., Nature Methods 2009 November; 6 (11 Suppl): S13-20.

As used herein, the terms "representative sample" and "representative sampling" as used herein refer to a sample (or a subset of a sample) that accurately reflects the components of the entirety and, thus, the sample is an unbiased indication of the entire population. In general, this means that the different types of cells and their relative proportion or percentages within the representative sample or a portion thereof essentially accurately reflects or mimics the relative proportion or percentages of these cell types within the entire tissue specimen, generally a solid tumor or portion thereof. Sampling is the operation of securing portions of an object for subsequent analysis. Representative samples are generated in away that a reasonably close knowledge of the object being studied can be obtained. By contrast, conventional random sampling methods, generally does not give rise to a "representative sample." While the selection of smaller individual sub-samples from a larger sample can be biased based on the regions selected, homogenizing a large sample, e.g., an entire tumor or lymph node, results in spatially segregated elements being homogenously dispersed throughout the sample.

As used herein, the terms "sequencing" or "DNA sequencing" refers to biochemical methods for determining the order of the nucleotide bases, adenine, guanine, cytosine, and thymine, in a DNA oligonucleotide. Sequencing, as the term is used herein, can include without limitation parallel sequencing or any other sequencing method known of those skilled in the art, for example, chain-termination methods, rapid DNA sequencing methods, wandering-spot analysis, Maxam-Gilbert sequencing, dye-terminator sequencing, or using any other modern automated DNA sequencing instruments.

As used herein, the terms "sequence data" or "sequencing data" refer to any sequence information on nucleic acid molecules known to the skilled person. The sequence data can include information on DNA or RNA sequences, modified nucleic acids, single strand or duplex sequences, or alternatively amino acid sequences, which have to converted into nucleic acid sequences. The sequence data may additionally comprise information on the sequencing device, date of acquisition, read length, direction of sequencing, origin of the sequenced entity, neighboring sequences or reads, presence of repeats or any other suitable parameter known to the person skilled in the art. The sequence data may be presented in any suitable format, archive, coding or document known to the person skilled in the art.

As used herein, the term "subclonal mutation" refers to a mutation present in less than 100% of cancer cells, typically less than 50%. A subclonal mutation can be present in the majority of a tumor (i.e. less than 100%, but greater than 50%) or in the minority of the tumor (i.e. less than 50%).

As used herein, the term "tumor" refers to a mass or a neoplasm, which itself is defined as an abnormal new growth of cells that usually grow more rapidly than normal cells and will continue to grow if not treated sometimes resulting in damage to adjacent structures. Tumor sizes can vary widely. A tumor may be solid or fluid-filled. A tumor can refer to benign (not malignant, generally harmless), or malignant (capable of metastasis) growths. Some tumors can contain neoplastic cells that are benign (such as carcinoma in situ) and, simultaneously, contain malignant cancer cells (such as adenocarcinoma). This should be understood to include neoplasms located in multiple locations throughout the body. Therefore, for purposes of the disclosure, tumors include primary tumors, lymph nodes, lymphatic tissue, and metastatic tumors.

As used herein, the term "tumor sample" encompasses samples prepared from a tumor or from a sample potentially comprising or suspected of comprising cancer cells, or to be tested for the potential presence of cancer cells. In some embodiments, the tumor sample may be derived from, for example, a lymph node.

As used herein, the terms "variant" or "genetic variant" refer to an alternative form of a gene, a genomic sequence, or portions thereof. A variant can also be referred to on a protein or RNA level, corresponding to the genomic change. In some embodiments, a variant causes changes of amino acids in a protein sequence but can also impact the function or activity of a protein or cell otherwise, such as in terms of RNA splicing, translation, or on other levels of transcription or translation regulation. "Variant" can also refer to a polypeptide in which the sequence differs from the sequence most prevalent in a population at a position that does not change the amino acid sequence of the encoded polypeptide (i.e., a conserved change). Genetic variant polypeptides can be encoded by a risk haplotype, encoded by a protective haplotype, or can be encoded by a neutral haplotype. Genetic variant polypeptides can be associated with risk, associated with protection, or can be neutral. Non-limiting examples of genetic variants include frameshift, stop gained, start lost, splice acceptor, splice donor, stop lost, missense, splice region, synonymous and copy number variants. Non-limiting types of copy number variants include deletions and duplications.

Generation of Representative Samples for Sequencing

Input Samples and Homogenization

In some embodiments, a tumor sample, lymph node sample, blood sample, and/or other tissue sample (collectively the "input sample") is homogenized (step 100) by placing the sample into a mechanical shearing apparatus, e.g. a blender or an ultra sonicator.

In some embodiments, the input sample comprises a representative sample of cells derived from a tumor sample, lymph node sample, blood sample, or any combination thereof. In some embodiments, the input sample is derived from a human patient or mammalian subject (i) diagnosed with cancer, (ii) suspected of having cancer, (iii) at risk of developing cancer; (iv) at risk of relapse or recurrence of cancer; and/or (v) suspected of having cancer recurrence. In other embodiments, the input sample is derived from a healthy human patient or mammalian subject.

In some embodiments, the representative samples are obtained by homogenization (step 100) of large volumes or quantities of a tumor sample (such as a clinical tumor sample) or lymph node obtained from a subject. For example, a whole tumor or a substantial portion thereof may be used as the input material from which the representative sample is generated. In some embodiments, at least 40% of a tumor or lymph node (or the portion thereof that remains after removal of portions used for other diagnostic tests, such as removal of a portion usable for preparation of conventional FFPE samples) is utilized for homogenization. In other embodiments, at least 50% of a tumor or lymph node is utilized for homogenization. In other embodiments, at least 60% of a tumor or lymph is utilized for homogenization. In other embodiments, at least 70% of a tumor or lymph node is utilized for homogenization. In other embodiments, at least 80% of a tumor or lymph is utilized for homogenization. In other embodiments, at least 90% of a tumor or lymph node is utilized for homogenization. In other embodiments, at least 91% of a tumor or lymph node is utilized for homogenization. In other embodiments, at least 92% of a tumor or lymph node is utilized for homogenization. In other embodiments, at least 93% of a tumor or lymph node is utilized for homogenization. In other embodiments, at least 94% of a tumor or lymph node is utilized for homogenization. In other embodiments, at least 95% of a tumor or lymph node is utilized for homogenization. In other embodiments, at least 96% of a tumor or lymph node is utilized for homogenization. In other embodiments, at least 97% of a tumor or lymph node is utilized for homogenization. In other embodiments, at least 98% of a tumor or lymph node is utilized for homogenization. In other embodiments, at least 99% of a tumor or lymph node is utilized for homogenization. In yet other embodiments, the entire tumor, an entire lymph node, or an entire population of lymph nodes (or the portion thereof that remains after removal of portions used for other diagnostic tests, such as removal of a portion usable for preparation of conventional FFPE samples), is used for homogenization.

The representative sample may be generated from an intact tumor biopsy sample from a solid tumor. In some embodiments, the biopsy sample comprises at least about 100 to about 200 cells. In other embodiments, the biopsy sample comprises at least about 200 to about 1,000 cells. In yet other embodiments, the biopsy sample comprises at least about 1,000 to about 5,000 cells. In further embodiments, the biopsy sample comprises at least about 10,000 to about 100,000 cells. In even further embodiments, the biopsy sample comprises at least about 100,000 to about 1,000,000 or more cells. In some embodiments, the cells are obtained from spatially distinct regions of the tumor. In another embodiment, the representative examples disclosed herein are obtained by homogenization of one or more putative normal tissue specimens, e.g., derived from a patient or mammalian subject at risk of developing cancer, including those at risk of developing cancer because of a genetic mutation or prior cancer. As used herein, the term "spatially distinct" refers to elements that are distributed in different regions of a space. In one embodiment, the tumor biopsy samples used to generate the representative sample are taken from different regions of the tumor sample. For example, proximal versus distal regions of the tumor, different faces of the tumor, different layers of the tumor, etc. in an effort to capture the diversity within the whole tumor.

In some embodiments, a tumor sample, lymph node sample, or other tissue sample is homogenized by placing the sample into a mechanical shearing apparatus, e.g. a blender or an ultra sonicator. In some embodiments, the homogenization produces a range of tissue fragments from thousands to hundreds of cells each. In some embodiments, the median of the tissue fragment size is inversely correlated to the energy of the blender (or other suitable device); such that at high energy the tissue fragments are very small. In some embodiments, the component of the tissue that is most relevant to blender energy is collagen content, as the dermis requires significant energy for complete disassociation. In some embodiments, the time of blending is also important; however, the most effective clinical application requires that the whole tumor be disassociated in a matter of minutes. Once the time of blending is fixed, the energy required to reach tumor disassociation under the desired time limit can readily be determined. Other methods of preparing tumor samples or lymph node samples are disclosed in PCT Publication No. WO/2017/07976 and in United States Patent Publication No. 2018/0320229, the disclosures of which are hereby incorporated by reference herein in their entireties. Aliquots can be removed from the homogenized sample for use in the preparing genomic material for sequencing, such as described further herein.

Following sufficient mechanical shearing to disassociate the tumor, lymph node, and/or other tissue sample, all the subpopulations of tumor cells that were originally spatially segregated within the original sample are distributed throughout the newly homogenized sample. That is, as a result of homogenizing a tumor, one or more lymph nodes, blood, or any combination thereof, any heterogeneity of cells within the tumor is substantially homogeneously (uniformly) distributed within the resultant homogenate or a portion or fraction thereof, such that the homogenate (or any fraction thereof) substantially homogeneously expresses the heterogeneity of the tumor and/or lymph node sample which was the input. By homogenizing tumors and/or lymph nodes to generate a sample (or homogenate) that is representative of the tumor in its entirety, it is possible, in some embodiments, to characterize the landscape (such as the heterogeneity) of the tumor, such as by sequencing the genetic variants present within the homogenized sample, as described herein.

In some embodiments, the input sample is derived from a sufficient quantity of histological sections and/or biopsy samples, e.g. obtained from multiple histological sections and/or multiple biopsy samples. In some embodiments, the input sample derived from histological sections and/or biopsy samples comprise at least 0.2 micrograms of genomic material. In some embodiments, the input sample derived from histological sections and/or biopsy samples comprise at least 0.3 micrograms of genomic material. In some embodiments, the input sample derived from histological sections and/or biopsy samples comprise at least 0.4 micrograms of genomic material. In some embodiments, the input sample derived from histological sections and/or biopsy samples comprise at least 0.5 micrograms of genomic material. In other embodiments, the input sample derived from histological sections and/or biopsy samples comprise at least 1 microgram of genomic material. In other embodiments, the input sample derived from histological sections and/or biopsy samples comprise at least 5 micrograms of genomic material. In other embodiments, the input sample derived from histological sections and/or biopsy samples comprise at least 10 micrograms of genomic material.

In some embodiments, the quantity of genomic material within the input sample for use with the disclosed methods is at least 10 times greater than a quantity of material within an input sample for use with traditional sequence capture methods. In some embodiments, the quantity of genomic material within the input sample for use with the disclosed methods is at least 50 times greater than a quantity of material within an input sample for use with traditional sequence capture methods. In some embodiments, the quantity of genomic material within the input sample for use with the disclosed methods is at least 100 times greater than a quantity of material within an input sample for use with traditional sequence capture methods. In some embodiments, the quantity of genomic material within the input sample for use with the disclosed methods is at least 250 times greater than a quantity of material within an input sample for use with traditional sequence capture methods. In some embodiments, the quantity of genomic material within the input sample for use with the disclosed methods is at least 500 times greater than a quantity of material within an input sample for use with traditional sequence capture methods. In some embodiments, the quantity of genomic material within the input sample for use with the disclosed methods is at least 1000 times greater than a quantity of material within an input sample for use with traditional sequence capture methods. In some embodiments, the quantity of genomic material within the input sample for use with the disclosed methods is about 1000 times greater than a quantity of material within an input sample for use with traditional sequence capture methods.

Subsequent Processing of the Homogenized Sample

In some embodiments, the homogenized sample is further processed prior to downstream analysis. For example, cells and or genomic material may be separated from the homogenized sample, such as by filtering the homogenate. In some embodiments, the homogenate is filtered with a set of cell strainers of different sizes (e.g. about 20 μm, about 10 um, etc.). In some embodiments, a metal mesh is used to remove large tissue fragments before filtration with cell strainers. In some embodiments, the obtained filtered sample is predominantly composed of single cells (some small cell aggregated such as doublets) that can be stained for with desired markers.

In some embodiments, cells within the homogenized sample, or filtered homogenized sample, are lysed to release cellular components. For example, cells may be lysed using a French press or similar type of lysis apparatus, microfluidizers, grinding, milling, chemical or enzymatic lysis, and/ or using other techniques known in the art. In some embodiments, membrane lipids and proteins (include histones) are removed from the sample containing the cellular components (e.g. by adding surfactants or enzymes (proteases)). In addition, RNA may be removed from the sample containing the cellular components (e.g. with an enzyme such as an RNase).

The homogenized samples (or filtered homogenized samples) may be further dissociated and/or treated to provide dissociated cells, nuclei, and/or small tissue aggregates. In general, there are three primary methods for tissue dissociation including enzymatic dissociation, chemical dissociation and mechanical dissociation or any combination thereof. The selection of a method for dissociation is usually made based on the tissue type and tissue origin.

Enzymatic dissociation is the process of using enzymes to digest tissue pieces thereby releasing cells from tissue. Many different types of enzymes may be used in this process and, as the skilled artisan will appreciate, certain enzymes are more effective with certain tissue types. The skilled artisan will also appreciate any enzymatic dissociation process may use one or more enzymes in combination with each other, or one or more enzymes in combination with other chemical and/or mechanical dissociation methods. Examples of suitable enzymes include, but are not limited to, collagenase, trypsin, elastase, hyaluronidase, papain, DNase I, neutral protease, and trypsin inhibitor.

Collagenase is a proteolytic enzyme used to digest proteins found in the extracellular matrix. Unique to enzymatic proteases, collagenase can attack and degrade the triple-helical native collagen fibrils that are commonly found in connective tissue. There exist four basic collagenase types, namely: Type 1, which is suitable for use in epithelial, liver, lung, fat and adrenal tissue cell specimens; Type 2, which is suitable for use in heart, bone, muscle, thyroid and cartilage tumor originating tissues given its high proteolytic activity; Type 3, which is suitable for use in mammary cells given its low proteolytic activity; and Type 4: which is suitable for islets and other research protocols where receptor integrity is important, given its tryptic activity.

Trypsin is described as a pancreatic serine (an amino acid) protease that has specificity for peptide bonds that involve the carboxyl group of arginine and lysine amino acids. It is considered one of the most highly specific proteases. Trypsin alone is not usually effective for tissue dissociation because it shows minimal selectivity to extracellular proteins. It is usually combined with other enzymes such as collagenase or elastase.

Elastase is another pancreatic serine protease, which has specificity for peptide bonds that are next to neutral amino acids. It is unique among proteases in its ability to hydrolyze native elastin. Elastase can also be found in blood components and bacteria. In some embodiments, it is suitable for isolation of Type II cells from lung tissue.

Hyaluronidase is a polysaccharidase, this enzyme is often used for dissociation of tissues, typically when combined with a more crude protease such as collagenase. It has affinity for bonds found in just about all connective tissues.

Papain is a sulfhydryl protease, it has wide specificity and so can degrade most protein substrates more thoroughly than pancreatic proteases, i.e. trypsin or elastase. Papain is frequently used to isolate neuronal materials from tissues.

Deoxyribonuclease I (DNase I) is frequently included in enzymatic cell isolation procedures to digest nucleic acids that leak into the dissociation medium and can increased viscosity and recovery problems. Without wishing to be bound by any particular theory, it is believed that DNaseI will not damage intact cells.

Neutral protease, such Dispase® (available from Worthington Biochemical), is a bacterial enzyme with mild proteolytic activity, Dispase® is useful for isolating primary and secondary cell cultures because of its ability to maintain cell membrane integrity. It has been found to more efficiently dissociate fibroblast-like cells as compared to epithelial-like cells. It is inhibited by EDTA.

A trypsin inhibitor is derived mainly from the soybean, it inactivates trypsin, and so is sometimes used for specific cell isolation protocols.

Chemical dissociation takes advantage of the fact that cations participate in the maintenance of intracellular bonds and the intracellular matrix. By introducing EDTA or EGTA, which binds these cations, the intercellular bonds are disrupted, thereby allowing for dissociation of the tissue structures.

In some embodiments, DNA may be isolated, extracted, or purified by means known to those of ordinary skill in the art. For example, DNA may be extracted via ethanol precipitation or phenol-chloroform extraction followed by centrifugation to form a pellet. In some embodiments, the DNA may be isolated or extracted on a solid phase column. In some embodiments, the DNA may be isolated or extracted using nucleic acid-binding beads. In some embodiments, the DNA may be isolated or extracted by selective passage through a porous matrix based on physical, chemical, or electrical properties.

The extracted DNA (genomic material) may be dissolved in a buffer, e.g. an alkaline buffer, and introduced as the input sample for sequencing, as explain further herein.

Optional Sorting of Cells Within the Homogenized Sample

In some embodiments, the homogenized sample from step 100, is further sorted prior to downstream processing (step 110). In some embodiments, sorting is effectuated using one or more biomarkers present on the cell. In some embodiments, the dissociated cells and/or nuclei are labelled or stained prior to evaluating a homogenized sample by flow cytometry so that different cell types can be identified. The label or stain can be any detectable label or reporter moiety that can identify different cell types by flow cytometry, for example a fluorescent label. For example, a homogenized sample may be first stained for the presence of one or more biomarkers, and then flow cytometry may be utilized to sort the cells based on whether the cells are stained or unstained. In some embodiments, the homogenized sample is contacted with one or more detection probes, which may be visualized by applying one or more detection reagents (see, for example, PCT Publication No. WO/2017/085307, the disclosure of which is hereby incorporated by reference herein in its entirety). For example, in some embodiments, the detection probes utilized are specific for immune cell markers. By way of a further example, the cells may be stained for the presence of one or more biomarkers selected from CD3, CD4, CD8, CD25, CD163, CD45LCA, CD45RA, CD45RO, PD-1, TIM-3, LAG-3, CD28, CD57, FOXP3, EPCAM, and CK8/18.

In some embodiments, sorting is achieved using a sized-based sorting procedure. In some embodiments, a sized-based sorting step sorts dissociated cellular particles into a first cellular particle population and a second cellular particle population, wherein the first cellular particle population is enriched with tumor cells and wherein the second cellular particle population is enriched with normal cells. In some embodiments, the cellular particles are cells and whereby normal cells have an average diameter of less than 12 μm and whereby tumor cells have an average diameter of greater than 12 μm. In some embodiments, a sized-based sorting step sorts dissociated cellular particles into a first population of nuclei and a second population of nuclei, wherein the first population of nuclei is enriched with tumor and wherein the second population of nuclei is enriched with normal nuclei. In some embodiments, the normal nuclei have an average diameter of less than 8.5 μm and the tumor nuclei have an average diameter of greater than 8.5 μm. In some embodiments, the sorting of the cellular particles is accomplished with a microfluidic device. In some embodiments, sized-based staining does not require a staining step. Other methods of sized-bases sorting are described in PCT Publication No. WO/2018/189040, the disclosure of which is hereby incorporated by reference herein in its entirety.

Preparation of Genomic Material for Sequencing

Following the optional sorting of the genomic material, the genomic material is then prepared for sequencing (step 120). Methods of preparing genomic material for sequencing are described in United States Patent Publication No. 2018/0320229, the disclosure of which is hereby incorporated by reference herein in its entirety. In some embodiments, the genomic material is fragmented, to provide a fragmented genomic sample. In some embodiments, fragmentation of the genomic material is followed by repairing or "polishing" the ends of the fragmented genomic material. In some embodiments, the fragmented nucleic acid sample (e.g., fragmented genomic DNA, cDNA, etc.) is modified by ligation to adapters on one or both of the 5' and 3' ends. The genomic materials is then denatured to separate complementary DNA strands according to procedures known to those of ordinary skill in the art.

The denatured genomic material is then subjected to a hybridization reaction, where the hybridization reaction mixture comprises, for example, DNA capture probes complementary in nucleic acid sequence to the target within the genomic material, Cot1 fraction blocking DNA (to block nonspecific hybridization) and blocking oligonucleotides (step 200). The DNA capture probes may be biotinylated for subsequent immobilization using streptavidin coated beads or surfaces or affixed directly to solid supports such as microarrays. Following hybridization, non-targeted and unbound nucleic acids are washed from the solid support and the bound, targeted nucleic acids are eluted from the microarray or capture beads or capture surface following protocols known in the art. In some embodiments, following hybridization of the genomic material with biotinylated DNA capture probes, streptavidin coated beads are incubated with the hybridized genomic material such that the hybridized genomic material is immobilized via a streptavidin-biotin bond and any non-targeted genomic material is removed by washing (bead capture) (step 210). Captured genomic material is then eluted and provided for sequencing or the captured genomic material is first amplified prior to sequencing.

Sequencing of Prepared Genomic Material

Sequencing may be performed according to any method known to those of ordinary skill in the art (step 220). In some embodiments, sequencing methods include Sanger sequencing and dye-terminator sequencing, as well as next-generation sequencing technologies such as pyrosequencing, nanopore sequencing, micropore-based sequencing, nanoball sequencing, MPSS, SOLiD, Illumina, Ion Torrent, Starlite, SMRT, tSMS, sequencing by synthesis, sequencing by ligation, mass spectrometry sequencing, polymerase sequencing, RNA polymerase (RNAP) sequencing, microscopy-based sequencing, microfluidic Sanger sequencing, microscopy-based sequencing, RNAP sequencing, tunneling currents DNA sequencing, and in vitro virus sequencing. See WO2014144478, WO2015058093, WO2014106076 and WO2013068528, each of which is hereby incorporated by reference in its entirety.

In some embodiments, sequencing can be performed by a number of different methods, such as by employing sequencing by synthesis technology. Sequencing by synthesis according to the prior art is defined as any sequencing method which monitors the generation of side products upon incorporation of a specific deoxynucleoside-triphosphate during the sequencing reaction (Hyman, 1988, Anal. Biochem. 174:423-436; Rhonaghi et al., 1998, Science 281:363-365). One prominent embodiment of the sequencing by synthesis reaction is the pyrophosphate sequencing method. In this case, generation of pyrophosphate during nucleotide incorporation is monitored by an enzymatic cascade which results in the generation of a chemo-luminescent signal. The 454 Genome Sequencer System (Roche Applied Science cat. No. 04 760 085 001), an example of sequence by synthesis, is based on the pyrophosphate sequencing technology. For sequencing on a 454 GS20 or 454 FLX instrument, the average genomic DNA fragment size is in the range of 200 or 600 bp, respectively, as described in the product literature.

In some embodiments, a sequencing by synthesis reaction can alternatively be based on a terminator dye type of sequencing reaction. In this case, the incorporated dye deoxynucleotriphosphates (ddNTPs) building blocks comprise a detectable label, which is preferably a fluorescent label that prevents further extension of the nascent DNA strand. The label is then removed and detected upon incorporation of the ddNTP building block into the template/primer extension hybrid for example by using a DNA polymerase comprising a 3-5' exonuclease or proofreading activity.

In some embodiments, sequencing is performed using a next-generation sequencing method such as that provided by Illumina, Inc. (the "Illumina Sequencing Method"). Without wishing to be bound by any particular theory, the Illumina next-generation sequencing technology uses clonal amplification and sequencing by synthesis (SBS) chemistry to enable rapid, accurate sequencing. The process simultaneously identifies DNA bases while incorporating them into a nucleic acid chain. Each base emits a unique fluorescent signal as it is added to the growing strand, which is used to determine the order of the DNA sequence.

Sequencing Data Set

Following sequencing (step 220), the sequencing data may be analyzed such that a plurality of genetic variants may be identified, i.e. genetic variants may be identified within the sequencing data derived from sequencing a homogenized sample. In some embodiments, the genetic variants identified may be clonal or sub-clonal. In some embodiments, Mutect is used to detect variants within sequencing data (see software.broadinstitute.org; and see also US Patent Publication No. 2015/0178445, the disclosures of which are hereby incorporated by reference herein in their entireties).

In some embodiments, neoantigens are derived from the identified genetic variants (step 300). In some embodiments, the derivation of neoantigens enables drug discovery, vaccine generation, and/or CAR-T cell engineering (step 301). For example, Ott et. al. "An immunogenic personal neoantigen vaccine for patients with melanoma," Nature, Vol. 000, 00 Month 2017, doi:10.1038/nature22991 (the disclosure of which is hereby incorporated by reference herein in its entirety), describes a process through which a vaccine is generated which targets neoantigens. Similarly, Sahin et. al., "Personalized RNA mutanome vaccines mobilize poly-specific therapeutic immunity against cancer," Nature, Vol. 000, 00 Month 2017, doi:10.1038/nature23003 (the disclosure of which is incorporated by reference herein in its entirety) describes an RNA-based poly-neoepitope approach to mobilize immunity against a spectrum of cancer mutations in humans. As such, in some embodiments, a vaccine may be generated based on one or more neoantigens derived after sequencing a homogenized tumor sample in accordance with the processes described herein. In some embodiments, the method further comprises administering an effective amount of the vaccine to a subject.

In other embodiments, a ctDNA monitoring panel may be developed based on the identified genetic variants (step 310). In some embodiments, the ctDNA panel may be used to monitor for genetic variants may be result in distant metathesis (step 311).

In yet other embodiments, a clonal structure may be computed based on the identified genetic variants (step 320). In some embodiments, the computed clonal structure may be used to assess the separation between truncal variants and sub-clonal variants (step 321).

EXAMPLES

Figure 4A:
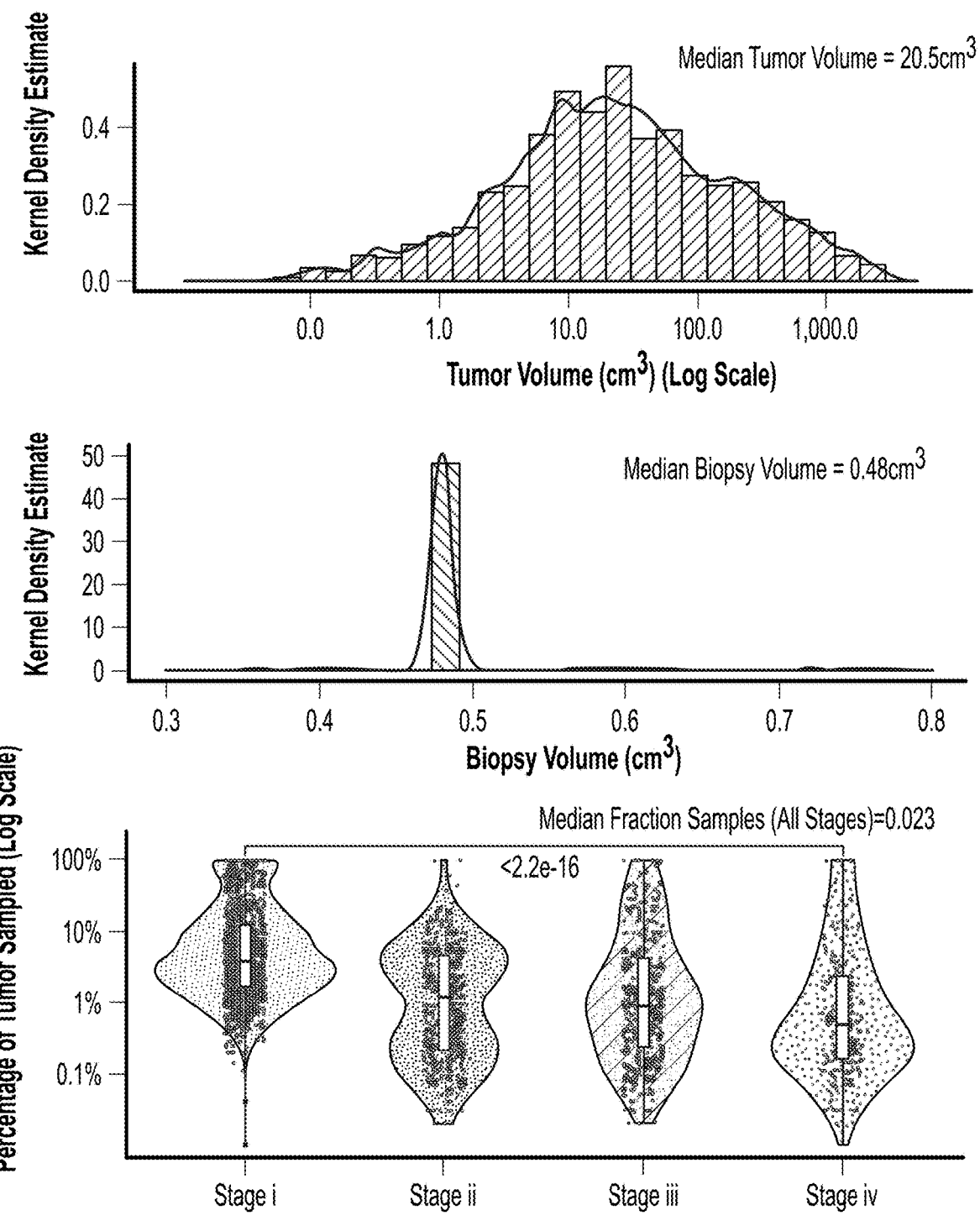
FIGS. 4A-4F illustrate current tumor sequencing methods lead to under-sampling, which can be resolved through a wider sampling frame.
Figure 4B:
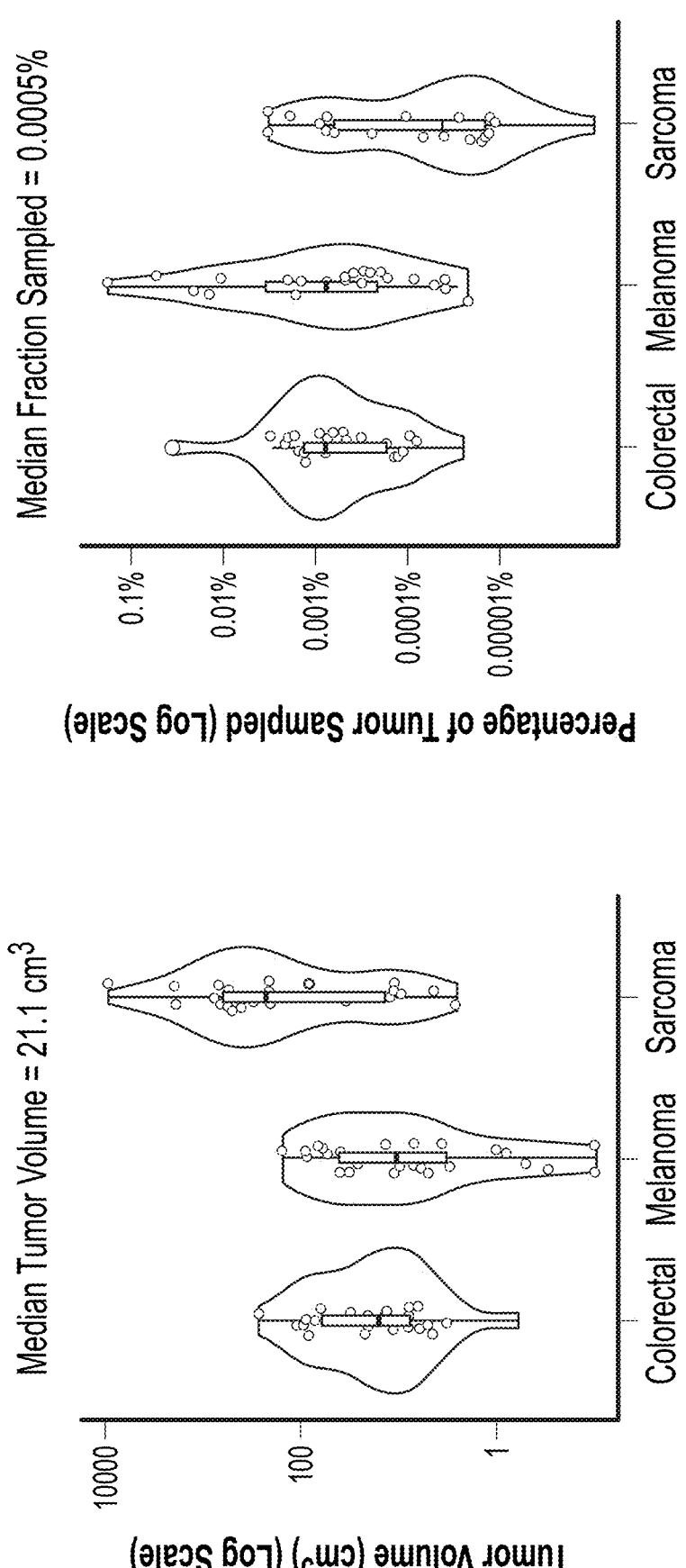

Current tumor sequencing approaches are hindered by physical sampling bias, with input tissue being drawn from only a narrow spatial frame, that will miss expanding subclones in other distant locations. This is a problem that cannot be resolved through excess sequencing depth. To examine the extent of this issue, we conducted analysis of pan-cancer sequencing data from the cancer genome atlas, which revealed that current protocols sample on average only 2.3% of the tumor mass (median value for all stages, n=1,667 samples), decreasing to 0.5% for stage IV tumors (median value, n=181) (FIG. 4A). We further investigated this pattern within a routine clinical context, through audit of randomly selected cases undergoing molecular profiling as part of standard care within a major cancer treatment center (see methods). This revealed a median tumor sampling proportion of only 0.0005% (n=76 cases) (FIG. 4B), reflecting the minimal input material available from standard pathology tumor slides. The remaining 99.9%+ of tumor tissue is left unsampled for molecular profiling purposes, leading to a high level of under-sampling. The pitfalls of utilizing a non-representative sampling method are well documented in the 'Theory of Sampling' developed by Pierre Gy[1], and have been practically demonstrated across multiple fields, ranging from food contamination, to electoral polling and the mining industry[2-4]. In the case of tumor sequencing, this bias arises within the context of intratumor heterogeneity as a well-documented feature of cancer[5-7], combined with the increasing utility of molecular profiling as a tool to stratify patients for targeted or immunotherapy treatments[8]. Failure to address this issue risks undermining the clinical utility of genomic medicine in cancer; through a reduced sensitivity to detect prognostic markers or neoantigen targets for immunotherapy, a lack of reproducibility in sequencing results between biopsies and mis-assignment of subclonal variants as clonal due to biased variant allele frequency values. A frequently proposed solution is to conduct multi-region sampling, which while possible in a research setting[5] is likely too expensive and labor intensive for wide-scale clinical practice. Furthermore, the recurrent question of 'how many biopsies should be taken' is unanswerable due to the high variability in tumor heterogeneity between patients. We hypothesized a new sampling methodology could be implemented to circumvent these limitations, through utilizing residual surgical material to create a wider more representative sampling frame, leading to improved results without the need for increased sequencing depth, or for multiple samples to be profiled per tumor.

Figure 4C:
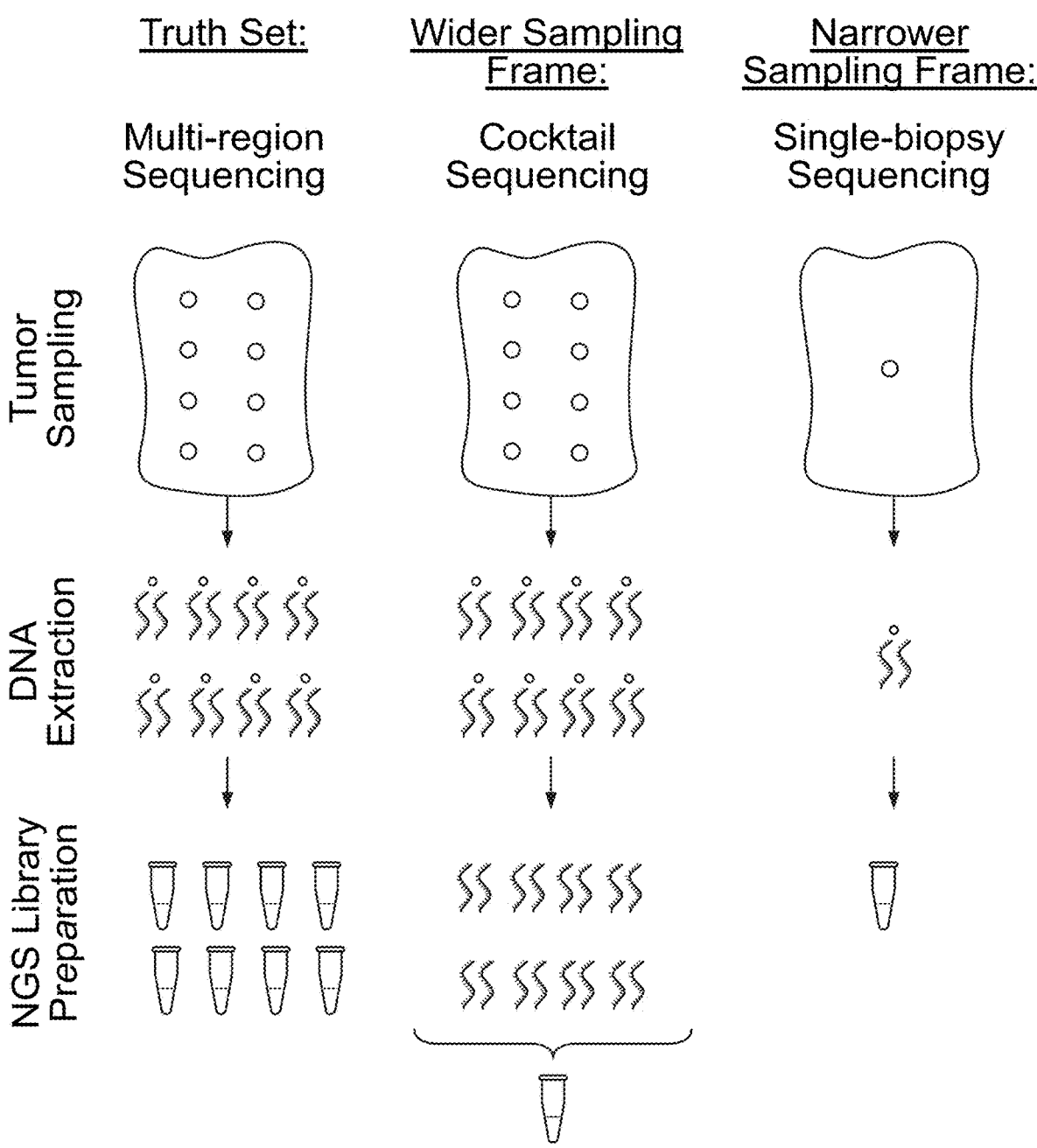
Figure 4D:
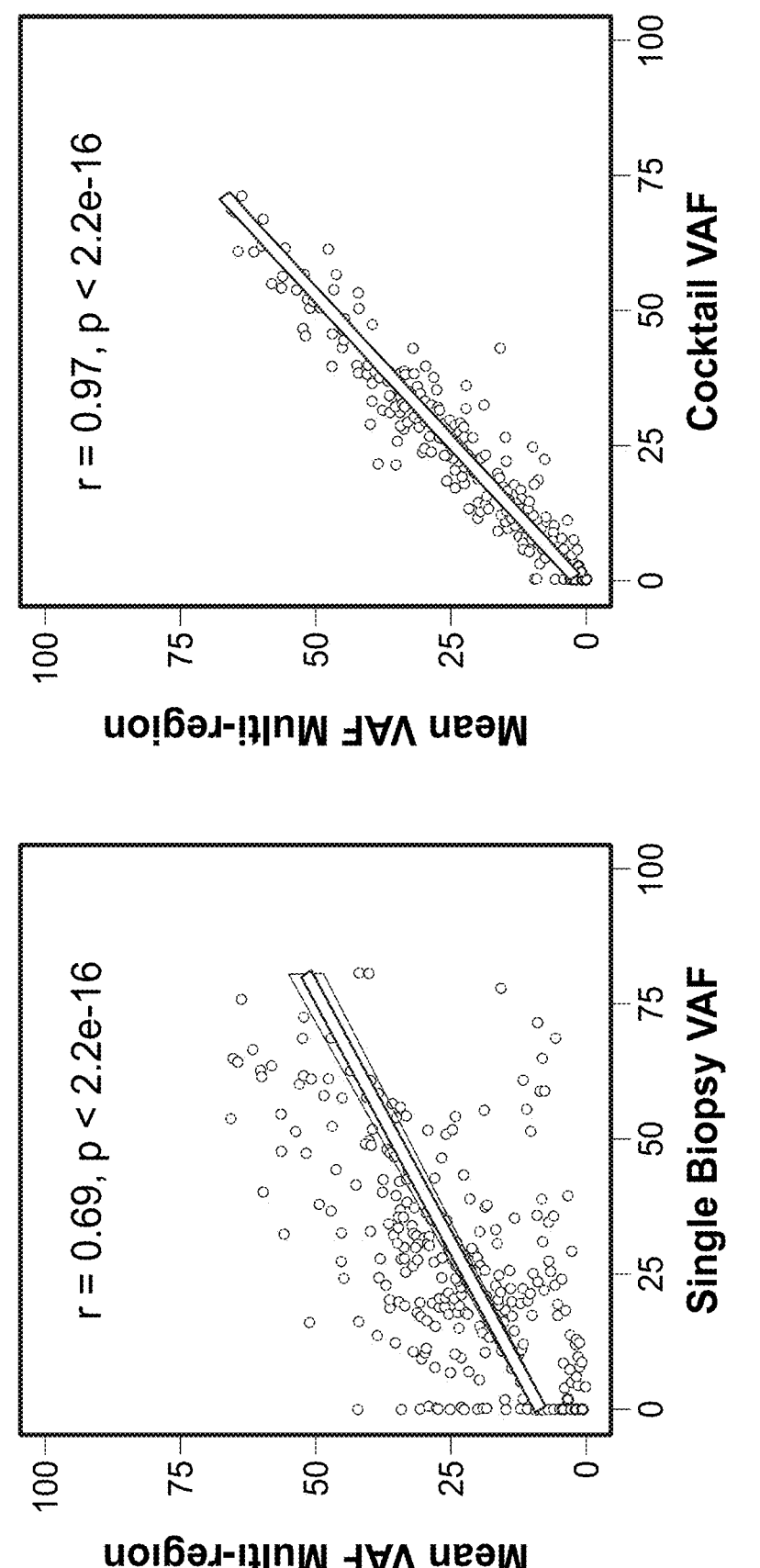
Figure 4E:
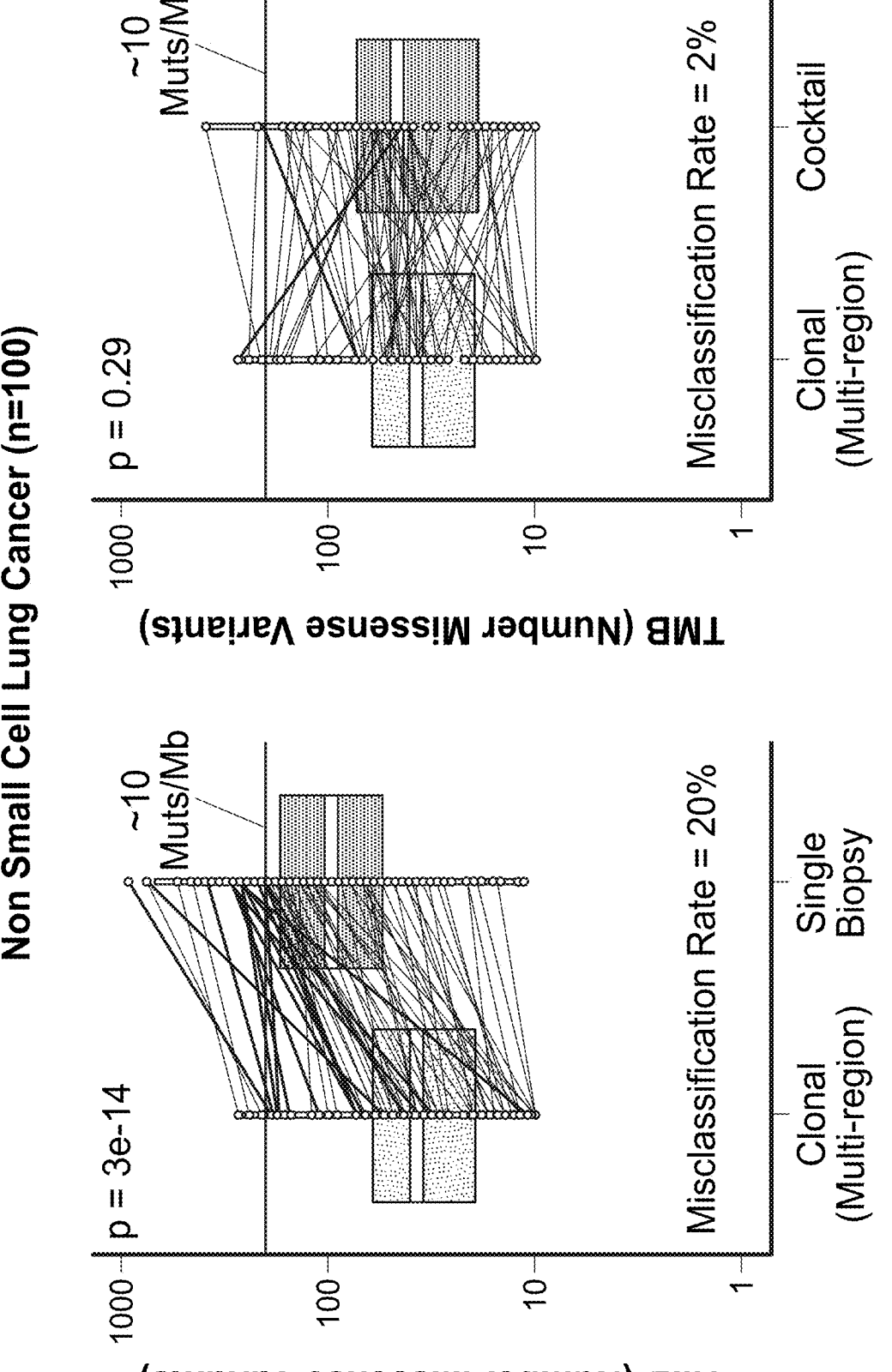
Figure 4F:
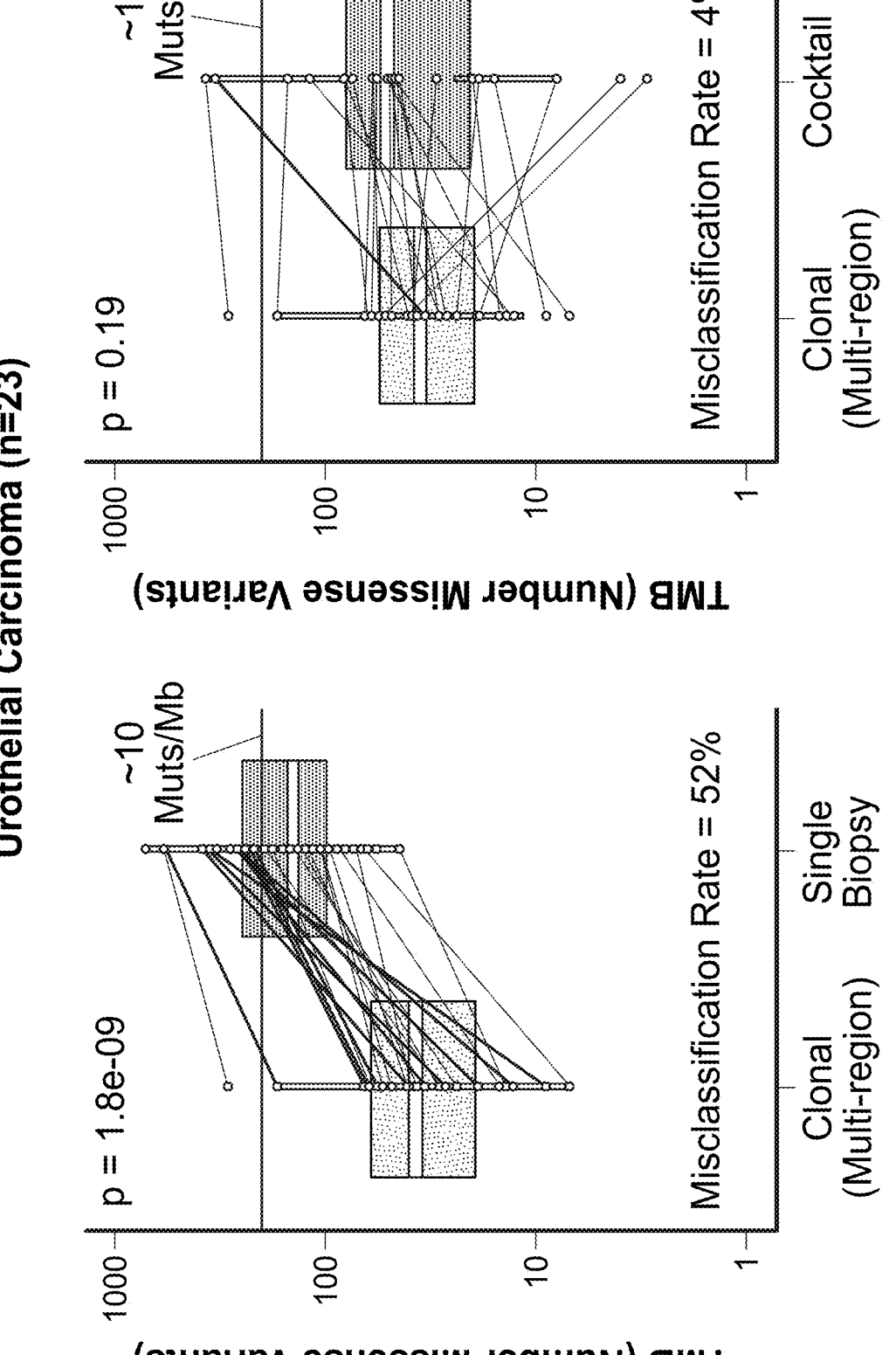

To first test this hypothesis, we conducted a pilot experiment, widening the sampling frame by pooling extracted DNA from n=1,184 multi-region biopsies, from n=79 primary solid tumors, to create "cocktail" solutions per tumor (FIG. 4C). Pooled cocktail samples were subject to next generation sequencing (median depth=674×), and mutation calls compared to previously generated single biopsy (reflecting current clinical practice, median depth=608×) and multi-region biopsy (truth-set) data (median depth=612×). All samples were processed through an identical protocol (see methods). Across all 79 tumors the cocktail samples discovered a median of 100% (range [30%-100%]) of the truth-set mutations, as compared to single biopsies which achieved a median discovery rate of only 73% [15%-100%], supporting the hypothesis that a wider sampling frame leads to improved sensitivity to detect variants (p=6.6×10⁻¹¹, paired Wilcoxon test, FIGS. 4E and 4F). In addition, variant allele frequencies (VAFs) derived from cocktail samples demonstrated a strong correlation with true VAF values from multi-region sequencing (r=0.97), a superior correlation versus that achieved by single biopsy sampling (r=0.69) (FIG. 4D). This suggests a wider sampling frame provides a more accurate estimation of true cellular mutational prevalence across the entire tumor mass, an important consideration for both prognostic and predictive biomarkers.

Figure 5A:
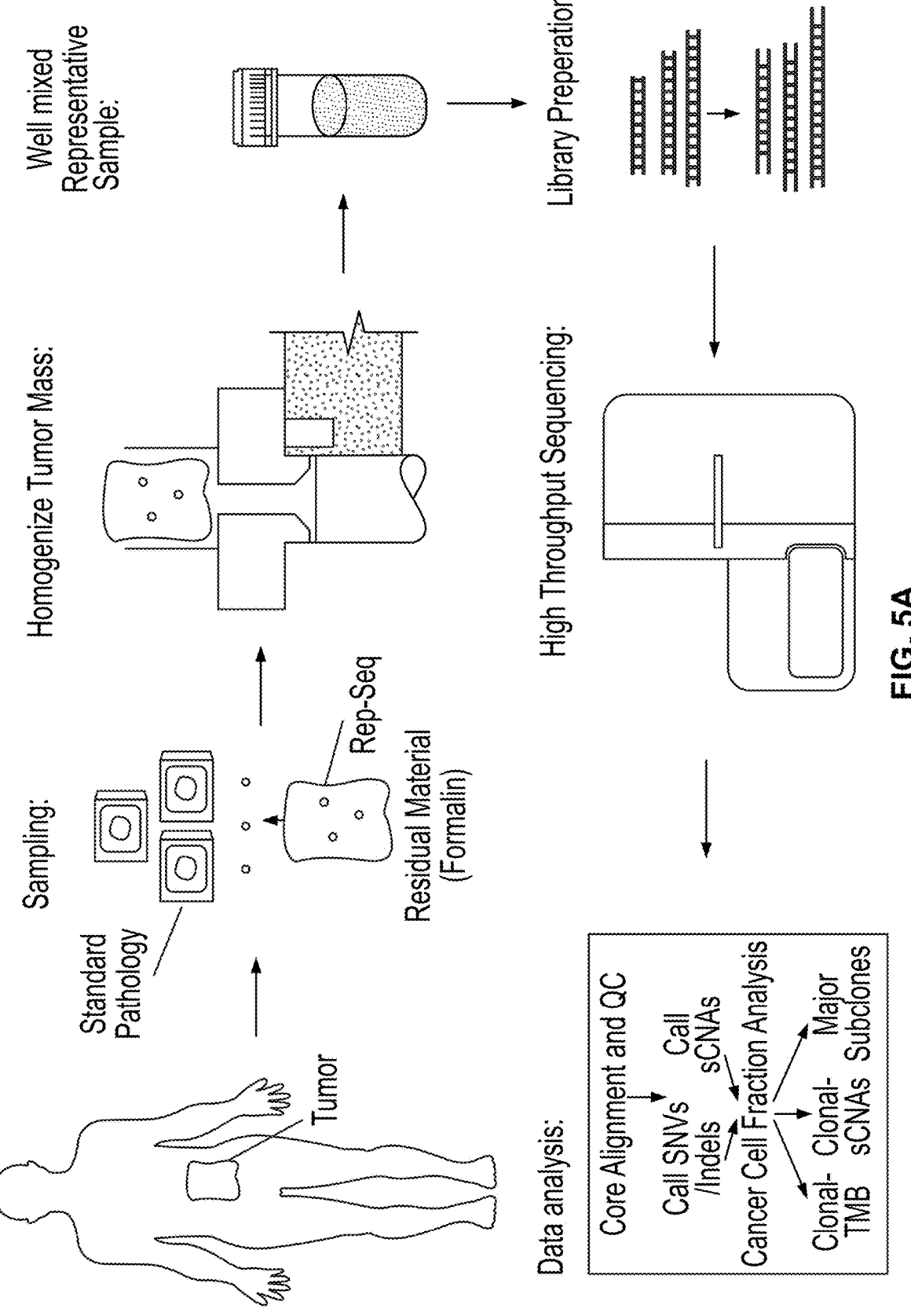

Based on these pilot results, we next sought to develop a novel tumor sampling methodology, allowing sequencing input material to be drawn from the widest possible sampling frame. Here we demonstrate a new method termed "Representative Sequencing" (Rep-Seq), which comprises homogenization of solid tumor masses into well-mixed solutions, coupled with next-generation sequencing (FIG. 5A). Tumor masses were sourced as the entire residual tumor material not taken for pathology assessment following surgery, material which would otherwise have been treated as clinical waste and destroyed. Residual samples represented on average 54.8% of the total tumor volume and provided on average 223.5 g of tissue per tumor (based on our pilot cohort of cases, see Table S1). These values are a significant increase versus the average of 0.0006% sampled, and 0.0001 g of tumor tissue, currently used as the sampling frame in standard molecular profiling approaches. Following dissection of the formalin fixed residual tumor tissue away from the surrounding normal, the residual tumor mass is homogenized into a representative solution.

From this well-mixed solution, samples are drawn for DNA extraction, library preparation and sequencing (FIG. 5A). Rep-Seq was implemented on a proof of concept basis in 11 tumors, from 4 different cancer types (Table S1). The first tumor processed was Rep-Seg1, a large clear cell renal cell carcinoma (ccRCC) tumor (17 cm maximal dimension), selected to allow extensive sampling for cross-validation purposes. In total 68 fresh frozen individual biopsies were taken from the primary tumor, and the remaining formalin-fixed residual mass (1258 grams of tissue) was homogenized under the Rep-Seq protocol. To define the variant landscape in this tumor, whole exome sequencing (WES) was first conducted on a selection of 7 spatially disparate primary biopsies and an aliquot of the Rep-Seq sample (median 162× depth), leading to the discovery of a total of 76 non-synonymous mutations (SNVs and small scale insertion/deletions).

Figure 2:
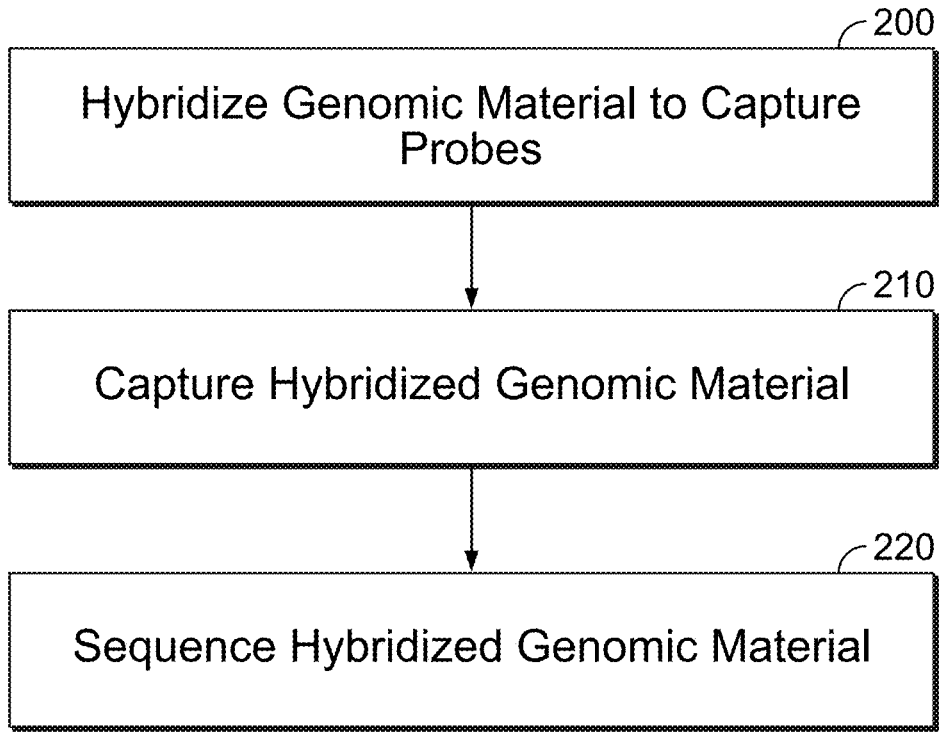
FIG. 2 provides a flowchart setting forth the steps of sequencing genomic data derived from a homogenized tumor sample.
Figure 3:
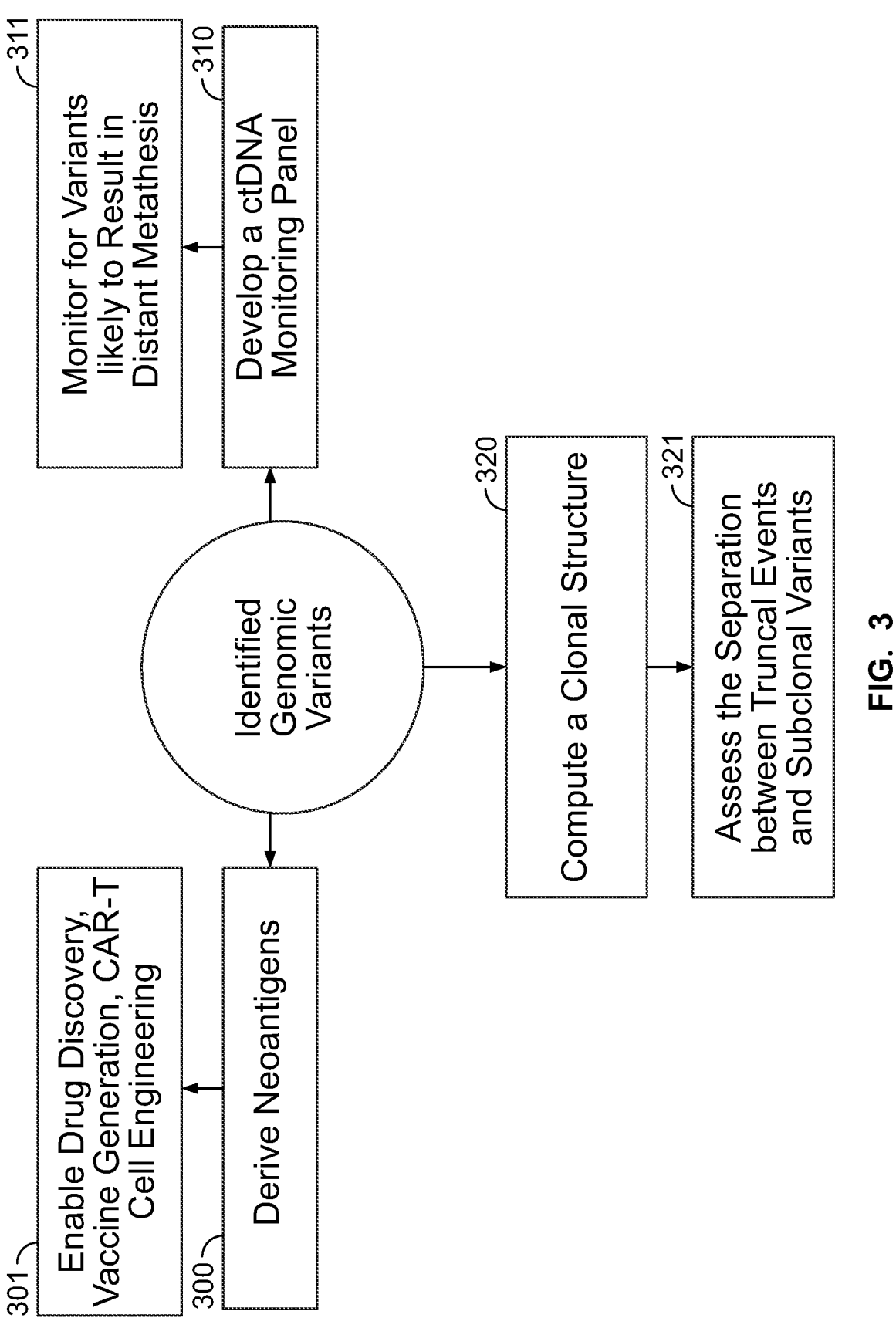
FIG. 3 illustrates further downstream processes which may occur following the identification of a plurality of genomic samples from a homogenized tumor sample.
Figure 5C:
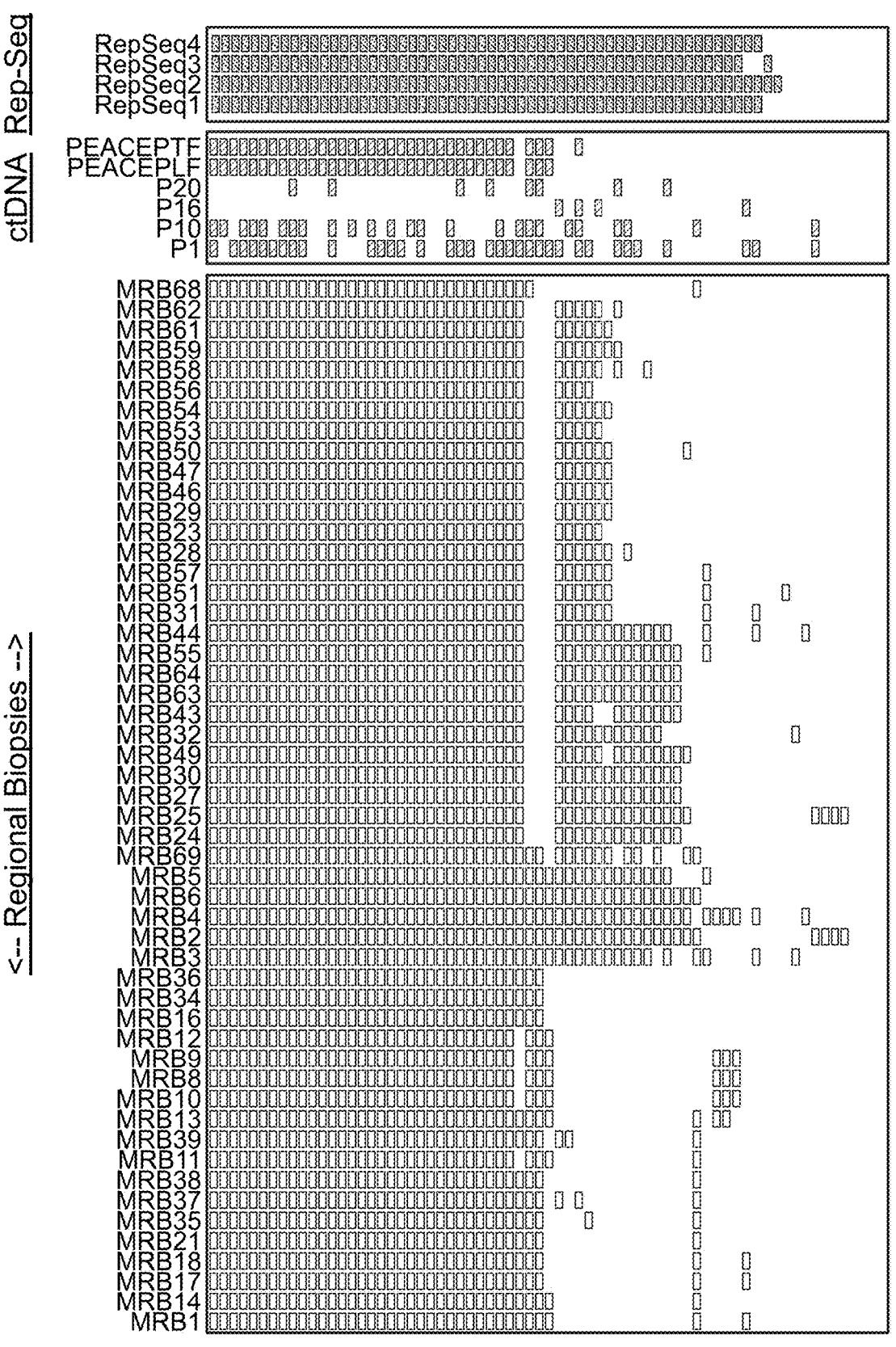
Figure 5D:
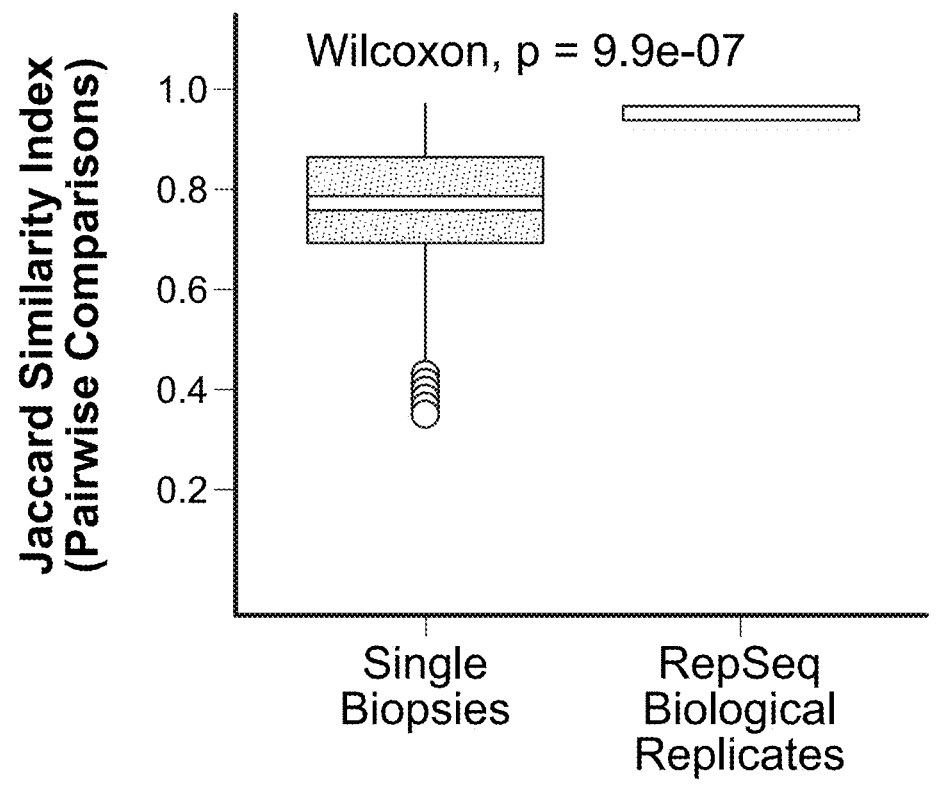
Figure 5D:
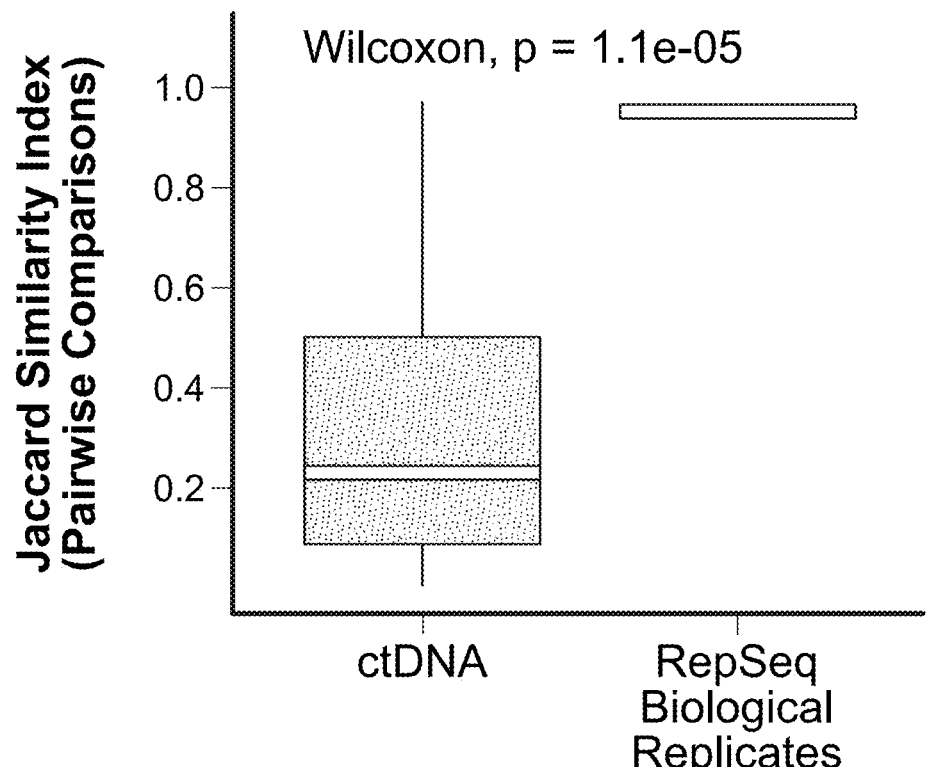
Figure 5E:
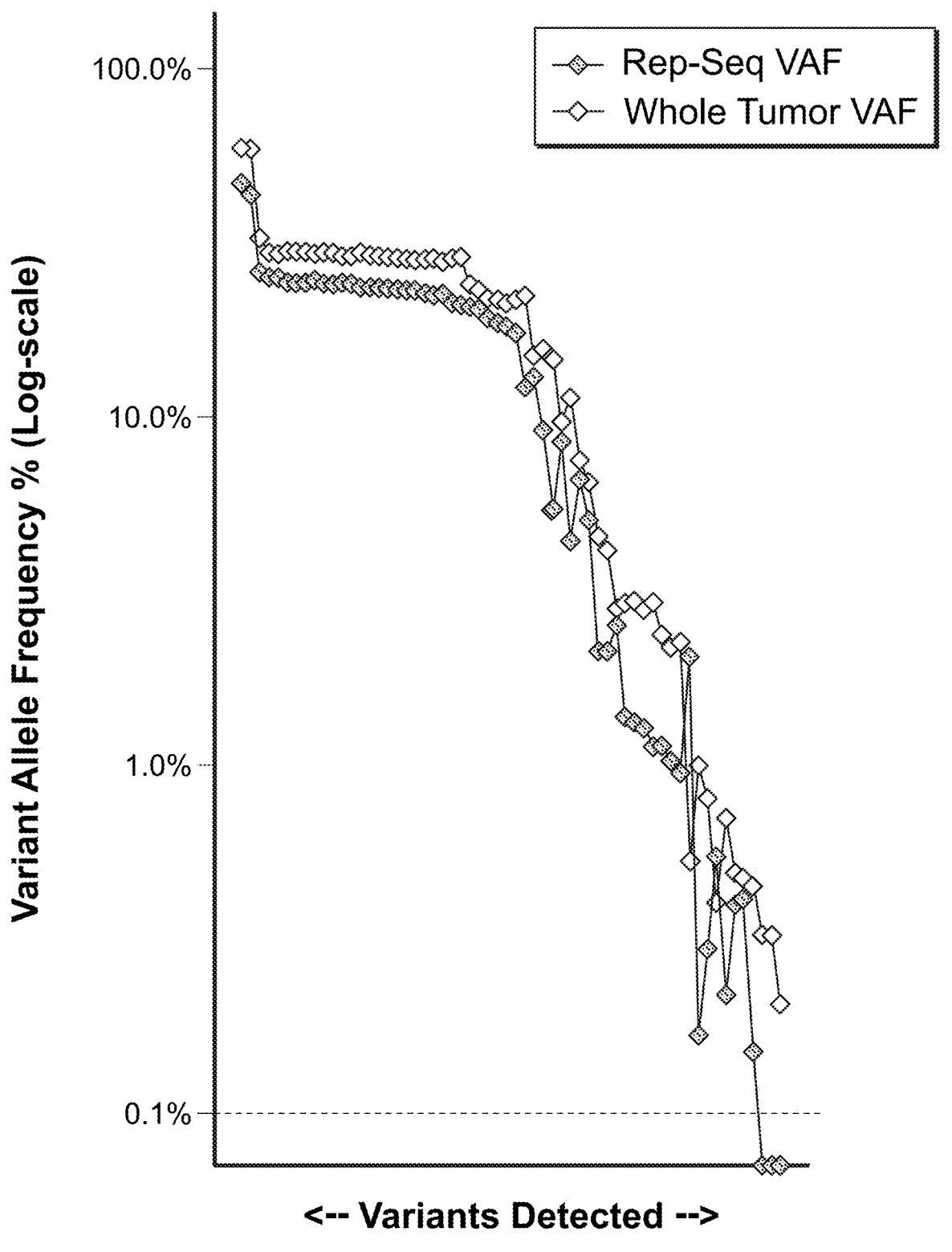

These 76 mutations were subsequently captured in a targeted custom panel, and sequenced to high depth (median 15,402× depth) in the 68 primary biopsies, 11 biopsies taken from 2 lymph node metastases, 4 biological Rep-Seq replicates (primary tumor), 6 circulating tumor (ct) DNA samples collected at different time points, and 3 homogenized lymph node Rep-Seq samples (one lymph node was not biopsy sampled) (FIG. 5B). The development of targeted custom panels is described in US Publication No. 2009/0246788, the disclosure of which is hereby incorporated by reference herein in its entirety. This integrated dataset was used to comprehensively evaluate the Rep-Seq methodology (FIG. 5C). First, we evaluated the reproducibility of each method, comparing the Jaccard similarity index between pairwise combinations of primary tumor biopsies, versus pairwise biological replicates of Rep-Seq, and pairwise combinations of ctDNA time points. Median pairwise similarity between biopsies was 0.77, suggesting approximately a quarter of mutations discovered in individual biopsies cannot be reproduced in subsequent biopsy samples. By contrast median similarity between Rep-Seq replicates was significantly higher at 0.95 (p=9.9×10$^{-7}$, FIG. 5D with almost identical mutation lists discovered by each replicate (FIG. 2c). Pairwise similarity between plasma ctDNA samples was low (overall median similarity index=0.24, FIGS. 5C-5D), reflecting the technical challenges in ctDNA profiling.

Figure 7:
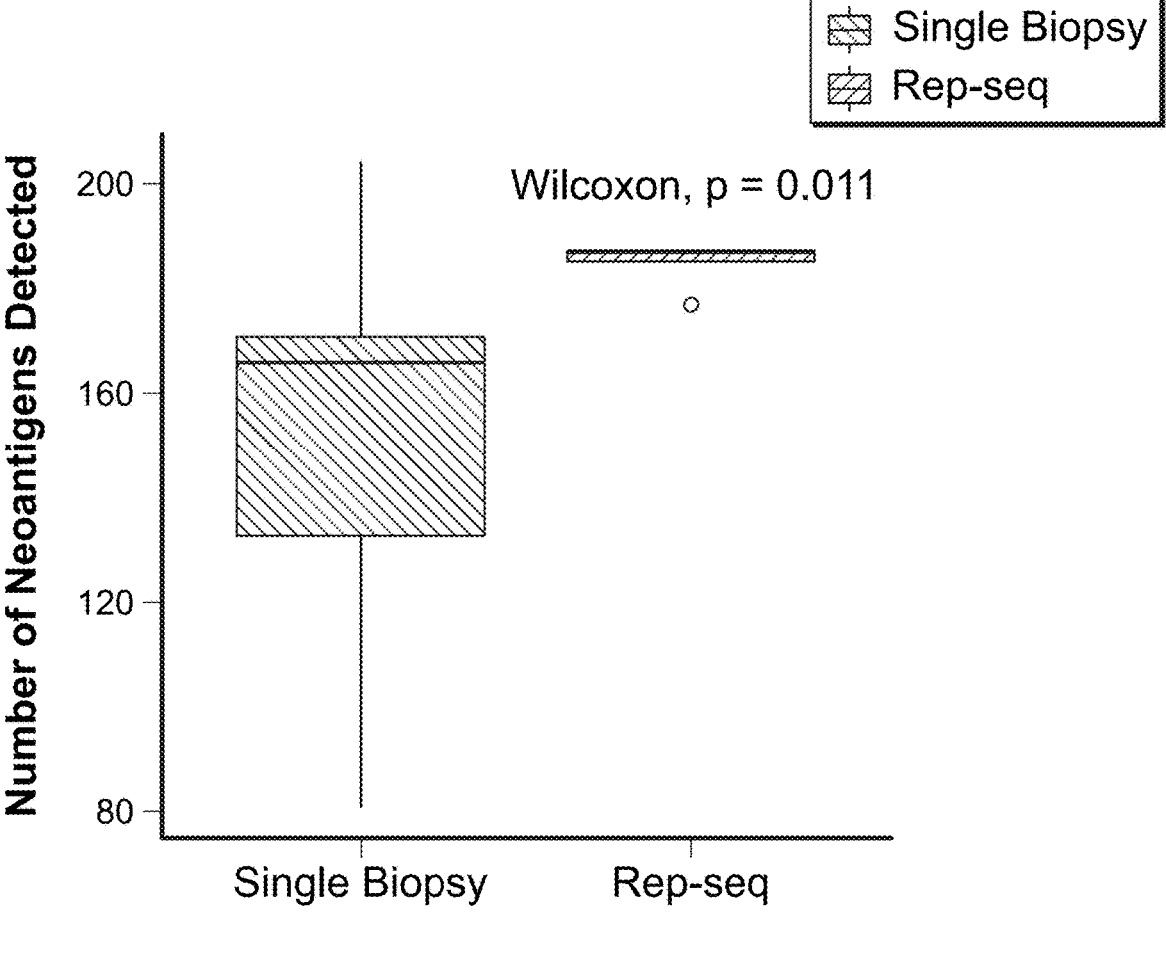
FIG. 7 illustrates the predicted neoantigens from each biopsy sample and Rep-Seq biological replicate for case Rep-Seq1. While tumors may contain thousands of mutations, or variants, only some of these mutations will be presented to the immune system as neoantigens (i.e. changed proteins that are sensed as "foreign" to the immune system). It is impossible to know a priori whether a mutation will be effectively recognized by the immune system as foreign, therefore computer algorithms are used to predict the antigenicity of modified (i.e. mutated) proteins. Neoantigens can be used to illicit an immune response in a cancer patient by creating a personalized vaccine. A critical component of an effective immune response following vaccination with targeted personalized neoantigens is (1) appropriate detection of the clonality of a neoantigen (as a subclonal neoantigen that elicits an immune response will only eliminate the cancer cells with that neoantigen), and (2) discovering as many neoantigens as possible from every patient (as knowing whether a predicted neoantigen will be a productive stimulator of the immune system is impossible, the utility of personalized cancer vaccines is likely dependent on the number of neoantigens targeted). Rep-Sep, therefore, will be superior to single biopsies in all cases, as indicated in FIG. 7.

In addition, the ongoing temporal evolution of the tumor across ctDNA time points should be also be recognized, however we note substantial difference even between close time points, e.g. P16 and P20 were only 21 days apart, but shared no mutations in common. Mutations detected by Rep-Seq were predominantly clonal (in every cancer cell) or events in major subclones, whereas biopsy sequencing frequently detected low frequency minor subclonal alterations, only present in a small proportion of tumor cells. Minor subclonal mutations are well documented and frequently of interest in a research setting (refs), however for clinical utility unambiguous identification of truly clonal alterations and a high level of reproducibility are frequently more important goals. Furthermore, the benefit of a wider sampling frame, which detects clonal plus major subclonal mutations, leads to a higher rate of overall variant detection versus single biopsy profiling (as the latter will miss subclonal mutations present in spatially distant tumor regions). A higher rate of mutation detection is likely to be of particular importance in the design of personalized adoptive cell therapy or vaccine immunotherapies, and we note the average number of neoantigens discovered was significantly higher (+19%) using the Rep-Seq method (mean neoantigens across Rep-Seq biological replicates=185, mean across single biopsies sequenced=155, p=0.011, FIG. 7).

Figure 6A:
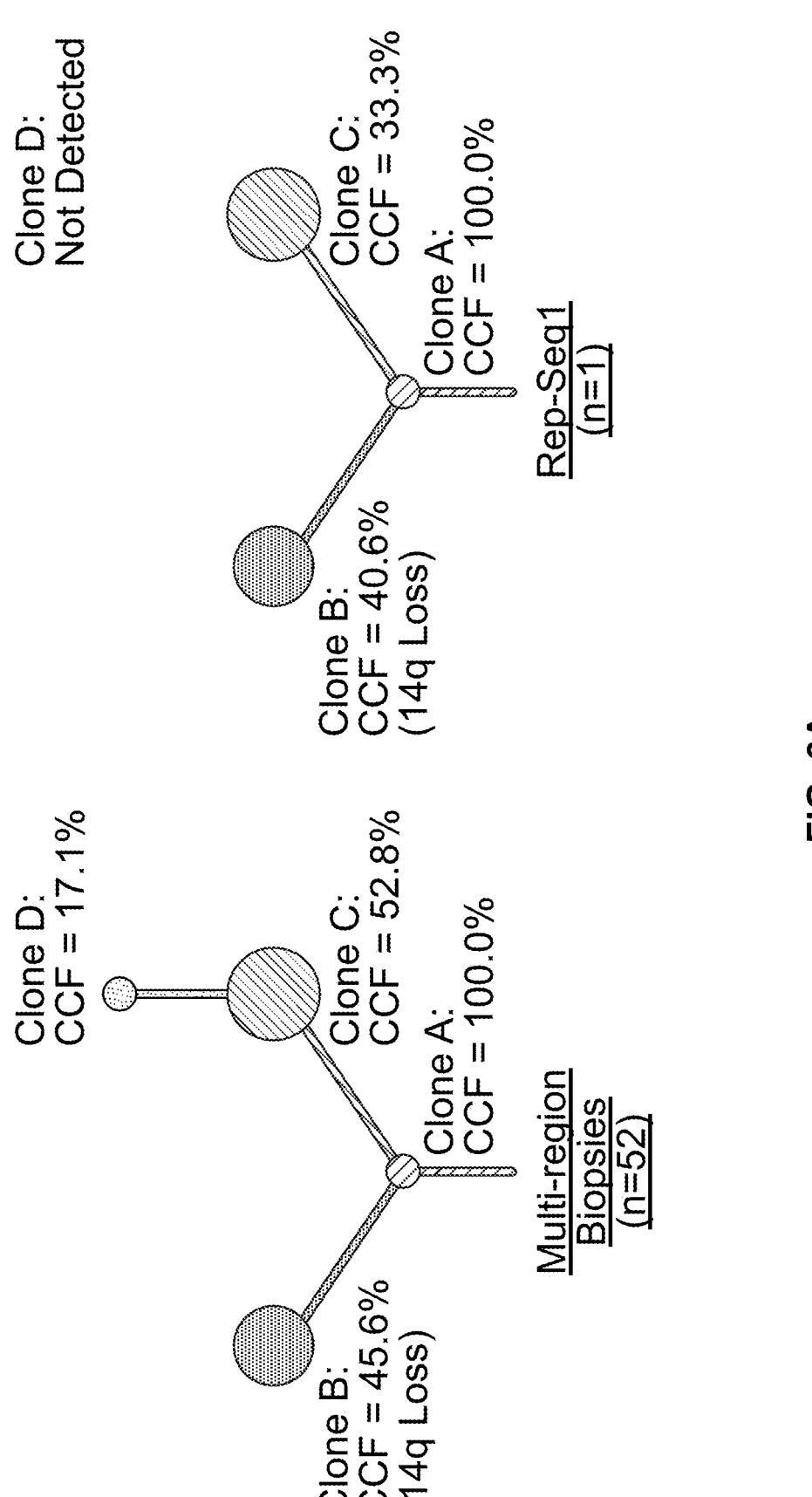
FIGS. 6A-6F illustrate clonal tracking by Rep-Seq and ctDNA.
Figure 6B:
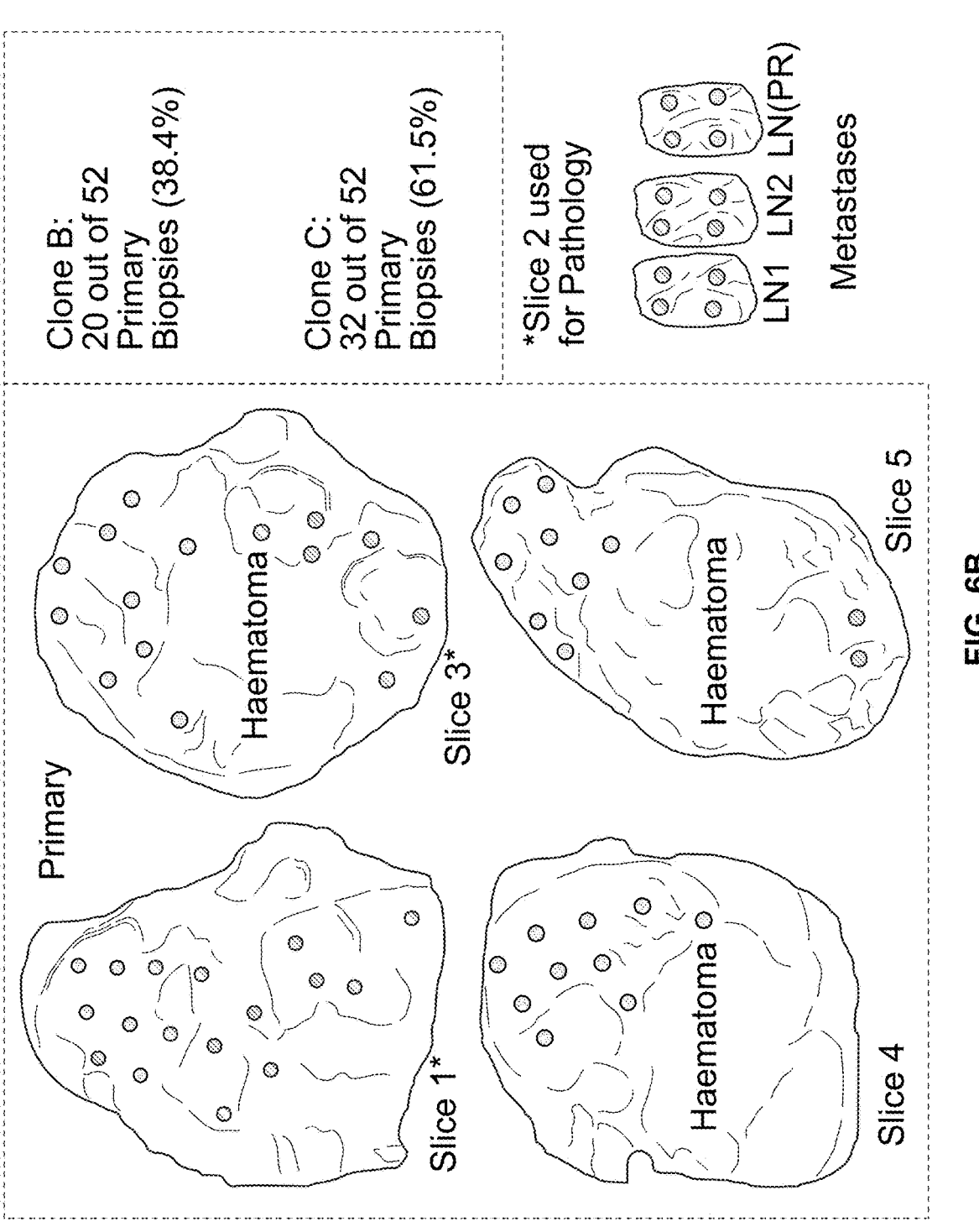

Next, we investigated the utility of Rep-Seq in determining clonal structure, given that measures of clonal diversity have been shown to associate with prognosis[9-10]. Cancer cell fraction (CCF) estimates were first calculated for all mutations (n=76) within the Rep-Seq1 primary tumor biopsy set (n=52 biopsies passing clonal quality control) and grouped together into mutational clusters to infer a truth-benchmark clonal structure (see methods). Four distinct tumor clones were detected: clone A (truncal clone, mutations in every cancer cell CCF=100.0%, n=41 mutations), and (sub)clones B (CCF=45.6%, n=6 mutations), C (CCF=52.8%, n=3 mutations) and D (CCF=17.1%, n=2 mutations) (FIG. 6A). The clustering process was repeated for the Rep-Seq sample alone (n=1), and the clonal solution was then compared between methods (FIG. 6A). Rep-Seq correctly clustered all 41 clonal mutations together into the truncal clone A (CCF=100.0%), as well as identifying major (sub)clones B (CCF=40.6%) and C (CCF=33.3%) (FIG. 6A). The lowest frequency subclone (clone D, CCF=17.1%) was not detected as a distinct cluster in the Rep-Seq sample, reflecting the challenge in accurately grouping together lower frequency mutations. Cancer cell fraction estimates from both methods were validated against physical mapping of spatial biopsy locations and mutational presence, back to images of the tumor slices: (sub)clone B was found in 20 out of 52 primary biopsies (38.4%) and (sub)clone C was found in 32 out of 52 (61.5%) (FIG. 6B). This confirmed the presence of two major, spatially distinct, subclones. Intriguingly, lymph node metastases LN1 and LN2 were exclusively seeded by clone B, whereas spatially proximal peri-renal lymph node sample LN(PR) was polyclonal, with clones B and C present.

Figure 6C:
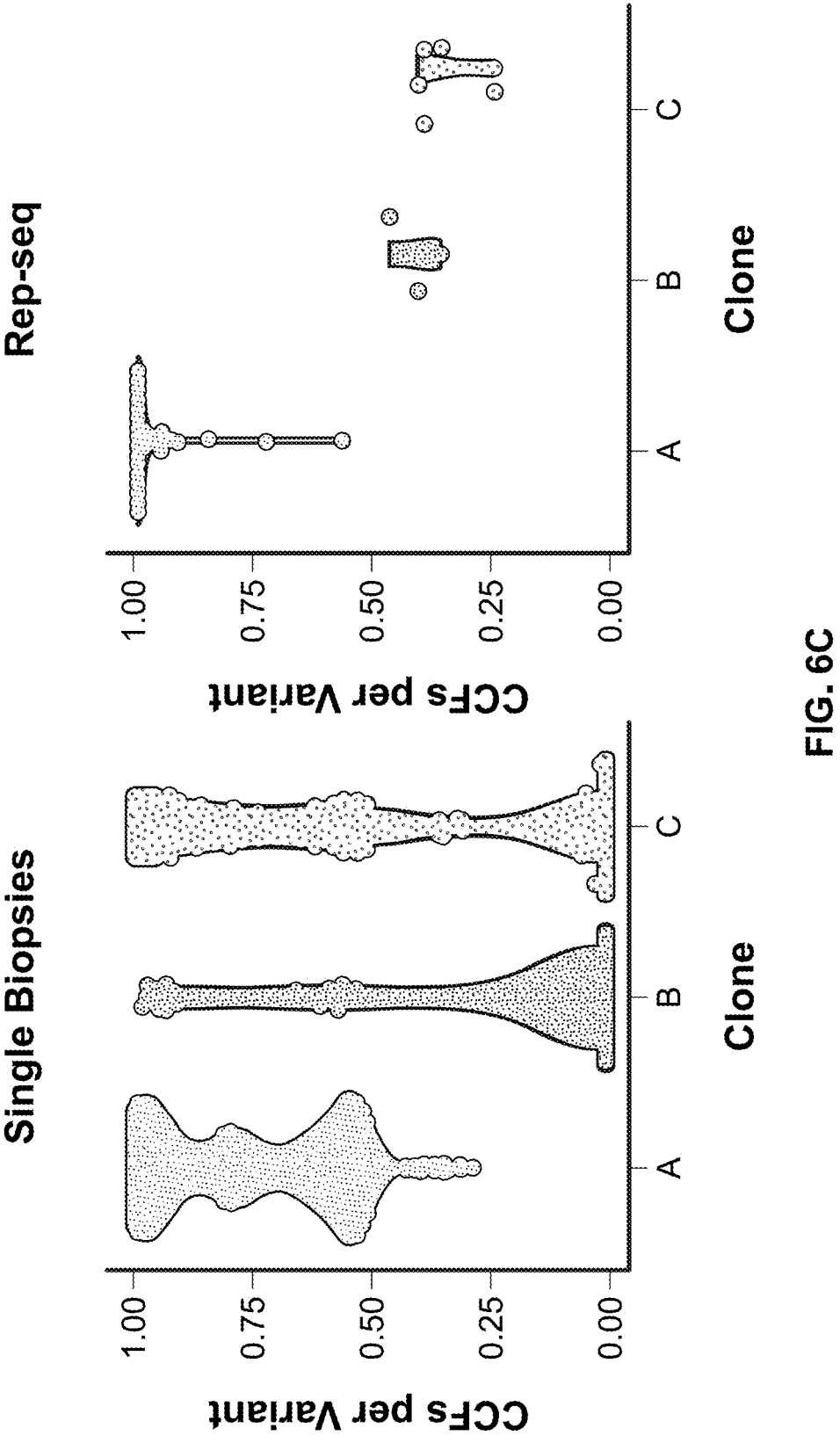

Individual mutation CCFs within each sample were next considered, in order to assess how well separated truncal events (i.e. mutations that are clonal or present in every cancer cell) (clone A) were from subclonal mutations (clones B and C). Within the Rep-Seq sample, CCF estimates for clonal events (clone A) were clearly separated from (sub)clones B and C, reflecting the rapid convergence of CCF estimates in Rep-Seq towards true values (FIG. 6C). By contrast CCF distributions in single sample biopsies overlapped between clones A, B and C, with sub(clones) B and C frequently appearing (incorrectly) as clonal in individual biopsies with CCFs=~100% ("illusion of clonality"). On average across the 52 primary biopsies 17% (range [6%-35%]) of clonal variants suffered from an illusion of clonality when considered as a single region (FIG. 6D) (all 76 mutations included, see methods).

Figure 6D:
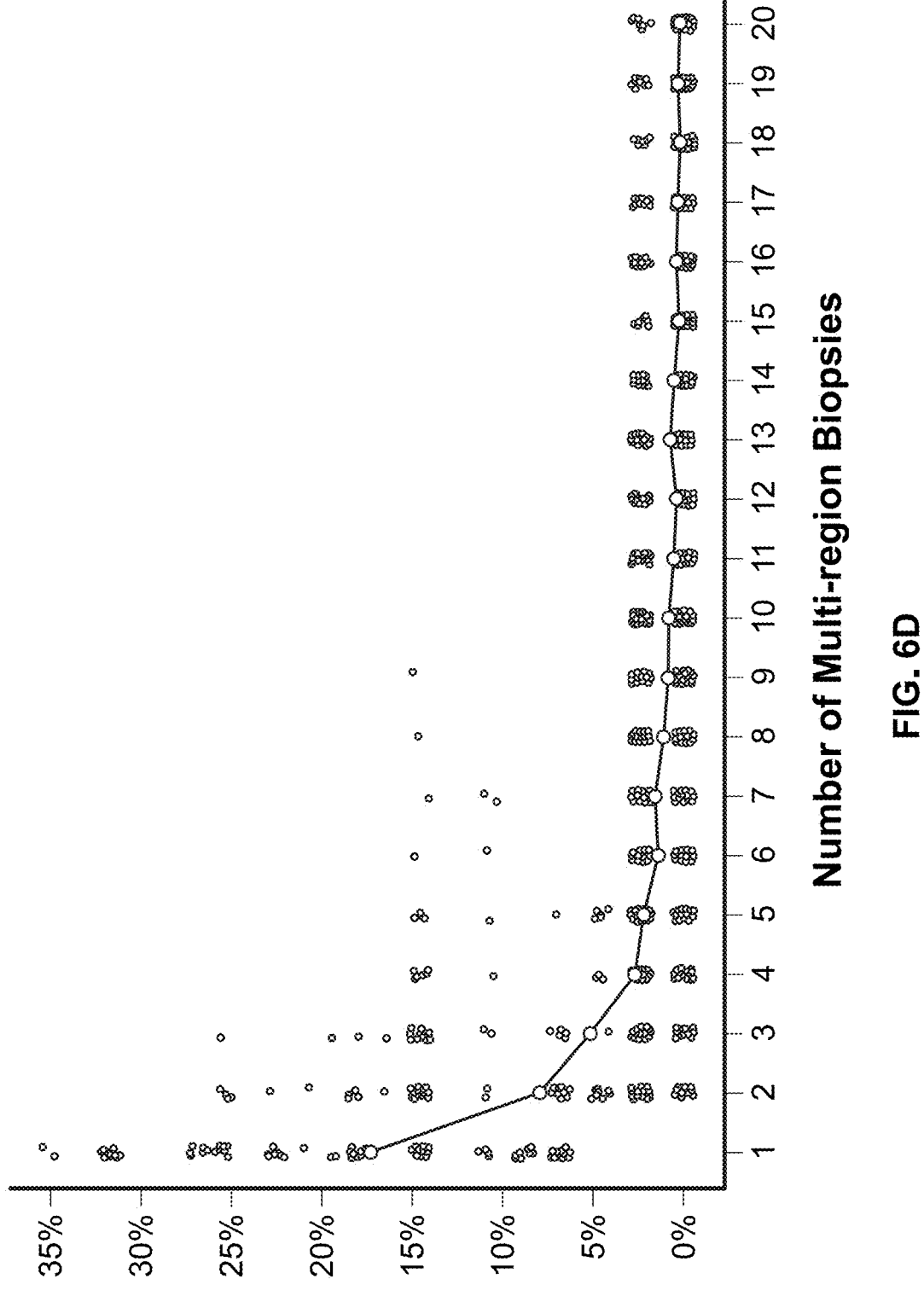

An illusion of clonality persisted even with multi-region biopsy sampling; with simulation showing that two random biopsies yielded an illusion of clonality rate of 9% [0%-25%], three=6% [0%-25%], four=4% [0%-15%] and five=3% [0%-15%](FIG. 6D). Furthermore, these results are likely to represent a conservative under-estimation of true illusion of clonality rates, as 3-dimensional sampling was conducted along the z-axis. We note that if normal 2-dimensional tumor slice sampling had been conducted only on slice 4, which was monoclonal for clone C, then no number of biopsies would have prevented clonal illusion (FIG. 6B), and worryingly clone B (which metastasized to the lymph nodes) would have been completely missed.

Figure 6E:
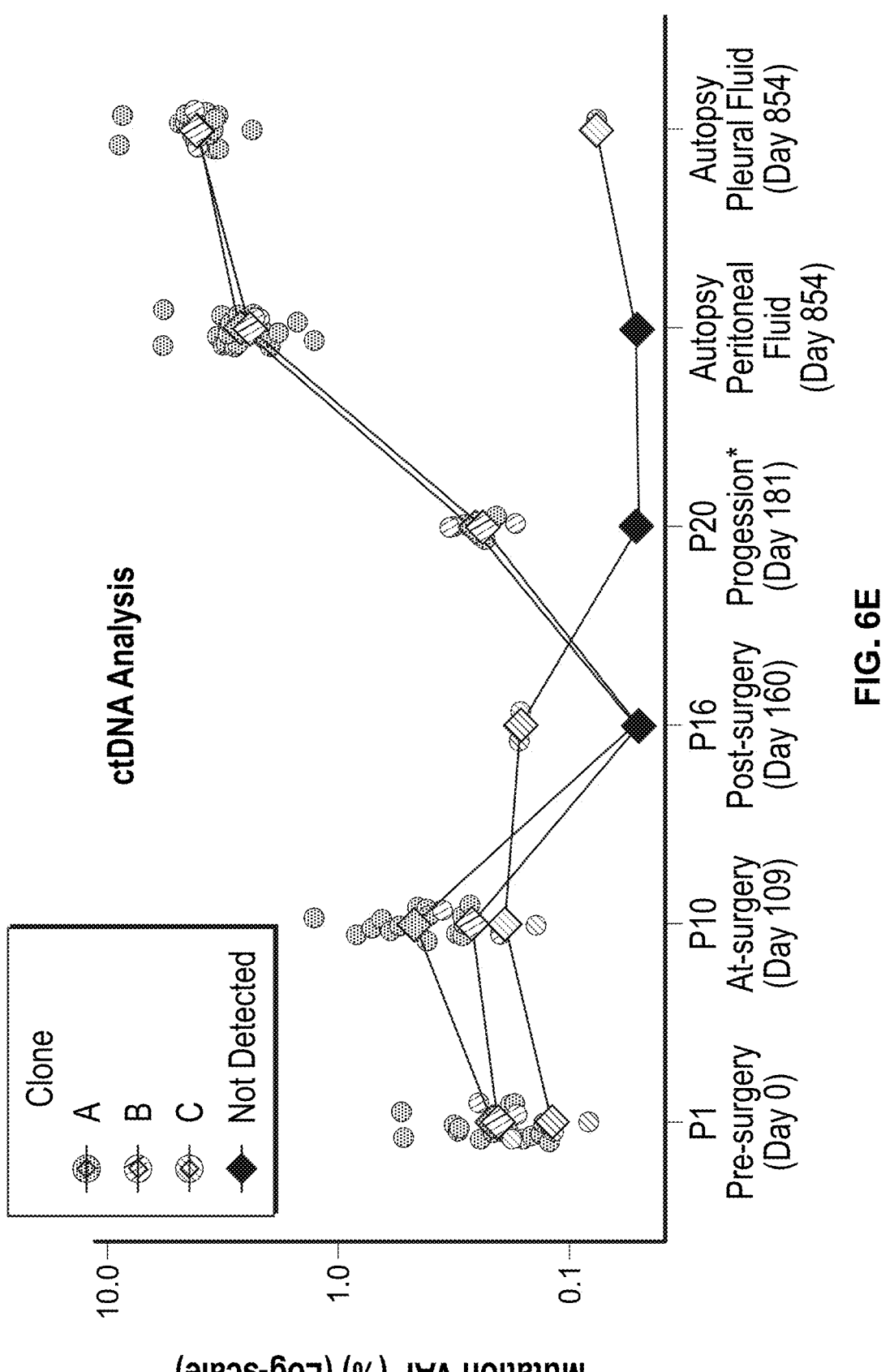

Given the broad applicability of liquid biopsies, and previous work demonstrating that both clonal and subclonal mutations can be identified[11], a pertinent question is to what extent do ctDNA samples from plasma represent true clonal diversity as compared to a representative sampling of the primary tumor. Taking the opportunity of having a well characterized primary tumor, and 6 longitudinal ctDNA time points, we investigated this question. At pre-surgery time points (P1 and P10) variants from clones A, B and C were all detectable at VAFs 0.1%-1.0%, however many variants were missed, including some clone A truncal events, reflecting the technical challenges profiling ctDNA. Mean VAF within clone A was overall higher than (sub)clones B and C, however large inconsistency was observed in terms of individual variants and across time points (FIG. 6E). At post-surgery time point P16 the highest VAF variant was actually from clone C, and similarly at time point P20 a clone B mutation was highest, both above any clone A truncal mutations (FIG. 6E). In later stage time points however (at time of autopsy) all clonal mutations were detected, with highly consistent VAF frequency (FIG. 6E).

Figure 8A:
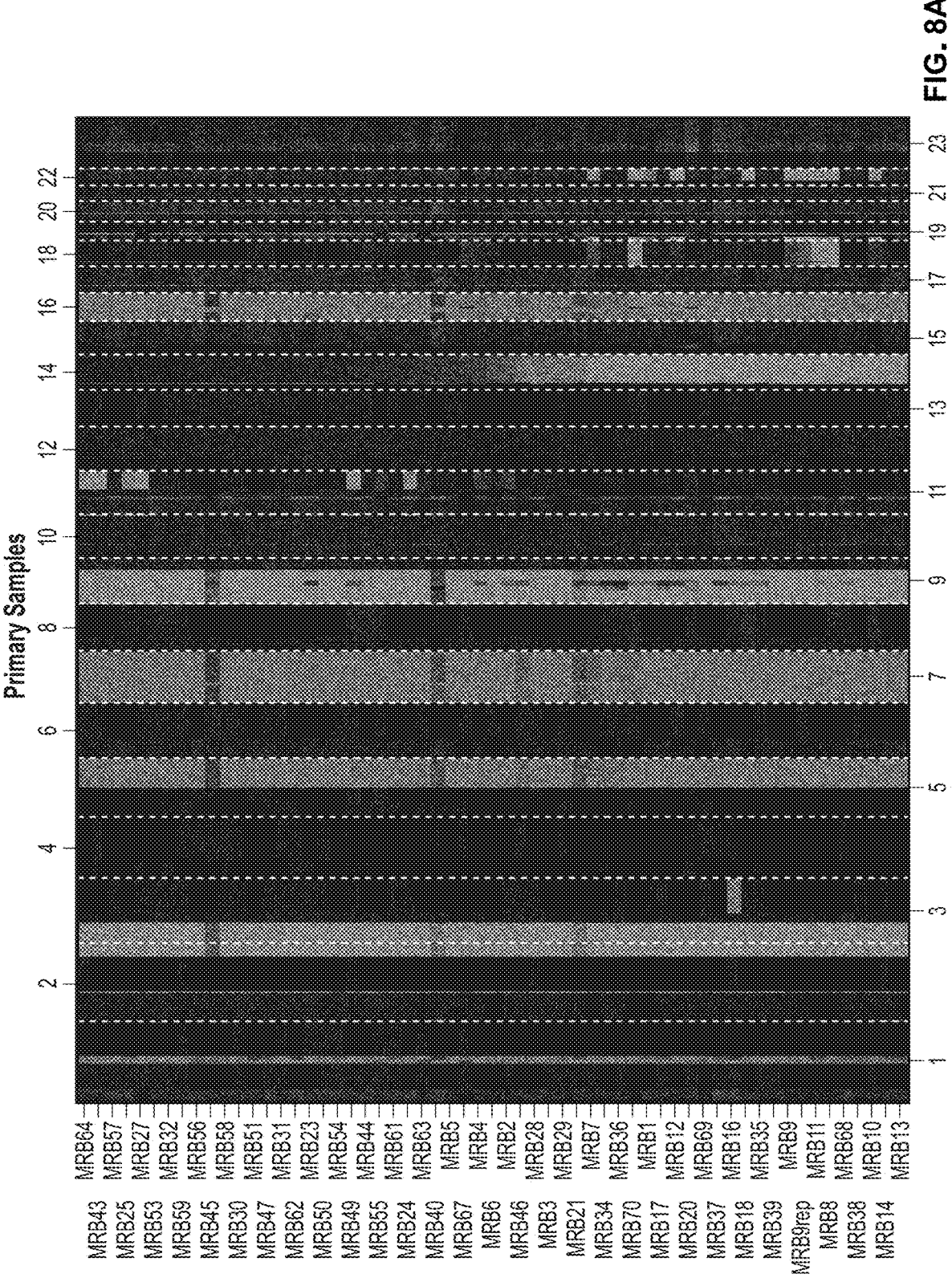
FIGS. 8A and 8B set forth a copy number heatmap for all primary biopsy regions for Rep-Seq1 (FIG. 8A)), together with metastatic biopsy regions (FIG. 8B) taken at time of rapid autopsy, from 20 distinct anatomical sites of disease. Biopsies are ordered based on descending log(R) values for chromosome arm 14q. The metastatic regions all contain 14q loss, along with approximately half of the primary biopsy regions (clone B), suggesting metastases were seeded by clone B. Although we note we cannot exclude the possibility the 14q loss in metastases was an independent parallel event, however the combined ctDNA data, lymph node representative sequencing and autopsy metastases data, would all support that hypothesis.
Figure 8B:
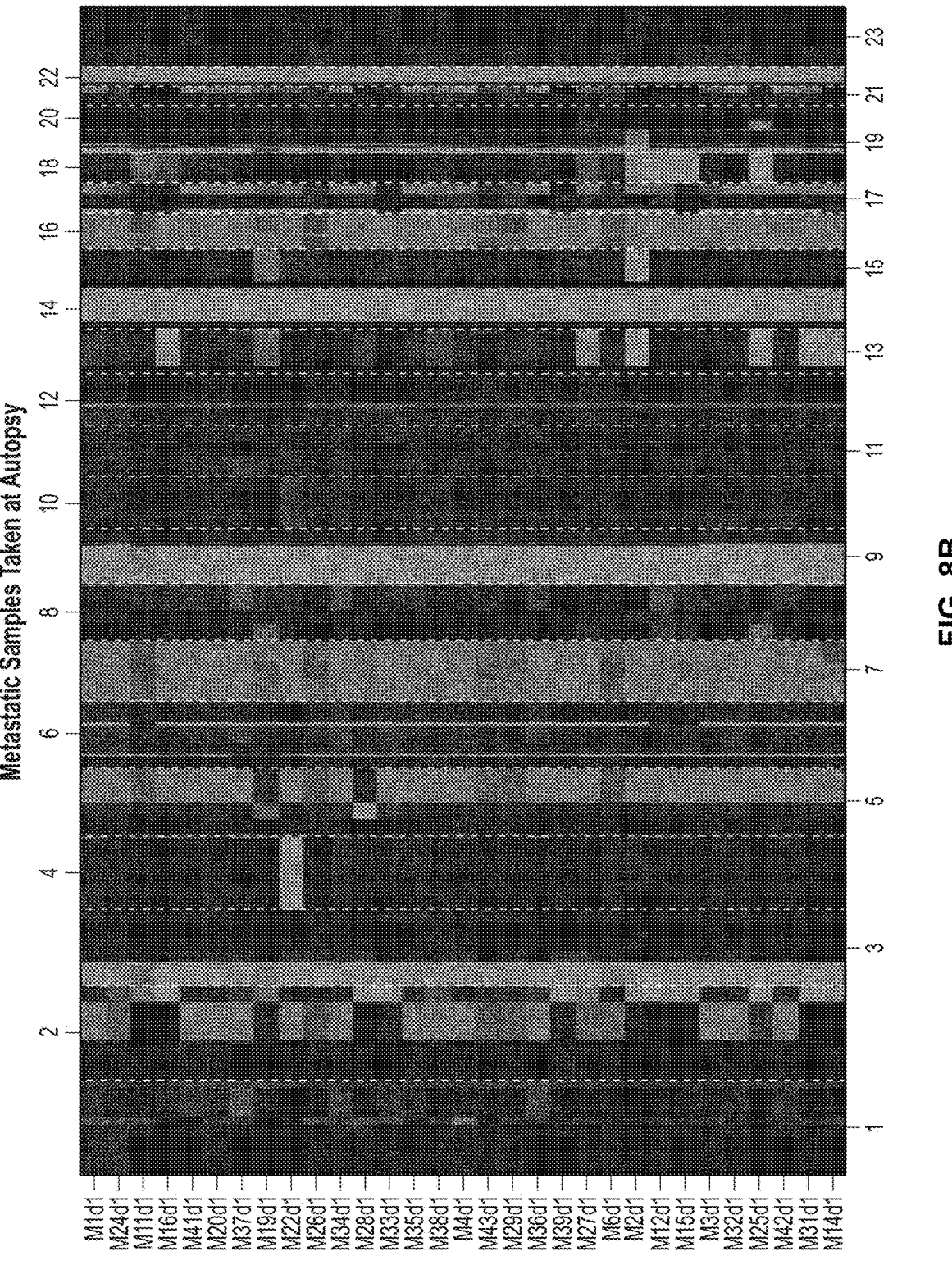

Correlation coefficients of VAFs from ctDNA, compared to the count of how many biopsies a mutation was present in, ranged from r=−0.17 (time point P16) to r=0.78 (autopsy pleural fluid). Rep-Seq CCFs had the highest correlation with biopsy count data, with r=0.90. This suggests inferring de novo clonal structure from ctDNA alone remains challenging, however tracking clonal markers that have been previously identified from tumor tissue remains highly informative (e.g. for minimal residual disease tracking (MRD)). We note in the context of MRD tracking, a larger panel of variants is likely to increase sensitivity to detect relapse at earlier time points, e.g. in the Rep-Seq1 data at time point p16 an MRD panel designed from a single biopsy would have missed disease relapse 53% of the time, compared to a 0% miss rate using a Rep-Seq sample (Table S2). In terms of the clonal dynamics of Rep-Seg1, an interesting pattern was observed with clone C dying out in later ctDNA time points and becoming undetectable (FIG. 6E). This supports the predicted metastatic seeding pattern, as determined by biopsy and Rep-Seq profiling, i.e. that clone B achieved distal metastatic seeding, whereas clone C was contained within the (peri)-renal area (FIG. 6B). As an additional validation, copy number analysis was conducted on 43 further biopsies, sampled from 20 distinct anatomical sites of metastatic disease present at the time of Rep-Seq1 autopsy. All sites contained loss of 14q, a driver event found only in clone B in the primary tumor (FIG. 8). We note in single region biopsy sequencing; metastasizing clone B would have been missed 32 times out of 52 (61.5%).

Figure 6F:
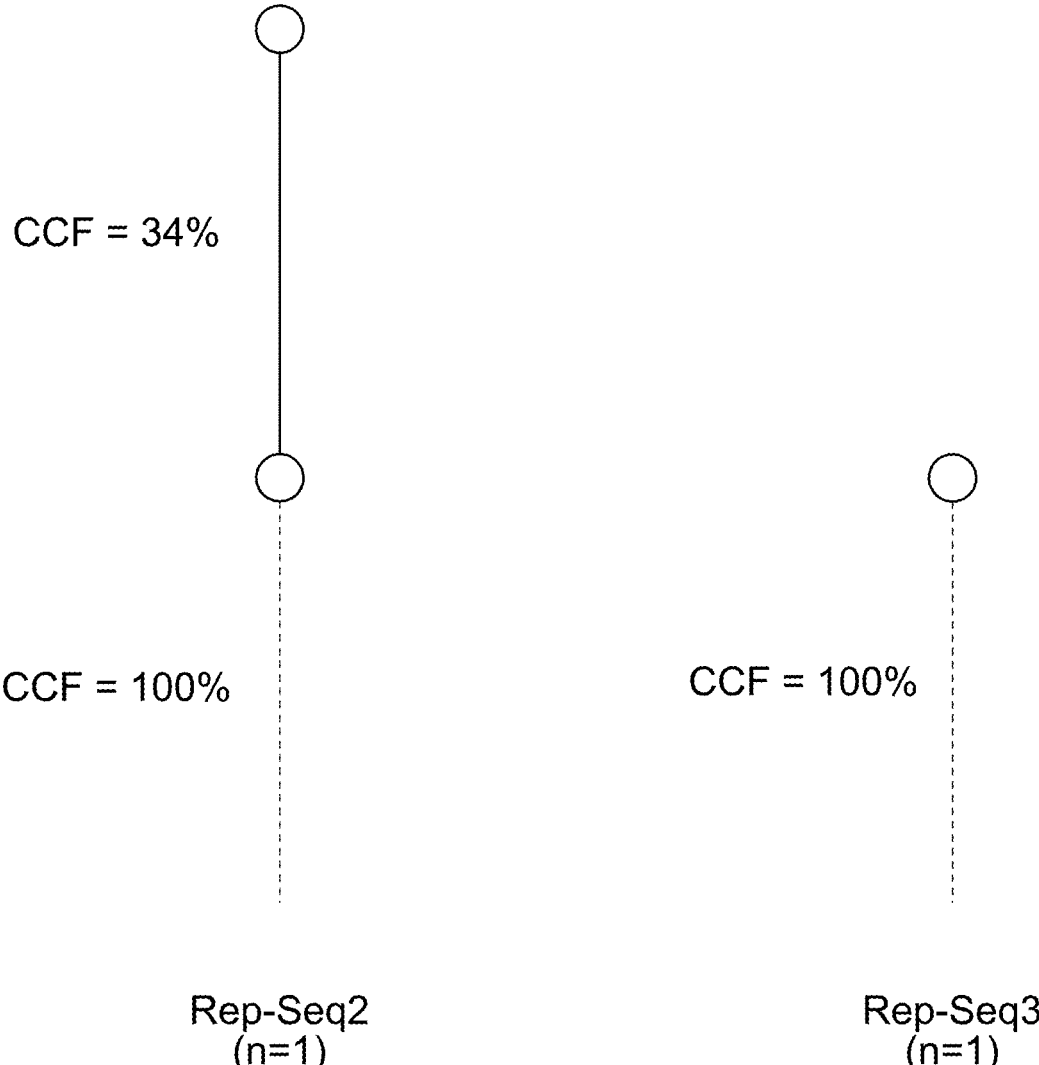
Figure 6G:
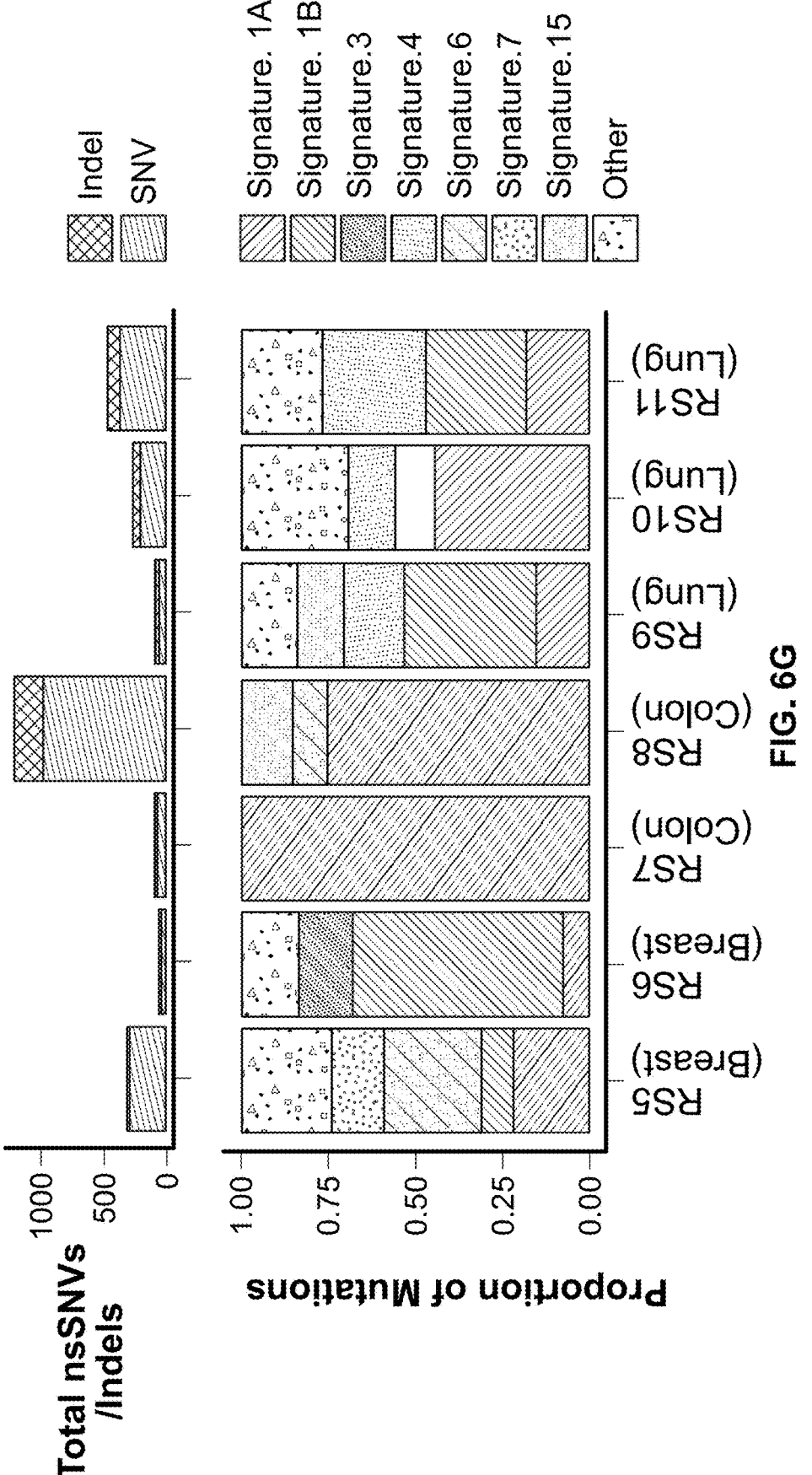
FIG. 6G illustrates non-synonymous mutation count for cases Rep-Seq4 to Rep-Seq11 (top), along with mutational signature analysis results (bottom).
Figure 6H:
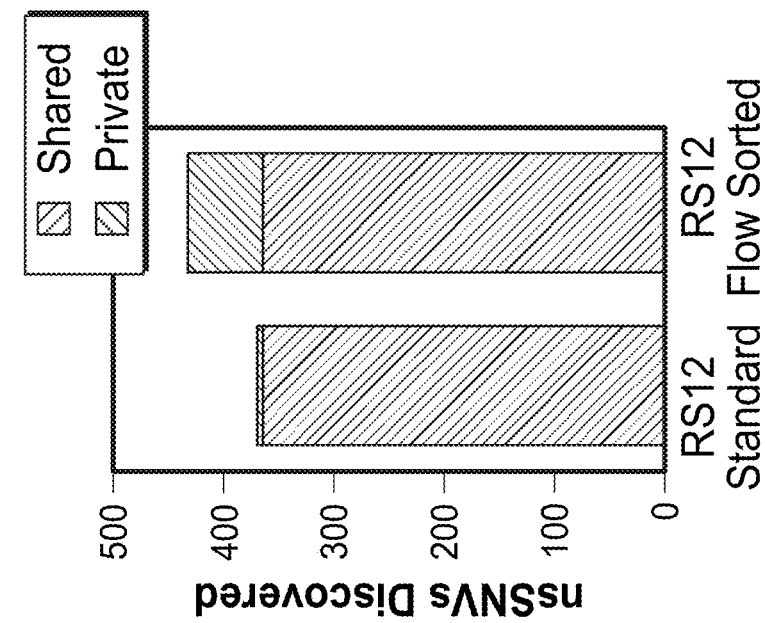
FIG. 6H illustrates Rep-Seq11 coverage data, for the overall bulk mixed cell population, and then an estimated tumor cell coverage, along with purity estimates (left). Data is shown for standard Rep-Seq, and then tumor purity enriched Rep-Seq, for comparison purposes.
Figure 6H:
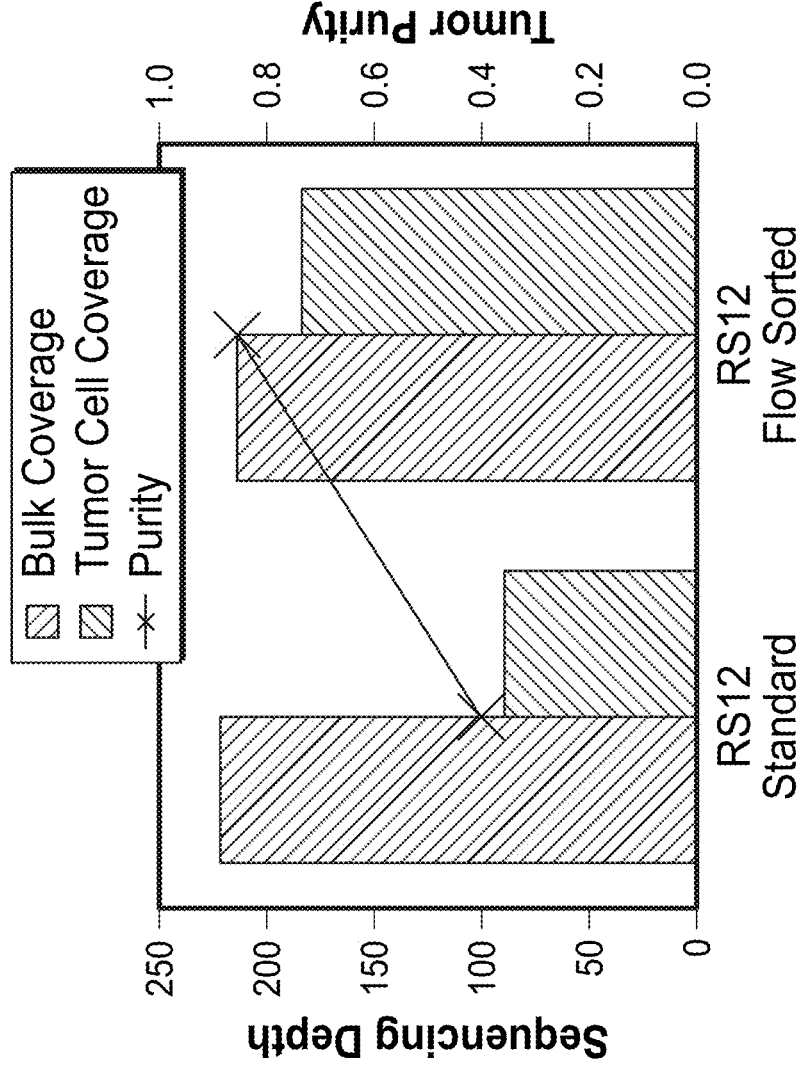

The Rep-Seq method was additionally conducted in a further 10 cases, as a technical feasibility exercise. Cases Rep-Seq2 and Rep-Seq3 were additional ccRCC tumors and appeared to have a predominantly monoclonal structure (FIG. 6F). Cases Rep-Seq 4 to Rep-Seq10 were tumors of breast, colorectal and lung primary sites, and tumor specific driver mutations were successfully detected in all specimens. The highest mutation burden was observed in Rep-Seq7 (colon), with 980/251 nonsynonymous SNVs/Indels, and presence of cosmic mutational signatures 6 and 15 associated with mismatch repair deficiency (FIG. 6G), which was confirmed by IHC showing loss of MHL1. Signature analysis of the three non-small cell lung cancer (NSCLC) tumors (Rep-Seq8, Rep-Seq9, Rep-Seq10) showed evidence of signature 4 (smoking associated) uniquely in these three tumors only (FIG. 6G). Hence the mutational signatures derived from Rep-Seq were consistent with expected patterns. Finally, an additional benefit of tissue homogenization is the ability to add in a cell sorting step, to enrich for higher tumor purity.

As a proof of principle flow sorting was conducted on Rep-Seq11 (colorectal tumor), preferentially selecting tumor cells based on the presence of cytokeratins 8 and 18. Whole exome sequencing was conducted, on first a standard sample from the Rep-Seq protocol (non-sorted, depth 221×), which showed tumor purity of 0.44. Significant enrichment was observed in the flow sorted Rep-Seq sample (depth 215×), with purity of 0.89, which resulted in an approximate doubling of the effective tumor cell sequencing coverage (from 90× to 184×), for the same overall bulk sample sequencing depth and cost (FIG. 611). In terms of variant discovery, 365 non-synonymous SNVs were observed in common between both standard and flow sorted samples, and then an additional 68 mutations (+19% increase) were found uniquely in the flow sorted sample, presumably due to the increased sensitivity from higher effective tumor depth (FIG. 611). Only 5 mutations (1.4% of total) were found with the opposite pattern, i.e. in the standard sample but missing in the flow sorted, which suggests flow sorting does not create systematic bias such that certain tumor subclones are excluded.

In conclusion, Rep-Seq effectively implements an unbiased tumor sampling approach, drawing DNA molecules from a well-mixed homogenized solution of all residual surgical tumor material, hence removing spatial bias inherent in current single and multi-region biopsy approaches. We show a wider sampling frame leads to an overall increased sensitivity to detect mutations, with the trade-off of losing resolution to detect smaller (sub)clones, but the gained ability to comprehensively map all the major subclones. This trade-off may be acceptable in a clinical context, where lower frequency mutations may be less directly actionable than widely-expanded clonal or major subclonal driver events. The reproducibility of results in Rep-Seq was significantly higher than current single biopsy sequencing approaches (at same equivalent sequencing depths), and greater accuracy was also achieved in determining clonal from subclonal variants.

Materials and Methods

Study Cohorts

Cases Rep-Seq1, Rep-Seq2 and Rep-Seq3 were diagnosed with renal cell carcinoma and were consented for research under the TRACERx Renal study (National Health Service Research Ethics Committee approval 11/LO/1996), as previously described[5]. Residual surgical material for cases Rep-Seq4, Rep-Seq5, Rep-Seq6, Rep-Seq7, Rep-Seq8, Rep-Seq9, Rep-Seq10 and Rep-Seq11 were obtained from commercial providers of research specimens (GLAS Consultants, Winston-Salem, NC. (IRB #: 120160685) and The MT Group, Van Nuys, CA (MTG-015)) from U.S. hospitals, under IRB approval.

Clinical Audit of Current Molecular Profiling Practices

Institutional review board approval was obtained for a service evaluation to quantify the tumor volume routinely profiled as a diagnostic standard of care in resected colorectal, melanoma and sarcoma tumors (SE725), where surgery and molecular profiling were both undertaken at the Royal Marsden NHS Foundation trust, London, UK. A list of cases from May 2016 to May 2018 was obtained for each tumor type and reviewed. Cases were included if there were >2 macroscopic tumor dimensions recorded on the histopathology report and if information was available on the number and thickness of slides used for molecular profiling.

Regional Biopsy and Cocktail Sample Preparation

Multi and single region biopsy sampling of surgically resected tumor tissue was conducted using the same method as previously described[5]. Cocktail samples (as displayed in FIGS. 4A-4F) were created for each tumor, by pooling extracted DNA taken from all single-regions taken for each tumor, in equimolar ratios. A median of 9 single-region samples were pooled per cocktail.

Grossing and Homogenization of Rep-Seq1 Tissue

Following diagnostic histologic sampling and removal of fresh biopsies, three distinct clinical surgical waste tissues from a kidney radical nephrectomy (Rep-Seg1) containing: 1) a primary tumor, 2) para-aortic lymph node cluster, and 3) renal hilar nodes were fixed in 10% neutral buffered formalin for 24 h to mimic the standard clinical workflow. After fixation, samples were exchanged into phosphate-buffered saline (PBS) for 24 h, then stored in ethanol for until dissected. Tumor tissue was identified by a pathologist through macroscopic evaluation and physical palpation, and all identifiable tumor was dissected away from the surrounding tissue. An area of normal tissue (at least 5 cm from the tumor) was also dissected by a pathologist and retained. Lymph nodes detected during gross examination of the Rep-Seg1 specimen included hilar and peri-renal nodes were also dissected as an independent tissue samples. All dissected tissue was weighed prior to homogenization.

Residual primary tumor tissue was split into two-625 g portions; each portion was combined with 600 ml autoMACS Running Buffer (Miltenyi Biotec Inc., 130-091-221) and homogenized in a liquidizer for 3 min at the highest setting. The primary tumor homogenates (2.5 liter total) were manually combined and mixed in a plastic container, divided back and re-liquidized for additional homogenization and mixing, and pooled together into a large plastic container. Segregated tissues of renal hilar lymph nodes, peri-renal node, normal kidney tissue, and para-aortic lymph nodes were each homogenized independently in autoMACS Running Buffer (1:1, mass:volume) with an IKA Tube Mill (IKA Works Inc. Wilmington North Carolina, 0004180001) for 2 min at 15,000 rpm using single-use blending containers. When tissue mass exceeded the capacity of an individual blender container, homogenates for the same sample were pooled by mixing as described above. Samples of each tissue homogenate were stored in methanol (1:1, v:v) at 4° C. Cases Rep-Seq2 and Rep-Seq3 were primary renal tumors only and were processed through the same protocol.

Standard Method for Residual Tissue (SMRT) Processing

For cases Rep-Seq4 to Rep-Seq11, formalin fixed, residual tumor tissues were obtained from commercial providers of research specimens (GLAS Consultants, Winston-Salem, NC. and The MT Group, Van Nuys, CA) from U.S. hospitals under IRB approval. Each specimen had been subjected to standard sampling for diagnosis and staging purposes. These cases were considered surgical waste and slated for incineration, thus were stored in formalin for four to six weeks. Upon arrival, tissue was transferred to PBS for 12-24 h. Tumor tissue was identified by a pathologist through macroscopic evaluation and physical palpation, and all identifiable tumor was dissected away from the surrounding tissue. An area of normal tissue (at least 5 cm away from the tumor) was also dissected by a pathologist and retained. All dissected tissue was weighed prior to homogenization. Dissected tumor and normal tissue were homogenized separately in single-use blender containers (IKA Works Inc. Wilmington North Carolina, 0004180001), or single use consumer grade blenders (Hamilton Beach, 51102, Glen Allen, VA) in autoMACS buffer (1:1, m:v) for 2 min at 15,000 rpm. Filters were from Pluriselect (San Diego, CA). Buffers used were from the following companies: CC1 (950-124; Ventana Medical Systems, Tucson, AZ), antibody diluent (251-018, Ventana Medical Systems), autoMACS buffer (130-091-221, Miltenyi Biotech, Teterow, Germany), phosphate buffered saline (PBS, 14190, Fisher Scientific, USA). Tween 20 was purchased from Fisher Scientific, USA (AC233362500). DAPI (D9542) and Pepsin (P7012) were purchased from Sigma, USA. Proteinase K (0706) was from VWR, USA. Mouse anti-cytokeratin 8/18 antibody (760-4344) was from Ventana Medical Systems. Goat-anti-Mouse antibodies conjugated with Alexa Fluor 488 (A-11001) and Alexa Fluor 647 (A-21236) were purchased from Invitrogen. Resulting homogenates were stored at 4° C. until further processed.

Genomic DNA Purification from Tissue and cfDNA

An aliquot of each tissue homogenate (1200 microliters) was collected by centrifugation 5000 rcf for 2 min, rinsed with TE buffer pH 8.0 (VWR, AAJ62745-EQE) twice, and incubated in 5 ml protease digestion buffer [9.75 ml TE buffer pH 8.0, 60 mg Proteinase K (VWR, 0706), and 0.25 ml 20% SDS in aqueous solution (Amresco, 0837)] at 56° C. for 2-16 h. Digested tissue (100 microliters) was used for genomic DNA purification by High Pure PCR Purification Kit (Roche Applied Sciences, Mannheim Germany, 11 732 668 001) according to manufacturer's protocol. Purified genomic DNA was quantified using a NanoDrop 8000 (Thermo Fisher Scientific) and stored at –20° C. cfDNA was isolated from plasma using cobas cfDNA Sample Preparation kit (Roche, 07247737190).

Target-Enriched NGS Library Construction and Sequencing

Illumina compatible indexed NGS libraries were constructed from genomic DNA from tissue using the SeqCap EZ HyperCap Workflow User's Guide, v1.0 (Roche Sequencing Solutions) with notable parameters specified below. Briefly, 1 g of purified genomic DNA was enzymatically fragmented for 33-40 min at 37° C. and prepared for adapter ligation using the KAPA HyperPlus library prep kit according to manufacturer's instructions (Roche Sequencing Solutions, KK8514). SeqCap sequencing adapter final reaction concentration was 2 M, and adapter ligation reaction time was extended to 14-18 h, at 16° C. No pre-capture PCR was used following ligation reaction purification. SeqCap EZ library probe baits for either MedExome (07681330001), Onco_EZ (08333076001), or a custom Rep-Seg1 specific (see data analysis section below for design criteria) target-enrichment panel (Roche Sequencing Solutions) and 2 nM blocking oligos (Roche Sequencing Solutions), were incubated for 18-22 h at 47° C. following manufacturer instructions. Post-capture PCR was performed using KAPA HiFi HotStart ReadyMix and LM-PCR oligos for 14 cycles. Post-capture purified library concentrations were determined by Qubit (ThermoFisher) and fragment size distribution analyzed by Bioanalyzer 2100 (Agilent). Amplified enriched libraries were each diluted to 2 nM and stored at –20° C. prior to pooling for sequencing. Pooled libraries were sequenced using MiSeq and HiSeq instruments (Illumina) according to manufacturer's recommendations for paired-end sequencing using (Illumina) runs with 101 base paired-end reads. cfDNA sequencing libraries were constructed using the AVENIO ctDNA Targeted Kit (Roche, 08061076001) by following the AVENIO ctDNA Analysis Kits Reagent Workflow User Guide v1.0.0. Amplified, adapter-ligated samples were concentrated together with the Hybridization Supplement using a Vacufuge plus instrument (Eppendorf). Each sample was resuspended in the appropriate Enhancing Oligo, the custom Rep-Seq1-specific panel, and Hybridization master mix. Enrichment, hybridization cleanup and amplification were performed according to manufacturer instructions. Samples (equal mass) were pooled, and sequenced using Hiseq (Illumina), according to instructions, with 151 base paired-end reads. Multi-region, cocktail and single regions samples, from 79 renal cell carcinomas as displayed in FIG. 1, underwent renal driver Panel_v6 library preparation and sequencing, using methods as previously described[5]. Multi-region whole exome library preparation and sequencing for Rep-Seq1 was conducted by external laboratory (Eurofins Scientific), using Agilent Sure-Select Human All Exon v5 kits.

Flow Sorting Method to Increase Tumor Purity

A representative sample from formalin fixed residual tumor tissue from Rep-Seq11 was generated by homogenization in an IKA blender in autoMACS buffer (1:1 mass to volume). Aliquots of the homogenate (1 g) were further dissociated to individual nuclei by adapting a previously described method[12]. Briefly, tissue was collected by centrifugation, resuspended in CC1 buffer (5:1 mass to volume), and heated at 80° C. for 30 min. Tissue was washed once with PBS, and resuspended in PBS containing 1 mg/ml proteinase K (1:1 mass to volume) and incubated at 50° C. for 10 min. The sample was exchanged into 5 mg/ml pepsin in 150 mM NaCl, pH 1.5 and incubated 30 min at 37° C. The sample was adjusted to pH 8 with 5 M NaOH, and exchanged into PBS, 0.5% BSA and 0.5% Tween 20 prior to filtration through a 20-micromolar filter to collect nuclei.

Nuclei were then collected by centrifugation at 400×g and exchanged into antibody diluent for 30 min at 20° C. Samples were exchanged into mouse anti-cytokeratin 8/18 primary antibody directly from the dispenser for 1 hour at 4° C., washed three times in 0.5 ml PBS, 0.1% BSA and 0.1% Tween 20, and incubated for 30 min at 4° C. in goat-anti-mouse antibodies conjugated to Alexa Fluor 488 or Alexa Fluor 647 (2 microgram/ml) and DAPI (3 M). Stained samples were washed and filtered prior to analysis and sorting using a BD FACS Aria (656700, Becton Dickinson) equipped with equipped with a 355 nm, 60 mW laser and 450/50 nm filter for DAPI; 488 nm, 60 mW laser and 530/30 nm filter for AF 488; and 633 nm, 100 mW laser and 670/30 nm filter for AF 647. No compensation was used. DAPI was used for doublet discrimination. Rep-Seq11 tumor nuclei were enriched by FACS after gating to include cytokeratin positive (CK+), high side-scatter (SSC) nuclei and exclude cytokeratin negative (CK−), low SSC nuclei.

Data and Statistical Analysis

Tumor Volume Sampling Analysis

For the clinical audit data, all samples had data on width (W) and length (L) dimensions available, and tumor volume (T_V) was estimated using the following formula:

$$T\_V = (W^2 \times L)/2$$

(taken from the literature as the most accurate tumor volume measurement approach[13]).

Biopsy volume (BV) was calculated based on the 2D surface area analysis of 8 typical slides, with each slide scanned using the Aperio AT2 whole slide scanner at 40×. Each image was annotated by hand, following the perimeter of the tissue, and the surface area calculated via using the Aperio ImageScope software. The average surface area was 3.37 cm² and this value was multiplied by slide thickness (10 µm), and the total number of slides used, to obtain B_V estimates per tumor. We note that in cases where multiple slides were used for molecular profiling, (up to 5 were used), each slide was taken from the same block (i.e. all from one fixed spatial location). The proportion of total tumor volume sampled in each case is then simply calculated as B_V/T_V. For the cancer genome atlas (TCGA) dataset analysis, we extracted summary clinical annotation files for each solid tumor cohort from the Broad Institute TCGA GDAC Firehose repository. Tumor dimension data was available for n=1667 samples, across 6 tumor types: ACC, KICH, KIRC, KIRP, PAAD and THCA. Tumor volume (T_V) was calculated as per above using the formula: $T\_V = (W^2 \times L)/2$. In cases where only one dimension was given (i.e. the maximal dimension) this was assumed to be the tumor length, and the tumor width was estimated using a L:W ratio of 1:0.8, with the 0.8 standard value estimated as the median ratio value observed across all cases with available length and width data. Biopsy sample volumes were calculated from exact length (L), width (W) and depth (D) dimensions, as given in the clinical annotation files, with biopsy shape assumed to be cuboid and biopsy volume (BV) calculated as B_V=L×W× D. Where biopsy dimensions were missing in the clinical annotation files, a standard biopsy volume (B_V) of 0.48 cm³ was assumed, based on the median value from all other bases where data was available. The proportion of total tumor volume sampled in each case is then simply calculated as B_V/T_V.

Processing of Sequencing Data

Paired-end reads in FastQ format sequenced by Hiseq were aligned to the reference human genome (build hg19), using the Burrows-Wheeler Aligner (BWA) v0.7.15. with seed recurrences (−c flag) set to 10000[14]. Intermediate processing of Sam files was performed using Samtools v1.3.1 and deduplication was performed using Picard 1.81 (broadinstitute.github.io). For whole exome and renal driver Panel_v6 sequencing datasets, single Nucleotide Variant (SNV) calling was performed using Mutect v1.1.7 and small scale insertion/deletions (INDELs) were called running VarScan v2.4.1 in somatic mode with a minimum variant frequency (−min-var-freq) of 0.005, a tumor purity estimate (−tumor-purity) of 0.75 and then validated using Scalpel v0.5.3 (scalpel-discovery in—−somatic mode) (intersection between two callers taken)[15-17]. SNVs called by Mutect were further filtered using the following criteria: i) variant allele frequency (VAF)<1% in the corresponding germline sample, ii) variants that falling into mitochondrial chromosome, haplotype chromosome, HLA genes or any intergenic region were not considered, iii) presence of both forward and reverse strand reads supporting the variant. For custom Rep-Seq1 panel sequencing data, sequencing was conducted at high depth using unique molecular barcode (UMI) indexes, and UMI-tools[18] was used to group PCR duplicates and de-duplicate reads to yield one read per group. SNVs were then called using deepSNV[19], as Mutect is known to not be calibrated for higher sequencing depth levels. Varscan and Scalpel were used to call Rep-Seq1 custom panel INDELs as described above. All variants were annotated using Annovar[20]. To estimate somatic copy number alterations, CNVkit v0.7.3 was performed with default parameter on paired tumor-normal sequencing data[21]. Outliers of the derived log 2-ratio (logR) calls from CNVkit were detected and modified using Median Absolute Deviation Winsorization before case-specific joint segmentation to identify genomic segments of constant logR[22]. Tumor sample purity, ploidy and absolute copy number per segment were estimated using ABSOLUTE v1.0.6[23]. Neoantigen predictions were derived by first determining the 4-digit HLA type for each patient, along with mutations in class I HLA genes, using POLYSOLVER[24]. Next, all possible 9, 10 and 11-mer mutant peptides were computed, based on the detected somatic non-synonymous SNV and INDEL mutations in each sample. Binding affinities of mutant and corresponding wildtype peptides, relevant to the corresponding POLYSOLVER-inferred HLA alleles, were predicted using NetMHCpan (v3.0) and NetMHC (v4.0)[25]. Neoantigen binders were defined as IC50<50 nM or rank <2.0. Signature analysis was conducted on all non-synonymous mutations using package deconstructSigs[26]. We additionally checked for evidence of formalin induced artefact variants in the Rep-Seq data, given the protocol involves formalin exposed material. Formalin fixed paraffin embedded (FFPE) samples can contain artefacts, typically arising due to hydrolytic deamination of cytosine to form uracil, or thymine if the cytosine is methylated. Such artefacts are normally visible as an excess of C>T/G>A mutations at lower variant allele frequency[27]. Analysis of this in the whole exome sequencing data from Rep-Seq cases showed no evidence of excess low frequency formalin induced artefact, with the proportion of low frequency (below 5% VAF) C>T mutations being 34.0%, closely comparable to the average across all base changes (33.3%) (FIG. 9).

Analysis of Pooled Cocktail Sequencing Data

The final set of cocktail samples included 79 tumors with matched processed reference data sets from multi-region sequencing. The number of biopsies per cocktail sample ranged from 2 to 75 with a median number of 8 biopsies per tumor and a total number of 1,184 individual biopsies. As a reference data set of true variants, we used previously published multi-region sequencing variant calls from the same cases, which represented the sum of all variants detected in each tumor[5]. In our analysis we compared the overall performance of single-region and cocktail sequencing, in detecting somatic mutations from the known truth set. The single region sample was selected as one random single-region biopsy per tumor, from the overall multi-region dataset. We first evaluated the performance of the cocktail sequencing approach compared to multi-region and single region sequencing, by comparing the number of somatic variants detected per tumor with each approach. To reflect the average performance of single region biopsies, we calculated the mean number of variants detected through single-region sequencing per tumor. We next determined the detection rates of true variants in the cocktail and the single-region samples using the multi-region sequencing data as a reference. Significance was assessed with a paired Wilcoxon Test. Finally, in order to establish the accuracy of the cocktail sequencing approach, we next determined the correlation between the variant allele frequencies (VAF) of all somatic mutations detected through multi-region sequencing and the VAFs from the cocktail samples as well as a random single-region biopsy per tumor. The multi-region VAFs were calculated as the mean VAFs across all regions included in the cocktails. The correlations were calculated with a Spearman's rank-order correlation test.

Custom Panel Design

To conduct in-depth validation of the representative sequencing method high coverage profiling was conducted in case Rep-Seq1, using a custom panel. The panel design was based on whole exome sequencing results from: i) 7 biopsies taken from the Rep-Seq1 primary tumor (before homogenization) and ii) an aliquot of the Rep-Seq1 homogenized solution. SNV and INDEL mutations were called across the 8 samples as described above, and a total of 76 non-synonymous mutations were detected. These 76 mutations were successfully captured in a targeted custom panel, and sequenced to high depth (median 15,402×) in the 68 primary biopsies, 11 biopsies taken from 2 lymph node metastases, 4 biological primary Rep-Seq replicates, 6 circulating tumor (ct) DNA samples collected at different time points, and 3 homogenized lymph node Rep-Seq samples.

Jaccard Reproducibility Analysis

The reproducibility of variant discovery between Rep-Seq1 primary tumor biopsies (n=68), Rep-Seq biological replicates (n=4) and ctDNA samples (n=6) was assessed using the Jaccard similarity coefficient. Each pairwise combination between samples (within each group) was considered, e.g. Biopsy1 (A) vs Biopsy2 (B), Biopsy1 (A) vs Biopsy3 (B), etc. Jaccard similarity coefficient was calculated using the standard formula (J):

$$J = M_{11}/(M_{01}+M_{10}+M_{11})$$

where $M_{11}$ represents the total number of variants present in both samples A and B, $M_{10}$ represents the total number of variants present in A but not B and $M_{01}$ represents the total number of variants present in B but not A.

Clustering and Phylogenetic Analysis

Clustering analysis was performed on Rep-Seq1 custom panel data using PyClone Dirichlet process clustering[28]. For each mutation, the observed alternative allele count, reference count and total local tumor copy number was used as input, together with the purity for each sample. PyClone was run with 10,000 iterations and a burn-in of 1000, and default parameters, with –var_prior total_copy_number. Two separate PyClone runs were conducted, the first for the primary multi-region biopsies dataset. Of the total n=68 primary biopsies sequenced, n=52 passed quality control for clustering analysis, with n=16 biopsies excluded due to lower purity (measured based on purity being too low to call the known clonal 3p copy number loss event correctly). The second PyClone clustering run was conducted just for Rep-Seq homogenate sample alone (n=1), using the same parameters.

Illusion of Clonality Simulation

To assess the risk of illusion of clonality, a biopsy sampling approach was simulated, for 1 up to 20 biopsies taken, using the Rep-Seq1 dataset. For each biopsy number (n=1-20), a random sample of biopsies of size n was drawn from the total set of 68 primary biopsies profiled for Rep-Seq1. Within the random sampled set, the number of mutations which appeared to be clonal (based on being ubiquitously present in all biopsies in the sampled set) was calculated. This list was then compared to the known list of truly clonal mutations (from the full 68 set), and percentage of variants which were incorrectly classified as clonal was recorded. This process was repeated for 100 iterations for each n, to give a distribution, from which mean and standard deviation values were calculated.

Analysis of Purity Enriched Data

For Rep-Seq11, whole exome sequencing case conducted using the standard Rep-Seq protocol, and then repeated with the additional step of flow sorted purity enrichment. Variant calling was completed, and purity estimates calculated in both samples in the same way, as detailed above. The number of variants discovered in each sample, and then those in common across samples were calculated and plotted in FIG. 6.

Table Legends

Table S1—Characteristics of 11 representative samples from various tumor types. Tumor volume was calculated using dimensions taken from clinical pathology reports. Tumor homogenates contained an average of 54.8% of the initial tumor volume.

Table S2—Comparison of a minimal residual disease ctDNA tracking panel, biopsies versus Rep-Seq.

FIELD OF THE DISCLOSURE

The present disclosure relates to methods of identifying genetic variants in a sample, such as a representative sample. In some embodiments, the methods relate to the generation of a ctDNA monitoring panel based on an identified plurality of genetic variants in a sample, such as a representative sample.

33

Additional Embodiments

Additional Embodiment 1. A method of identifying a plurality of genetic variants in a sample comprising:

(a) homogenizing one or more tumor samples to provide a homogenized sample;

(b) preparing genomic material isolated from the homogenized sample for sequencing; and (c) identifying the plurality of genetic variants within sequencing data derived after sequencing the prepared genomic material.

Additional Embodiment 2. The method of additional embodiment 1, further comprising determining whether the identified plurality of genetic variants are clonal or subclonal.

Additional Embodiment 3. The method of additional embodiment 2, wherein one or more neoantigens are derived from the determined subclonal mutations.

Additional Embodiment 4. The method of any one of the preceding additional embodiments, further comprising generating a ctDNA monitoring panel based on the identified plurality of genetic variants.

Additional Embodiment 5. The method of additional embodiment 4, wherein the generated ctDNA monitoring panel is used to determine a response to therapy.

Additional Embodiment 6. The method of additional embodiment 4, wherein the generated ctDNA monitoring panel is used to determine an evolutionary trajectory of the cancer.

Additional Embodiment 7. The method of additional embodiment 4, wherein the generated ctDNA monitoring panel is used to predict a response to a future therapeutic strategy.

Additional Embodiment 8. The method of additional embodiment 4, wherein the generated ctDNA monitoring panel is used to ascertain a presence or absence of cancer in a patient during or following therapy.

Additional Embodiment 9. The method of additional embodiment 4, wherein the generated ctDNA monitoring panel is used to ascertain the presence of cancer in a patient following disease remission, following a complete response to therapy, or following a diagnosis of undetectable disease.

Additional Embodiment 10. The method of additional embodiment 4, wherein the generated ctDNA monitoring panel is used to detect a minimal residual disease following surgical removal of a primary tumor.

Additional Embodiment 11. The method of additional embodiment 4, wherein the generated ctDNA monitoring panel is used to detect a minimal residual disease following surgical removal of a metastatic tumor.

Additional Embodiment 12. The method of any of additional embodiments 10 and 11, wherein the primary and metastatic tumors are removed during the same surgery and the ctDNA monitoring test includes variants detected in multiple tumors from a single patient.

Additional Embodiment 13. The method of any one of the preceding additional embodiments, further comprising computing a clonal structure based on the identified plurality of genetic variants.

Additional Embodiment 14. The method of additional embodiment 13, wherein the computing of the clonal structure comprises (i) calculating cancer cell fraction estimates for each of the plurality of identified genetic variants; and (ii) grouping the calculated cancer cell fraction estimates into mutational clusters.

Additional Embodiment 15. The method of additional embodiment 14, further comprising assessing the separation of individual identified genetic variants.

Additional Embodiment 16. The method of any one of the preceding additional embodiments, further comprising sorting cellular particles within the homogenized sample prior to the preparing of the genomic material.

Additional Embodiment 17. The method of additional embodiment 16, wherein the sorting of the cellular particles is based on size.

Additional Embodiment 18. The method of additional embodiment 16, wherein the sorting of the cellular particles is based on a presence of one or more biomarkers.

Additional Embodiment 19. The method of additional embodiment 2, further comprising evaluating whether a human subject is at elevated risk of rapid disease progression if one or more high risk subclonal variants are identified within the plurality of identified genetic variants.

Additional Embodiment 20. The method of additional embodiment 2, further comprising determining a therapeutic strategy based on the identification of one or more particular subclonal variants within the plurality of identified genetic variants.

Additional Embodiment 21. The method of any one of the preceding additional embodiments, wherein the plurality of genetic variants are identified using whole genome sequencing (WGS), whole exome sequencing (WES), single nucleotide polymorphism (SNP) analysis, deep sequencing, targeted gene sequencing, polymerase chain reaction (PCR), or any combination thereof.

REFERENCES

1. Gy, P. Heterogeneite, Echantillonnage, Homogeneisation (Heterogeneity, Sampling, Homogenizing). xiv+607 p (Masson: Paris) (1988).
2. Rohde, A. Sampling and Homogenization Strategies Significantly Influence the Detection of Foodborne Pathogens in Meat. BioMed Research International (2015).
3. Crespi, I. Pre-Election Polling: Sources of Accuracy and Error. (1988).
4. David, M. Handbook of Applied Advanced Geostatistical Ore Reserve Estimation. Elsevier: Amsterdam (1988).
5. Turajlic, S. et al. Deterministic Evolutionary Trajectories Influence Primary Tumor Growth: TRACERx Renal. Cell 173, 595-610 e511 (2018).
6. Jamal-Hanjani, M. et al. Tracking the Evolution of Non-Small-Cell Lung Cancer. The New England journal of medicine 376, 2109-2121 (2017).
7. Warrick, J. I. et al. Intratumoral Heterogeneity of Bladder Cancer by Molecular Subtypes and Histologic Variants. European urology (2018).
8. Consortium, A. P. G. AACR Project GENIE: Powering Precision Medicine Through An International Consortium. Cancer discovery (2017).
9. Miao, D. et al. Genomic correlates of response to immune checkpoint blockade in microsatellite-stable solid tumors. Nature genetics 50, 1271-1281 (2018).
10. McGranahan, N. et al. Clonal neoantigens elicit T cell immunoreactivity and sensitivity to immune checkpoint blockade. Science 351, 1463-1469 (2016).
11. Abbosh, C. et al. Phylogenetic ctDNA analysis depicts early-stage lung cancer evolution. Nature 545, 446-451 (2017).
12. Hedley, D. W., Friedlander, M. L., Taylor, I. W., Rugg, C. A. & Musgrove, E. A. Method for analysis of cellular DNA content of paraffin-embedded pathological material using flow cytometry. The journal of histochemistry and cytochemistry: official journal of the Histochemistry Society 31, 1333-1335 (1983).

13. Faustino-Rocha, A. et al. Estimation of rat mammary tumor volume using caliper and ultrasonography measurements. Lab animal 42, 217-224 (2013).

14. Li, H. & Durbin, R. Fast and accurate short read alignment with Burrows-Wheeler transform. Bioinformatics 25, 1754-1760 (2009).

15. Cibulskis, K. et al. Sensitive detection of somatic point mutations in impure and heterogeneous cancer samples. Nat Biotechnol 31, 213-219 (2013).

16. Fang, H. et al. Indel variant analysis of short-read sequencing data with Scalpel. Nat Protoc 11, 2529-2548 (2016).

17. Koboldt, D. C. et al. VarScan: variant detection in massively parallel sequencing of individual and pooled samples. Bioinformatics 25, 2283-2285 (2009).

18. Smith, T., Heger, A. & Sudbery, I. UMI-tools: modeling sequencing errors in Unique Molecular Identifiers to improve quantification accuracy. Genome research 27, 491-499 (2017).

19. Gerstung, M. et al. Reliable detection of subclonal single-nucleotide variants in tumor cell populations. Nature communications 3, 811 (2012).

20. Wang, K., Li, M. Y. & Hakonarson, H. ANNOVAR: functional annotation of genetic variants from high-throughput sequencing data. Nucleic Acids Res 38 (2010).

21. Talevich, E., Shain, A. H., Botton, T. & Bastian, B. C. CNVkit: Genome-Wide Copy Number Detection and Visualization from Targeted DNA Sequencing. Plos Comput Biol 12 (2016).

22. Nilsen, G. et al. Copynumber: Efficient algorithms for single- and multi-track copy number segmentation. Bmc Genomics 13 (2012).

23. Carter, S. L. et al. Absolute quantification of somatic DNA alterations in human cancer. Nat Biotechnol 30, 413-421 (2012).

24. Shukla, S. A. et al. Comprehensive analysis of cancer-associated somatic mutations in class I HLA genes. Nature biotechnology 33, 1152-1158 (2015).

25. Andreatta, M. & Nielsen, M. Gapped sequence alignment using artificial neural networks: application to the MHC class I system. Bioinformatics 32, 511-517 (2016).

26. Rosenthal, R., McGranahan, N., Herrero, J., Taylor, B. S. & Swanton, C. DeconstructSigs: delineating mutational processes in single tumors distinguishes DNA repair deficiencies and patterns of carcinoma evolution. Genome biology 17, 31 (2016).

27. Wong, S. Q. et al. Sequence artefacts in a prospective series of formalin-fixed tumors tested for mutations in hotspot regions by massively parallel sequencing. BMC medical genomics 7, 23 (2014).

28. Roth, A. et al. PyClone: statistical inference of clonal population structure in cancer. Nat Methods 11, 396-398 (2014).

Although the present disclosure has been described with reference to a number of illustrative embodiments, it should be understood that numerous other modifications and embodiments can be devised by those skilled in the art that will fall within the spirit and scope of the principles of this disclosure. More particularly, reasonable variations and modifications are possible in the component parts and/or arrangements of the subject combination arrangement within the scope of the foregoing disclosure, the drawings, and the appended claims without departing from the spirit of the disclosure. In addition to variations and modifications in the component parts and/or arrangements, alternative uses will also be apparent to those skilled in the art.

TABLE S1

| Sample-ID | Histology | Stage | Mass dimensions (cm) (W × L × D) | Estimated volume (cm3) | Rep-Seq sampled tissue weight (grams) | Estimated proportion sampled* |
|---|---|---|---|---|---|---|
| Rep-Seq1 | Clear cell renal cell carcinoma | IV | 17.0 × 13.6 × 12.8 | 1965.2 | 1258.0 | 64.0% |
| Rep-Seq2 | Clear cell renal cell carcinoma | I | 4.2 × 3.4 × 2 | 30.0 | 7.0 | 23.3% |
| Rep-Seq3 | Clear cell renal cell carcinoma | II | 13.5 × 10.8 × 8.6 | 984.2 | 750.0 | 76.2% |
| Rep-Seq4 | Invasive lobular breast carcinoma | IIIC | 3.5 × 3 × 2 | 18.4 | 16.6 | 90.3% |
| Rep-Seq5 | Invasive ductal breast carcinoma | IIB | 11 × 7 × 7 | 423.5 | 127.0 | 30.0% |
| Rep-Seq6 | Colon adenocarcinoma | IIA | 2.5 × 2.5 × 0.3 | 7.8 | 2.5 | 31.6% |
| Rep-Seq7 | Colon adenocarcinoma | IIA | 9 × 5.5 × 2 | 222.8 | 83.7 | 37.6% |
| Rep-Seq8 | Non-small cell lung cancer | IIA | 3.1 × 3 × 2.2 | 14.4 | 18.2 | 100.0% |
| Rep-Seq9 | Non-small cell lung cancer | IIB | 7.1 × 6.3 × 4 | 158.8 | 60.8 | 38.3% |

TABLE S1-continued

| Sample-ID | Histology | Stage | Mass dimensions (cm) (W × L × D) | Estimated volume (cm3) | Rep-Seq sampled tissue weight (grams) | Estimated proportion sampled* |
|---|---|---|---|---|---|---|
| Rep-Seq10 | Non-small cell lung cancer | III | 4 × 2.3 × 2 | 18.4 | 9.3 | 50.6% |
| Rep-Seq11 | Colon adenocarcinoma | NA | 7.4 × 7 × 5.2 | 205.4 | 125.2 | 61.0% |

*Assuming 1 cm3 equals approximately 1 gram

TABLE S2

Comparison of a minimal residual disease ctDNA tracking panel, designed based on either Rep-Seq or biopsy sequencing of tumor tissue. The overall median number of mutations detected per timepoint from all Rep-Seq and biopsy replicates is given, and below is the complete dataset from all individual samples. The % difference in the number of mutations detected is shown. Also shown is the % of times MRD would be missed ("%_MRD_missed"), this assumes a minimum of => 3 unique tumour mutations would need to be detected in ctDNA to reliably confirm disease relapse.

| Sample | Type | p1 | p10 | p16 | p20 | PCE_PLF | PCE_PTF |
|---|---|---|---|---|---|---|---|
| Median_rep_seq | rep_seq | 34 | 24 | 4 | 8 | 34 | 35 |
| Median_biopsy | biopsy | 25 | 20 | 2 | 6 | 33 | 33 |
| % diff | — | 36% | 20% | 100% | 33% | 3% | 6% |
| %_MRD_missed_rep_seq | rep_seq | 0% | 0% | 0% | 0% | 0% | 0% |
| %_MRD_missed_biopsy | biopsy | 0% | 0% | 53% | 0% | 0% | 0% |
| RepSeq1 | rep_seq | 34 | 24 | 4 | 8 | 34 | 35 |
| RepSeq2 | rep_seq | 34 | 24 | 4 | 8 | 34 | 35 |
| RepSeq3 | rep_seq | 32 | 24 | 3 | 8 | 34 | 35 |
| RepSeq4 | rep_seq | 34 | 24 | 4 | 8 | 34 | 35 |
| MRB2 | biopsy | 33 | 25 | 3 | 8 | 34 | 35 |
| MRB3 | biopsy | 33 | 24 | 3 | 8 | 34 | 35 |
| MRB4 | biopsy | 33 | 23 | 3 | 8 | 34 | 35 |
| MRB6 | biopsy | 32 | 24 | 3 | 8 | 34 | 35 |
| MRB5 | biopsy | 32 | 23 | 3 | 8 | 34 | 35 |
| MRB33 | biopsy | 31 | 24 | 2 | 8 | 33 | 34 |
| MRB69 | biopsy | 29 | 23 | 3 | 6 | 33 | 34 |
| MRB25 | biopsy | 30 | 22 | 3 | 6 | 31 | 32 |
| MRB77 | biopsy | 27 | 21 | 2 | 6 | 34 | 34 |
| MRB44 | biopsy | 30 | 21 | 3 | 6 | 31 | 32 |
| MRB24 | biopsy | 29 | 21 | 3 | 6 | 31 | 32 |
| MRB27 | biopsy | 29 | 21 | 3 | 6 | 31 | 32 |
| MRB30 | biopsy | 29 | 21 | 3 | 6 | 31 | 32 |
| MRB37 | biopsy | 26 | 21 | 2 | 6 | 33 | 34 |
| MRB40 | biopsy | 29 | 21 | 3 | 6 | 31 | 32 |
| MRB49 | biopsy | 29 | 21 | 3 | 6 | 31 | 32 |
| MRB55 | biopsy | 29 | 21 | 3 | 6 | 31 | 32 |
| MRB63 | biopsy | 29 | 21 | 3 | 6 | 31 | 32 |
| MRB64 | biopsy | 29 | 21 | 3 | 6 | 31 | 32 |
| MRB1 | biopsy | 26 | 20 | 1 | 6 | 34 | 34 |
| MRB43 | biopsy | 29 | 21 | 2 | 6 | 31 | 32 |
| MRB7 | biopsy | 26 | 20 | 1 | 6 | 34 | 34 |
| MRB32 | biopsy | 28 | 21 | 3 | 5 | 31 | 32 |
| MRB13 | biopsy | 25 | 20 | 0 | 6 | 34 | 34 |
| MRB14 | biopsy | 25 | 20 | 0 | 6 | 34 | 34 |
| MRB39 | biopsy | 25 | 21 | 1 | 6 | 33 | 33 |
| MRB79 | biopsy | 25 | 20 | 0 | 6 | 34 | 34 |
| MRB17 | biopsy | 25 | 20 | 1 | 6 | 33 | 33 |
| MRB18 | biopsy | 25 | 20 | 1 | 6 | 33 | 33 |
| MRB19 | biopsy | 25 | 20 | 1 | 6 | 33 | 33 |
| MRB75 | biopsy | 25 | 19 | 0 | 6 | 34 | 34 |
| MRB11 | biopsy | 24 | 19 | 0 | 6 | 34 | 34 |
| MRB35 | biopsy | 25 | 20 | 0 | 6 | 33 | 33 |
| MRB45 | biopsy | 26 | 20 | 3 | 5 | 31 | 32 |
| MRB58 | biopsy | 26 | 20 | 3 | 5 | 31 | 32 |
| MRB59 | biopsy | 26 | 20 | 3 | 5 | 31 | 32 |
| MRB60 | biopsy | 26 | 20 | 3 | 5 | 31 | 32 |
| MRB62 | biopsy | 26 | 20 | 3 | 5 | 31 | 32 |
| MRB10 | biopsy | 24 | 18 | 0 | 6 | 34 | 34 |
| MRB12 | biopsy | 24 | 18 | 0 | 6 | 34 | 34 |
| MRB15 | biopsy | 24 | 20 | 0 | 6 | 33 | 33 |
| MRB21 | biopsy | 24 | 20 | 0 | 6 | 33 | 33 |
| MRB28 | biopsy | 26 | 20 | 3 | 4 | 31 | 32 |
| MRB38 | biopsy | 24 | 20 | 0 | 6 | 33 | 33 |
| MRB70 | biopsy | 24 | 18 | 0 | 6 | 34 | 34 |

TABLE S2-continued

Comparison of a minimal residual disease ctDNA tracking panel, designed based on either Rep-Seq or biopsy sequencing of tumor tissue. The overall median number of mutations detected per timepoint from all Rep-Seq and biopsy replicates is given, and below is the complete dataset from all individual samples. The % difference in the number of mutations detected is shown. Also shown is the % of times MRD would be missed ("%_MRD_missed"), this assumes a minimum of => 3 unique tumour mutations would need to be detected in ctDNA to reliably confirm disease relapse.

| Sample | Type | p1 | p10 | p16 | p20 | PCE_PLF | PCE_PTF |
|---|---|---|---|---|---|---|---|
| MRB71 | biopsy | 24 | 18 | 0 | 6 | 34 | 34 |
| MRB72 | biopsy | 24 | 18 | 0 | 6 | 34 | 34 |
| MRB73 | biopsy | 24 | 18 | 0 | 6 | 34 | 34 |
| MRB74 | biopsy | 24 | 18 | 0 | 6 | 34 | 34 |
| MRB76 | biopsy | 24 | 18 | 0 | 6 | 34 | 34 |
| MRB78 | biopsy | 24 | 18 | 0 | 6 | 34 | 34 |
| MRB8 | biopsy | 24 | 18 | 0 | 6 | 34 | 34 |
| MRB80 | biopsy | 24 | 18 | 0 | 6 | 34 | 34 |
| MRB9 | biopsy | 24 | 18 | 0 | 6 | 34 | 34 |
| MRB16 | biopsy | 24 | 19 | 0 | 6 | 33 | 33 |
| MRB20 | biopsy | 24 | 19 | 0 | 6 | 33 | 33 |
| MRB31 | biopsy | 26 | 19 | 3 | 4 | 31 | 32 |
| MRB34 | biopsy | 24 | 19 | 0 | 6 | 33 | 33 |
| MRB36 | biopsy | 24 | 19 | 0 | 6 | 33 | 33 |
| MRB23 | biopsy | 25 | 19 | 3 | 4 | 31 | 32 |
| MRB29 | biopsy | 25 | 19 | 3 | 4 | 31 | 32 |
| MRB46 | biopsy | 25 | 19 | 3 | 4 | 31 | 32 |
| MRB47 | biopsy | 25 | 19 | 3 | 4 | 31 | 32 |
| MRB50 | biopsy | 25 | 19 | 3 | 4 | 31 | 32 |
| MRB51 | biopsy | 25 | 19 | 3 | 4 | 31 | 32 |
| MRB53 | biopsy | 25 | 19 | 3 | 4 | 31 | 32 |
| MRB54 | biopsy | 25 | 19 | 3 | 4 | 31 | 32 |
| MRB57 | biopsy | 25 | 19 | 3 | 4 | 31 | 32 |
| MRB61 | biopsy | 25 | 19 | 3 | 4 | 31 | 32 |
| MRB22 | biopsy | 25 | 19 | 2 | 4 | 31 | 32 |
| MRB56 | biopsy | 25 | 19 | 2 | 4 | 31 | 32 |
| MRB65 | biopsy | 25 | 19 | 2 | 4 | 31 | 32 |
| MRB48 | biopsy | 24 | 19 | 3 | 4 | 30 | 31 |
| MRB68 | biopsy | 23 | 19 | 0 | 5 | 32 | 32 |

The invention claimed is:

1. A method comprising:
(a) homogenizing a fixed tumor sample from a patient diagnosed with cancer to provide a homogenized sample, wherein the fixed tumor sample is residual tumor tissue, wherein any aliquot removed from the homogenized sample comprises a plurality of genetic mutations at a proportion at which they existed within the residual tumor tissue;
(b) sequencing genomic material derived from the homogenized sample to obtain a sequencing data set for the homogenized sample;
(c) identifying the plurality of genetic mutations within the obtained sequencing data set,
(d) identifying one or more common genetic mutations of the plurality of genetic mutations that are present in all cells in the homogenized sample;
(e) identifying one or more specific genetic mutations of the plurality of genetic mutations that are present in one or more subpopulations of cells within the homogenized sample but not in all cells in the homogenized sample;
(f) preparing a ctDNA monitoring panel specific for the patient diagnosed with cancer and based on (i) the identified one or more common genetic mutations present in all cells in the homogenized sample, and (ii) the identified one or more specific genetic mutations present in the one or more subpopulations of cells within the homogenized sample but not in all cells in the homogenized sample; and
(g) using the prepared ctDNA monitoring panel, repeatedly determining in one or more ctDNA samples obtained from the patient diagnosed with cancer which of the identified one or more specific genetic mutations present in the one or more subpopulations of cells has recurred or is resistant to therapy.

2. The method of claim 1, further comprising determining a response to therapy.

3. The method of claim 1, further comprising predicting a response to a future therapeutic strategy.

4. The method of claim 1, further comprising ascertaining a presence or absence of cancer in a patient during or following therapy.

5. The method of claim 1, further comprising detecting a minimal residual disease following surgical removal of a primary tumor.

6. The method of claim 1, further comprising detecting a minimal residual disease following surgical removal of a metastatic tumor.

7. The method of claim 1, wherein the homogenized sample includes genetic mutations from multiple residual tumor tissues from a single patient.

8. The method of claim 1, further comprising computing a clonal structure based on the identified plurality of genetic mutations, wherein the computing of the clonal structure comprises (i) calculating cancer cell fraction estimates for each of the plurality of identified genetic mutations; and (ii) grouping the calculated cancer cell fraction estimates into mutational clusters.

9. The method of claim 1, further comprising sorting cellular particles within the homogenized sample prior to the sequencing of the genomic material.

10. The method of claim 9, wherein the sorting of the cellular particles is based on size.

11. The method of claim 9, wherein the sorting of the cellular particles is based on a presence of one or more biomarkers.

12. The method of claim 1, further comprising determining a therapeutic strategy based on the identification of the one or more specific genetic mutations of the plurality of genetic mutations that are present in the one or more subpopulations of cells within the homogenized sample but not in all the cells in the homogenized sample.

13. The method of claim 1, wherein the sequencing with the sequencing comprises whole genome sequencing (WGS), whole exome sequencing (WES), single nucleotide polymorphism (SNP) analysis, deep sequencing, targeted gene sequencing, polymerase chain reaction (PCR), or any combination thereof.

14. The method of claim 1, wherein the residual tumor tissue is homogenized with a mechanical shearing apparatus.

15. The method of claim 14, wherein the mechanical shearing apparatus is an ultra sonicator.

16. The method of claim 14, wherein the mechanical shearing apparatus is a blender.

17. The method of claim 16, wherein the residual tumor tissue is mechanically sheared in the blender for about 2 minutes.

18. The method of claim 16, wherein the residual tumor tissue is mechanically sheared in the blender at about 15,000 rpm.

19. The method of claim 14, wherein the residual tumor tissue is mechanically sheared for a time period and at an energy based on the collagen content of the residual tumor tissue.

20. The method of claim 14, further comprising dissociating the homogenized sample to provide dissociated cells nuclei, and/or small tissue aggregates.

21. The method of claim 20, wherein the dissociation comprises mechanical dissociation, chemical dissociation, or enzymatic dissociation.

22. The method of claim 1, further comprising filtering the homogenized sample.

* * * * *